(12) United States Patent
Rota et al.

(10) Patent No.: US 7,776,521 B1
(45) Date of Patent: Aug. 17, 2010

(54) CORONAVIRUS ISOLATED FROM HUMANS

(75) Inventors: Paul A. Rota, Decatur, GA (US); Larry J. Anderson, Atlanta, GA (US); William J. Bellini, Lilburn, GA (US); Michael D. Bowen, Decatur, GA (US); Cara Carthel Burns, Avondale Estates, GA (US); Raymond Campagnoli, Decatur, GA (US); Qi Chen, Marietta, GA (US); James A. Comer, Decatur, GA (US); Byron T. Cook, Augusta, GA (US); Shannon L. Emery, Lusaka (ZM); Dean D. Erdman, Decatur, GA (US); Cynthia S. Goldsmith, Lilburn, GA (US); Jeanette Guarner, Decatur, GA (US); Charles D. Humphrey, Lilburn, GA (US); Joseph P. Icenogle, Atlanta, GA (US); Thomas G. Ksiazek, Lilburn, GA (US); Richard F. Meyer, Roswell, GA (US); Stephan S. Monroe, Decatur, GA (US); William Allan Nix, Bethlehem, GA (US); M. Steven Oberste, Lilburn, GA (US); Christopher D. Paddock, Atlanta, GA (US); Teresa C. T. Peret, Atlanta, GA (US); Pierre E. Rollin, Lilburn, GA (US); Mark A. Pallansch, Lilburn, GA (US); Anthony Sanchez, Lilburn, GA (US); Wun-Ju Shieh, Norcross, GA (US); Suxiang Tong, Alpharetta, GA (US); Sherif R. Zaki, Atlanta, GA (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 96 days.

(21) Appl. No.: 11/748,359

(22) Filed: May 14, 2007

Related U.S. Application Data

(62) Division of application No. 10/822,904, filed on Apr. 12, 2004, now Pat. No. 7,220,852.

(60) Provisional application No. 60/465,927, filed on Apr. 25, 2003.

(51) Int. Cl.
  *C12Q 1/70* (2006.01)
  *C07H 21/00* (2006.01)
  *C12N 15/50* (2006.01)
(52) U.S. Cl. .............. 435/5; 536/24.32; 536/24.33
(58) Field of Classification Search ............... None
  See application file for complete search history.

(56) References Cited

U.S. PATENT DOCUMENTS

2005/0181357 A1* 8/2005 Peiris et al. ............... 435/5

FOREIGN PATENT DOCUMENTS

WO  WO 2004/092360  10/2004

OTHER PUBLICATIONS

Ksiazek et al (New England Journal of Medicine 348:1953-1966, published online Apr. 10, 2003).*
Gut et al (Journal of Virological Methods 77:37-46, 1999).*
Neilan et al (Nucleic Acids Research 25:2938-9, 1997).*
Peiris et al (Lancet, 361:1319-1325, published online Apr. 8, 2003).*
Genbank Accession No. AY274119.1 GI:29826276 (Apr. 14, 2003).*
SARS-associated Coronavirus. Genomic Sequence Availability. [online] [retreived on Aug. 8, 2005]. Retrieved from the Internet <URL: http://www.bcgsc.ca/bioinfo/SARS>.*
"Update: Outbreak of Severe Acute Respiratory Syndrome—Worldwide, 2003," *MMWR Weekly* 52:241-248, 2003.
Emery et al., "Real-Time Reverse Transcription-Polymerase Chain Reaction Assay for SARS-Associated Coronavirus," *Emerg. Infect. Diseases* 10:311-316, 2004.
Goldsmith et al., "Ultrastructural Characterization of SARS Coronavirus," *Emerg. Infect. Diseases* 10:320-326, 2004.
Ksiazek et al., "A Novel Coronavirus Associated with Severe Acute Respiratory Syndrome," *N. Engl. J. Med.* 348:1953-1966, 2003.
Luo and Luo, "Initial SARS Coronavirus Genome Sequence Analysis Using a Bioinformatics Platform," *2nd Asia-Pacific Bioinformatics Conference (APBC2004)*, Dunedin, New Zealand, 2004.
Marra et al., "The Genome Sequence of the SARS-Associated Coronavirus," *Science* 300:1393-1404, 2003.
Supplementary Online Material for Marra et al., www.sciencemag.org/cgi/content/full/1085953/DC1, (2003).
Rota et al., "Characterization of a Novel Coronavirus Associated with Severe Acute Respiratory Syndrome," *Science* 300:1394-1399, 2003.
Supplementary Online Material for Rota et al., www.sciencemag.org/cgi/content/full/1085953/DC1, (2003).
GenBank Accession No. AY274119, Apr. 14, 2003.
GenBank Accession No. AY278741, Apr. 21, 2003.
GenBank Accession No. AY278554.1, Apr. 18, 2003.
GenBank Accession No. AY278491.1, Apr. 18, 2003.
GenBank Accession No. AY278487, Apr. 21, 2003.

* cited by examiner

*Primary Examiner*—Mary E Mosher
(74) *Attorney, Agent, or Firm*—Klarquist Sparkman, LLP

(57) ABSTRACT

Disclosed herein is a newly isolated human coronavirus (SARS-CoV), the causative agent of severe acute respiratory syndrome (SARS). Also provided are the nucleic acid sequence of the SARS-CoV genome and the amino acid sequences of the SARS-CoV open reading frames, as well as methods of using these molecules to detect a SARS-CoV and detect infections therewith. Immune stimulatory compositions are also provided, along with methods of their use.

7 Claims, 7 Drawing Sheets

Figure 1A:
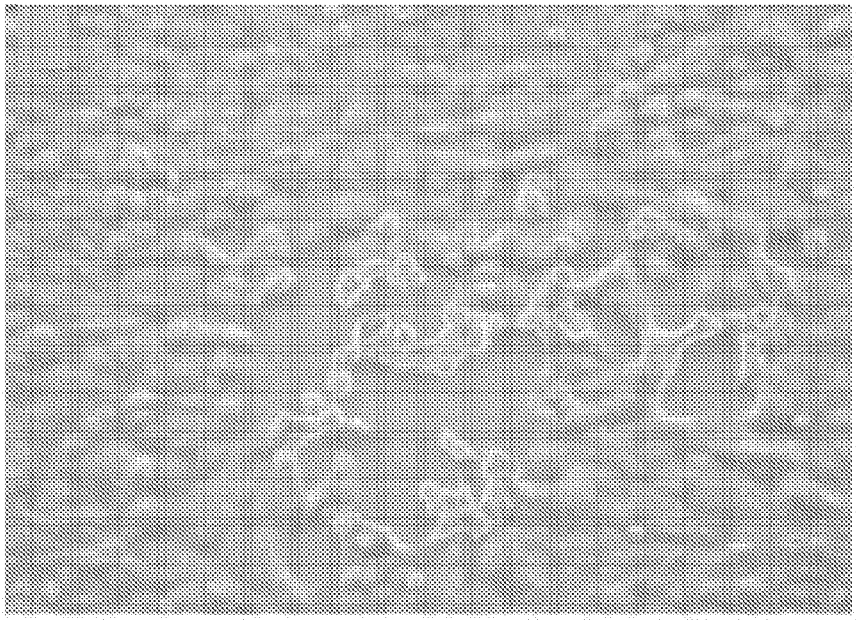

FIG. 5A
FIG. 5B
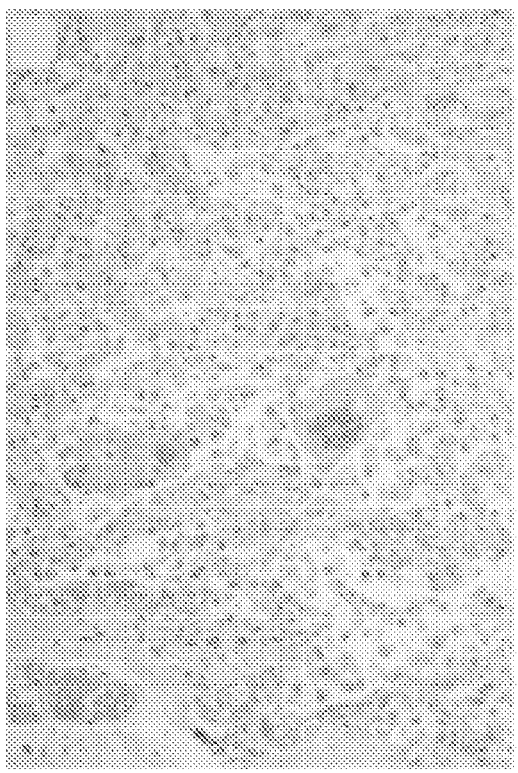
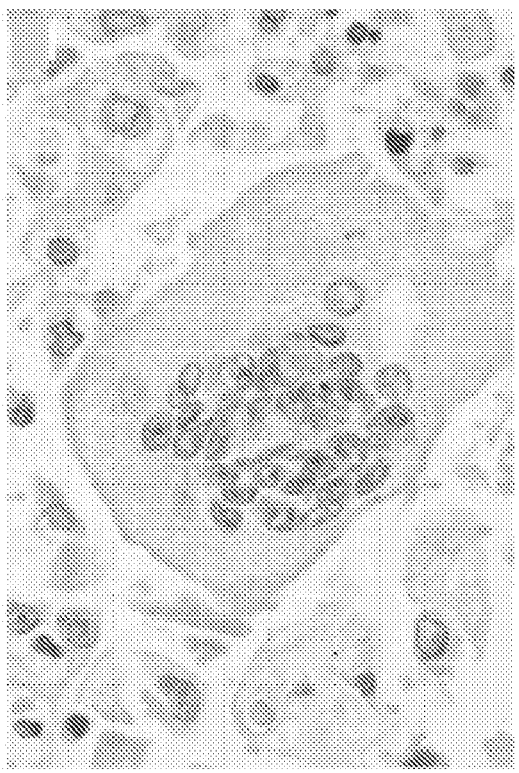
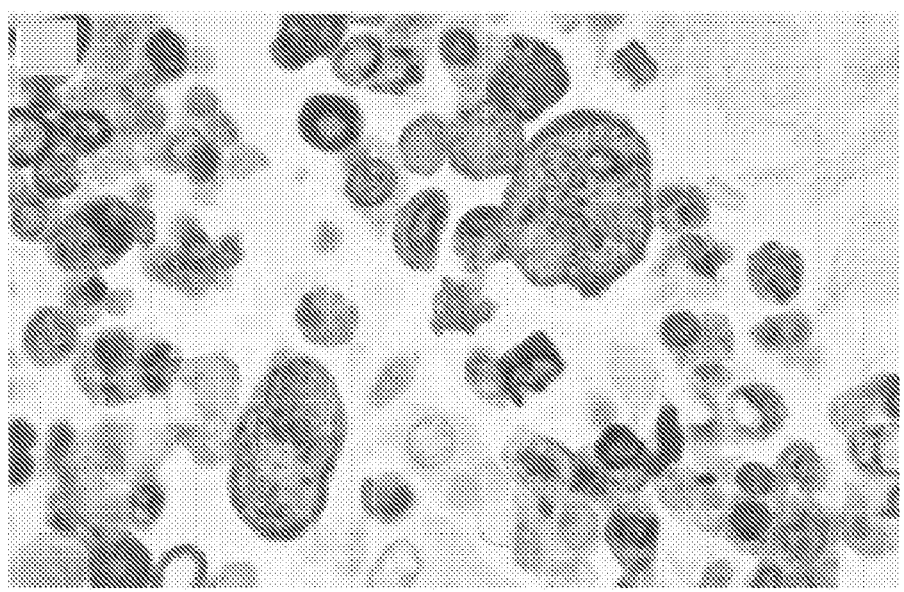
FIG. 5C

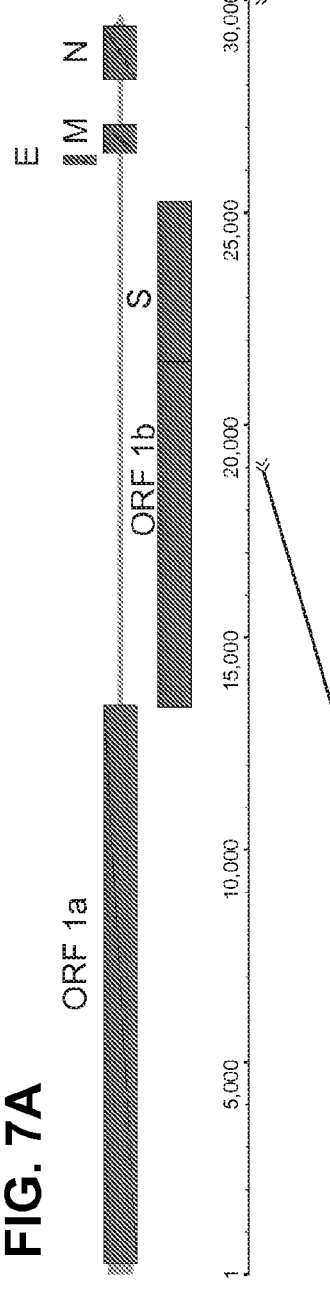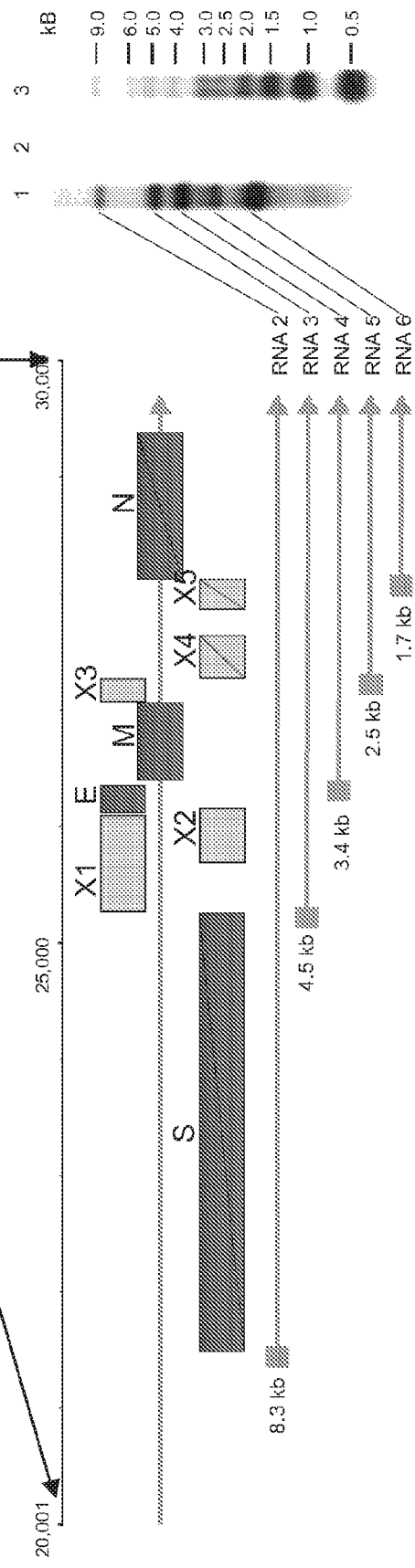
FIG. 7A
FIG. 7B
FIG. 7C

CORONAVIRUS ISOLATED FROM HUMANS

PRIORITY CLAIM

This is a division of co-pending U.S. patent application Ser. No. 10/822,904, filed Apr. 12, 2004, and issued as U.S. Pat. No. 7,220,852 on May 22, 2007, which in turn claims the benefit of U.S. Provisional Patent Application No. 60/465,927 filed Apr. 25, 2003. Both applications are incorporated herein by reference in their entirety.

STATEMENT OF GOVERNMENT SUPPORT

This invention was made by the Centers for Disease Control and Prevention, an agency of the United States Government. Therefore, the U.S. Government has certain rights in this invention.

FIELD OF THE DISCLOSURE

This invention relates to a newly isolated human coronavirus. More particularly, it relates to an isolated coronavirus genome, isolated coronavirus proteins, and isolated nucleic acid molecules encoding the same. The disclosure further relates to methods of detecting a severe acute respiratory syndrome-associated coronavirus and compositions comprising immunogenic coronavirus compounds.

BACKGROUND

The coronaviruses (order Nidovirales, family Coronaviridae, genus *Coronavirus*) are a diverse group of large, enveloped, positive-stranded RNA viruses that cause respiratory and enteric diseases in humans and other animals. At approximately 30,000 nucleotides (nt), their genome is the largest found in any of the RNA viruses. Coronaviruses are spherical, 100-160 nm in diameter with 20-40 nm complex club shaped surface projections surrounding the periphery. Coronaviruses share common structural proteins including a spike protein (S), membrane protein (M), envelope protein (E), and, in a subset of coronaviruses, a hemagglutinin-esterase protein (HE). The S protein, a glycoprotein which protrudes from the virus membrane, is involved in host cell receptor binding and is a target for neutralizing antibodies. The E and M proteins are involved in virion formation and release from the host cell. Coronavirus particles are found within the cisternae of the rough endoplasmic reticulum and in vesicles of infected host cells where virions are assembled. The coronavirus genome consists of two open reading frames (ORF1a and ORF1b) yielding an RNA polymerase and a nested set of subgenomic mRNAs encoding structural and nonstructural proteins, including the S, E, M, and nucleocapsid (N) proteins. The genus *Coronavirus* includes at least 13 species which have been subdivided into at least three groups (groups I, II, and III) on the basis of serological and genetic properties (deVries et al., *Sem. Virol.* 8:33-47, 1997; Fields et al. eds. *Fields Virology*, 3rd edition, Raven Press, Philadelphia, 1323-1341, 1996; Mahey and Collier eds. *Microbiology and Microbial Infections*, Volume 1 Virology, 9$^{th}$ edition, Oxford University Press, 463-479, 1998).

The three known groups of coronavirus are associated with a variety of diseases of humans and domestic animals (for example, cattle, pigs, cats, dogs, rodents, and birds), including gastroenteritis and upper and lower respiratory tract disease. Known coronaviruses include human Coronavirus 229E (HCoV-229E), canine coronavirus (CCoV), feline infectious peritonitis virus (FIPV), porcine transmissible gastroenteritis virus (TGEV), porcine epidemic diarrhea virus (PEDV), human coronavirus OC43 (HCoV-OC43), bovine coronavirus (BCoV), porcine hemagglutinating encephalomyelitis virus (HEV), rat sialodacryoadenitis virus (SDAV), mouse hepatitis virus (MHV), turkey coronavirus (TCoV), and avian infectious bronchitis virus (IBV-Avian) (Fields et al. eds. *Fields Virology*, 3rd edition, Raven Press, Philadelphia, 1323-1341, 1996; Mahey and Collier eds. *Microbiology and Microbial Infections*, Volume 1 Virology, 9$^{th}$ edition, Oxford University Press, 463-479, 1998).

*Coronavirus* infections are generally host specific with respect to infectivity and clinical symptoms. Coronaviruses further exhibit marked tissue tropism; infection in the incorrect host species or tissue type may result in an abortive infection, mutant virus production and altered virulence. Coronaviruses generally do not grow well in cell culture, and animal models for human *coronavirus* infection are lacking. Therefore, little is known about them (Fields et al. eds. Fields Virology, 3rd edition, Raven Press, Philadelphia, 1323-1341, 1996). The known human coronaviruses are notably fastidious in cell culture, preferring select cell lines, organ culture, or suckling mice for propagation. Coronaviruses grown in cell culture exhibit varying degrees of virulence and/or cytopathic effect (CPE) depending on the host cell type and culture conditions. The only human or animal coronavirus which has been shown to grow in Vero E6 cells is PEDV, and it requires the addition of trypsin to culture medium for growth in Vero E6 cells. Moreover, PEDV adapted to Vero E6 cell culture results in a strikingly different CPE, with cytoplasmic vacuoles and the formation of large syncytia (Hofmann and Wyler, *J. Clin. Micro.* 26:2235-39, 1988; Kusanagi et el., *J. Vet. Med. Sci.* 554:313-18, 1991).

Coronavirus have not previously been known to cause severe disease in humans, but have been identified as a major cause of upper respiratory tract illness, including the common cold. Repeat infections in humans are common within and across serotype, suggesting that immune response to coronavirus infection in humans is either incomplete or short lived. Coronavirus infection in animals can cause severe enteric or respiratory disease. Vaccination has been used successfully to prevent and control some coronavirus infections in animals. The ability of animal-specific coronaviruses to cause severe disease raises the possibility that coronavirus could also cause more severe disease in humans (Fields et al. eds. *Fields Virology,* 3rd edition, Raven Press, Philadelphia, 1323-1341, 1996; Mahey and Collier eds. *Microbiology and Microbial Infections*, Volume 1 Virology, $9^{th}$ edition, Oxford University Press, 463-479, 1998).

In late 2002, cases of life-threatening respiratory disease with no identifiable etiology were reported from Guangdong Province, China, followed by reports from Vietnam, Canada, and Hong Kong of severe febrile respiratory illness that spread to household members and health care workers. The syndrome was designated "severe acute respiratory syndrome" (SARS) in February 2003 by the Centers for Disease Control and Prevention (*MMWR,* 52:241-48, 2003).

Past efforts to develop rapid diagnostics and vaccines for coronavirus infection in humans have been hampered by a lack of appropriate research models and the moderate course of disease in humans. Therefore, a need for rapid diagnostic tests and vaccines exists.

SUMMARY OF THE DISCLOSURE

A newly isolated human coronavirus has been identified as the causative agent of SARS, and is termed SARS-CoV. The nucleic acid sequence of the SARS-CoV genome and the amino acid sequences of the SARS-CoV open reading frames are provided herein.

This disclosure provides methods and compositions useful in detecting the presence of a SARS-CoV nucleic acid in a sample and/or diagnosing a SARS-CoV infection in a subject. Also provided are methods and compositions useful in detecting the presence of a SARS-CoV antigen or antibody in a sample and/or diagnosing a SARS-CoV infection in a subject.

The foregoing and other features and advantages will become more apparent from the following detailed description of several embodiments, which proceeds with reference to the accompanying figures.

BRIEF DESCRIPTION OF THE FIGURES

FIGS. 1A-B are photomicrographs illustrating typical early cytopathic effects seen with coronavirus isolates and serum from SARS patients. FIG. 1A is a photomicrograph of Vero E6 cells inoculated with an oropharyngeal specimen from a SARS patient (x40). FIG. 1B is a photomicrograph of infected Vero E6 cells reacting with the serum of a convalescent SARS patient in an indirect fluorescent antibody (IFA) assay (x400).

FIGS. 2A-B are electronmicrographs illustrating ultrastructural characteristics of the SARS-associated coronavirus (SARS-CoV). FIG. 2A is a thin-section electron-microscopical view of viral nucleocapsids aligned along the membrane of the rough endoplasmic reticulum (arrow) as particles bud into the cisternae. Enveloped virions have surface projections (arrowhead) and an electron-lucent center. Directly under the viral envelope lies a characteristic ring formed by the helical nucleocapsid, often seen in cross-section. FIG. 2B is a negative stain (methylamine tungstate) electronmicrograph showing stain-penetrated coronavirus particle with the typical internal helical nucleocapsid-like structure and club-shaped surface projections surrounding the periphery of the particle. Bars: 100 nm.

FIG. 3 is an estimated maximum parsimony tree illustrating putative phylogenetic relationships between SARS-CoV and other human and animal coronaviruses. Phylogenetic relationships are based on sequence alignment of 405 nucleotides of the coronavirus polymerase gene ORF1b (nucleic acid 15,173 to 15,578 of SEQ ID NO: 1). The three major coronavirus antigenic groups (I, II and III), represented by HCoV-229E, CCoV, FIPV, TGEV, PEDV, HCoV-OC43, BCoV, HEV, SDAV, MHV, TCoV, and IBV-Avian, are shown shaded. Bootstrap values (100 replicates) obtained from a 50% majority rule consensus tree are plotted at the main internal branches of the phylogram. Branch lengths are proportionate to nucleotide differences.

FIG. 4 is a pictorial representation of neighbor joining trees illustrating putative phylogenetic relationships between SARS-CoV and other human and animal coronaviruses. Amino acid sequences of the indicated SARS-CoV proteins were compared with those from reference viruses representing each species in the three groups of coronaviruses for which complete genomic sequence information was available [group 1: HCoV-229E (AF304460); PEDV (AF353511); TGEV (AJ271965); group 2: BCoV (AF220295); MHV (AF201929); group 3: infectious bronchitis virus (M95169)]. Sequences for representative strains of other coronavirus species, for which partial sequence information was available, were included for some of the structural protein comparisons [group 1: CCoV (D13096); FCoV (AY204704); porcine respiratory coronavirus (Z24675); group 2: HCoV-OC43 (M76373, L14643, M93390); HEV (AY078417); rat coronavirus (AF207551)]. Sequence alignments and neighbor joining trees were generated by using Clustalx 1.83 with the Gonnet protein comparison matrix. The resulting trees were adjusted for final output using treetool 2.0.1.

FIGS. 5A-C are photomicrographs illustrating diffuse alveolar damage in a patient with SARS (FIGS. 5A-B), and immunohistochemical staining of SARS-CoV-infected Vero E6 cells (FIG. 5C). FIG. 5A is a photomicrograph of lung tissue from a SARS patient (x50). Diffuse alveolar damage, abundant foamy macrophages and multinucleated syncytial cells are present; hematoxylin and eosin stain was used. FIG. 5B is a higher magnification photomicrograph of lung tissue from the same SARS patient (x250). Syncytial cells show no conspicuous viral inclusions. FIG. 5C is a photomicrograph of immunohistochemically stained SARS-CoV-infected cells (x250). Membranous and cytoplasmic immunostaining of individual and syncytial Vero E6 cells was achieved using feline anti-FIPV-1 ascitic fluid. Immunoalkaline phosphatase with naphthol-fast red substrate and hematoxylin counter stain was used.

FIGS. 6A-B are electronmicrographs illustrating ultrastructural characteristics of a coronavirus-infected cell in bronchoalveolar lavage (BAL) from a SARS patient. FIG. 6A is an electron micrograph of a coronavirus-infected cell. Numerous intracellular and extracellular particles are present; virions are indicated by the arrowheads. FIG. 6B is a higher magnification electronmicrograph of the area seen at the arrow in FIG. 6A (rotated clockwise approximately) 90°. Bars: FIG. 6A, 1 μm; FIG. 6B, 100 nm.

FIGS. 7A-C illustrate the organization of the SARS-CoV genome. FIG. 7A is a diagram of the overall organization of the 29,727-nt SARS-CoV genomic RNA. The 72-nt leader sequence is represented as a small rectangle at the left-most end. ORFs1a and 1b, encoding the nonstructural polyproteins, and those ORFs encoding the S, E, M, and N structural proteins, are indicated. Vertical position of the boxes indicates the phase of the reading frame (phase 1 for proteins above the line, phase two for proteins on the line and phase three for proteins below the line). FIG. 7B is an expanded view of the structural protein encoding region and predicted mRNA transcripts. Known structural protein encoding regions (dark grey boxes) and regions and reading frames for potential products X1-X5 (light gray boxes) are indicated. Lengths and map locations of the 3'-coterminal mRNAs expressed by the SARS-CoV are indicated, as predicted by identification of conserved transcriptional regulatory sequences. FIG. 7C is a digitized image of a nylon membrane showing Northern blot analysis of SARS-CoV mRNAs. Poly (A)+ RNA from infected Vero E6 cells was separated on a formaldehyde-agarose gel, transferred to a nylon membrane, and hybridized with a digoxigenin-labeled riboprobe overlapping the 3'-untranslated region. Signals were visualized by chemiluminescence. Sizes of the SARS-CoV mRNAs were calculated by extrapolation from a log-linear fit of the molecular mass marker. Lane 1, SARS-CoV mRNA; lane 2, Vero E6 cell mRNA; lane 3, molecular mass marker, sizes in kB.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 shows the nucleic acid sequence of the SARS-CoV genome.

SEQ ID NO: 2 shows the amino acid sequence of the SARS-CoV polyprotein 1a (encoded by nucleic acid 265 to nucleic acid 13,398 of SEQ ID NO: 1).

SEQ ID NO: 3 shows the amino acid sequence of the SARS-CoV polyprotein 1b (encoded by nucleic acid 13,398 to 21,482 of SEQ ID NO: 1).

SEQ ID NO: 4 shows the amino acid sequence of the SARS-CoV S protein (encoded by nucleic acid 21,492 to 25,256 of SEQ ID NO: 1).

SEQ ID NO: 5 shows the amino acid sequence of the SARS-CoV X1 protein (encoded by nucleic acid 25,268 to 26,089 of SEQ ID NO: 1).

SEQ ID NO: 6 shows the amino acid sequence of the SARS-CoV X2 protein (encoded by nucleic acid 25,689 to 26,150 of SEQ ID NO: 1).

SEQ ID NO: 7 shows the amino acid sequence of the SARS-CoV E protein (encoded by nucleic acid 26,117 to 26,344 of SEQ ID NO: 1).

SEQ ID NO: 8 shows the amino acid sequence of the SARS-CoV M protein (encoded by nucleic acid 26,398 to 27,060 of SEQ ID NO: 1).

SEQ ID NO: 9 shows the amino acid sequence of the SARS-CoV X3 protein (encoded by nucleic acid 27,074 to 27,262 of SEQ ID NO: 1).

SEQ ID NO: 10 shows the amino acid sequence of the SARS-CoV X4 protein (encoded by nucleic acid 27,273 to 27,638 of SEQ ID NO: 1).

SEQ ID NO: 11 shows the amino acid sequence of the SARS-CoV X5 protein (encoded by nucleic acid 27,864 to 28,115 of SEQ ID NO: 1).

SEQ ID NO: 12 shows the amino acid sequence of the SARS-CoV N protein (encoded by nucleic acid 28,120 to 29,385 of SEQ ID NO: 1).

SEQ ID NOs: 13-15 show the nucleic acid sequence of several SARS-CoV-specific oligonucleotide primers.

SEQ ID NOs: 16-33 show the nucleic acid sequence of several oligonucleotide primers/probes used for real-time reverse transcription-polymerase chain reaction (RT-PCR) SARS-CoV assays.

SEQ ID NOs: 34-35 show the nucleic acid sequence of two degenerate primers designed to anneal to sites encoding conserved coronavirus amino acid motifs.

SEQ ID NOs: 36-38 show the nucleic acid sequence of several oligonucleotide primers/probes used as controls in real-time RT-PCR assays.

DETAILED DESCRIPTION OF SEVERAL EMBODIMENTS

I. Abbreviations

BAL: bronchoalveolar lavage
CPE: cytopathic effect
E: coronavirus transmembrane protein
ELISA: enzyme-linked immunosorbent assay
HE: coronavirus hemagglutinin-esterase protein
IFA: indirect fluorescent antibody
M: coronavirus membrane protein
N: coronavirus nucleoprotein
ORF: open reading frame
PCR polymerase chain reaction
RACE: 5' rapid amplification of cDNA ends
RT-PCR: reverse transcription-polymerase chain reaction
S: coronavirus spike protein
SARS: severe acute respiratory syndrome
SARS-CoV: severe acute respiratory syndrome-associated coronavirus
TRS: transcriptional regulatory sequence

II. Terms

Unless otherwise noted, technical terms are used according to conventional usage. Definitions of common terms in molecular biology may be found in Benjamin Lewin, Genes VII, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all nucleotide sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of this disclosure, the following explanations of specific terms are provided:

Adjuvant: A substance that non-specifically enhances the immune response to an antigen. Development of vaccine adjuvants for use in humans is reviewed in Singh et al. (*Nat. Biotechnol.* 17:1075-1081, 1999), which discloses that, at the time of its publication, aluminum salts and the MF59 microemulsion are the only vaccine adjuvants approved for human use.

Amplification: Amplification of a nucleic acid molecule (e.g., a DNA or RNA molecule) refers to use of a laboratory technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. The product of amplification can be characterized by such techniques as electrophoresis, restriction endonuclease cleavage patterns, oligonucleotide hybridization or ligation, and/or nucleic acid sequencing.

Other examples of amplification methods include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320,308; gap filling ligase chain reaction amplification, as disclosed in U.S. Pat. No. 5,427,930; and NASBA™ RNA transcription-free amplification, as disclosed in U.S. Pat. No. 6,025,134. An amplification method can be modified, including for example by additional steps or coupling the amplification with another protocol.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains As used herein, the term "antibodies" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies for use in the methods and devices of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In one embodiment, an antigen is a coronavirus antigen.

Binding or Stable Binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including functional or physical binding assays. Binding can be detected functionally by determining whether binding has an observable effect upon a biosynthetic process such as expression of a gene, DNA replication, transcription, translation, and the like.

Physical methods of detecting the binding of complementary strands of DNA or RNA are well known in the art, and include such methods as DNase I or chemical footprinting, gel shift and affinity cleavage assays, Northern blotting, Southern blotting, dot blotting, and light absorption detection procedures. For example, a method which is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target dissociate or melt.

The binding between an oligomer and its target nucleic acid is frequently characterized by the temperature ($T_m$) at which 50% of the oligomer is melted from its target. A higher $T_m$ means a stronger or more stable complex relative to a complex with a lower $T_m$.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Electrophoresis: Electrophoresis refers to the migration of charged solutes or particles in a liquid medium under the influence of an electric field. Electrophoretic separations are widely used for analysis of macromolecules. Of particular importance is the identification of proteins and nucleic acid sequences. Such separations can be based on differences in size and/or charge. Nucleotide sequences have a uniform charge and are therefore separated based on differences in size. Electrophoresis can be performed in an unsupported liquid medium (for example, capillary electrophoresis), but more commonly the liquid medium travels through a solid supporting medium. The most widely used supporting media are gels, for example, polyacrylamide and agarose gels.

Sieving gels (for example, agarose) impede the flow of molecules. The pore size of the gel determines the size of a molecule that can flow freely through the gel. The amount of time to travel through the gel increases as the size of the molecule increases. As a result, small molecules travel through the gel more quickly than large molecules and thus progress further from the sample application area than larger molecules, in a given time period. Such gels are used for size-based separations of nucleotide sequences.

Fragments of linear DNA migrate through agarose gels with a mobility that is inversely proportional to the $\log_{10}$ of their molecular weight. By using gels with different concentrations of agarose, different sizes of DNA fragments can be resolved. Higher concentrations of agarose facilitate separation of small DNAs, while low agarose concentrations allow resolution of larger DNAs.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Ausubel et al. *Short Protocols in Molecular Biology*, $4^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

Immune Stimulatory Composition: A term used herein to mean a composition useful for stimulating or eliciting a specific immune response (or immunogenic response) in a vertebrate. In some embodiments, the immunogenic response is protective or provides protective immunity, in that it enables the vertebrate animal to better resist infection with or disease progression from the organism against which the vaccine is directed.

Without wishing to be bound by a specific theory, it is believed that an immunogenic response may arise from the generation of an antibody specific to one or more of the epitopes provided in the immune stimulatory composition. Alternatively, the response may comprise a T-helper or cytotoxic cell-based response to one or more of the epitopes provided in the immune stimulatory composition. All three of these responses may originate from naïve or memory cells. One specific example of a type of immune stimulatory composition is a vaccine.

In some embodiments, an "effective amount" or "immunestimulatory amount" of an immune stimulatory composition is an amount which, when administered to a subject, is sufficient to engender a detectable immune response. Such a response may comprise, for instance, generation of an antibody specific to one or more of the epitopes provided in the immune stimulatory composition. Alternatively, the response may comprise a T-helper or CTL-based response to one or more of the epitopes provided in the immune stimulatory composition. All three of these responses may originate from naïve or memory cells. In other embodiments, a "protective effective amount" of an immune stimulatory composition is an amount which, when administered to a subject, is sufficient to confer protective immunity upon the subject.

Inhibiting or Treating a Disease: Inhibiting the full development of a disease or condition, for example, in a subject who is at risk for a disease such as SARS. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated: An "isolated" microorganism (such as a virus, bacterium, fungus, or protozoan) has been substantially separated or purified away from microorganisms of different types, strains, or species. Microorganisms can be isolated by a variety of techniques, including serial dilution and culturing.

An "isolated" biological component (such as a nucleic acid molecule, protein or organelle) has been substantially separated or purified away from other biological components in the cell of the organism in which the component naturally occurs, such as other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids or proteins, or fragments thereof.

Label: A detectable compound or composition that is conjugated directly or indirectly to another molecule to facilitate detection of that molecule. Specific, non-limiting examples of labels include fluorescent tags, enzymatic linkages, and radioactive isotopes.

Nucleic Acid Molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages.

Oligonucleotide: A nucleic acid molecule generally comprising a length of 300 bases or fewer. The term often refers to single-stranded deoxyribonucleotides, but it can refer as well to single- or double-stranded ribonucleotides, RNA:DNA hybrids and double-stranded DNAs, among others. The term "oligonucleotide" also includes oligonucleosides (that is, an oligonucleotide minus the phosphate) and any other organic base polymer. In some examples, oligonucleotides are about 10 to about 90 bases in length, for example, 12, 13, 14, 15, 16, 17, 18, 19 or 20 bases in length. Other oligonucleotides are about 25, about 30, about 35, about 40, about 45, about 50, about 55, about 60 bases, about 65 bases, about 70 bases, about 75 bases or about 80 bases in length. Oligonucleotides may be single-stranded, for example, for use as probes or primers, or may be double-stranded, for example, for use in the construction of a mutant gene. Oligonucleotides can be either sense or anti-sense oligonucleotides. An oligonucleotide can be modified as discussed above in reference to nucleic acid molecules. Oligonucleotides can be obtained from existing nucleic acid sources (for example, genomic or cDNA), but can also be synthetic (for example, produced by laboratory or in vitro oligonucleotide synthesis).

Open Reading Frame (ORF): A series of nucleotide triplets (codons) coding for amino acids without any internal termination codons. These sequences are usually translatable into a peptide/polypeptide/protein/polyprotein.

Operably Linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame. If introns are present, the operably linked DNA sequences may not be contiguous.

Pharmaceutically Acceptable Carriers: The pharmaceutically acceptable carriers useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compounds or molecules, such as one or more SARS-CoV nucleic acid molecules, proteins or antibodies that bind these proteins, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Probes and Primers: A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (ed.), Molecular Cloning: A Laboratory Manual, $2^{nd}$ ed., vol. 1-3, Cold Spring Harbor Laboratory Press, Cold Spring Harbor, N.Y., 1989 and Ausubel et al. *Short Protocols in Molecular Biology*, 4th ed., John Wiley & Sons, Inc., 1999.

Primers are short nucleic acid molecules, for instance DNA oligonucleotides 10 nucleotides or more in length, for example that hybridize to contiguous complementary nucleotides or a sequence to be amplified. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example, by the PCR or other nucleic-acid amplification methods known in the art, as described above.

Methods for preparing and using nucleic acid probes and primers are described, for example, in Sambrook et al. (ed.), *Molecular Cloning: A Laboratory Manual*, 2nd ed., vol. 1-3, Cold Spring Harbor Laboratory Press, Cold Spring Harbor, N.Y., 1989; Ausubel et al. *Short Protocols in Molecular Biology*, 4th ed., John Wiley & Sons, Inc., 1999; and Innis et al. *PCR Protocols, A Guide to Methods and Applications*, Academic Press, Inc., San Diego, Calif., 1990. Amplification primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, in order to obtain greater specificity, probes and primers can be selected that comprise at least 20, 25, 30, 35, 40, 45, 50 or more consecutive nucleotides of a target nucleotide sequence.

Protein: A biological molecule, particularly a polypeptide, expressed by a gene and comprised of amino acids. A "polyprotein" is a protein that, after synthesis, is cleaved to produce several functionally distinct polypeptides.

Purified: The term "purified" does not require absolute purity; rather, it is intended as a relative term. Thus, for example, a purified protein preparation is one in which the subject protein is more pure than in its natural environment within a cell. Generally, a protein preparation is purified such that the protein represents at least 50% of the total protein content of the preparation.

Recombinant Nucleic Acid: A sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques such as those described in Sambrook et al. (ed.), *Molecular Cloning: A Laboratory Manual*, 2nd ed., vol. 1-3, Cold Spring Harbor Laboratory Press, Cold Spring Harbor, N.Y., 1989. The term recombinant includes nucleic acids that have been altered solely by addition, substitution, or deletion of a portion of the nucleic acid.

Sample: A portion, piece, or segment that is representative of a whole. This term encompasses any material, including for instance samples obtained from an animal, a plant, or the environment.

An "environmental sample" includes a sample obtained from inanimate objects or reservoirs within an indoor or outdoor environment. Environmental samples include, but are not limited to: soil, water, dust, and air samples; bulk samples, including building materials, furniture, and landfill contents; and other reservoir samples, such as animal refuse, harvested grains, and foodstuffs.

A "biological sample" is a sample obtained from a plant or animal subject. As used herein, biological samples include all samples useful for detection of viral infection in subjects, including, but not limited to: cells, tissues, and bodily fluids, such as blood; derivatives and fractions of blood (such as serum); extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; bone marrow aspirates; BAL; saliva; cervical swabs; vaginal swabs; and oropharyngeal wash.

Sequence Identity The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.*, 2:482, 1981); Needleman and Wunsch (*J. Mol. Biol.*, 48:443, 1970); Pearson and Lipman (*Proc. Natl. Acad. Sci.*, 85:2444, 1988); Higgins and Sharp (*Gene*, 73:237-44, 1988); Higgins and Sharp (*CABIOS*, 5:151-53, 1989); Corpet et al. (*Nuc. Acids Res.*, 16:10881-90, 1988); Huang et al. (*Comp. Appls Biosci.*, 8:155-65, 1992); and Pearson et al. (*Meth. Mol. Biol.*, 24:307-31, 1994). Altschul et al. (*Nature Genet.*, 6:119-29, 1994) presents a detailed consideration of sequence alignment methods and homology calculations.

The alignment tools ALIGN (Myers and Miller, *CABIOS* 4:11-17, 1989) or LFASTA (Pearson and Lipman, 1988) may be used to perform sequence comparisons (Internet Program© 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at the NCSA website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.*, 215:403-10, 1990; Gish and States, *Nature Genet.*, 3:266-72, 1993; Madden et al., *Meth. Enzymol.*, 266:131-41, 1996; Altschul et al., *Nucleic Acids Res.*, 25:3389-402, 1997; and Zhang and Madden, *Genome Res.*, 7:649-56, 1997.

Orthologs (equivalent to proteins of other species) of proteins are in some instances characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of one or both binding domains of the disclosed fusion proteins.

When significantly less than the entire sequence is being compared for sequence identity, homologous sequences will typically possess at least 80% sequence identity over short windows of 10-20, and may possess sequence identities of at least 85%, at least 90%, at least 95%, or at least 99% depending on their similarity to the reference sequence. Sequence identity over such short windows can be determined using LFASTA; methods are described at the NCSA website. One of skill in the art will appreciate that these sequence identity ranges are provided for guidance only; it is entirely possible that strongly significant homologs could be obtained that fall outside of the ranges provided. Similar homology concepts apply for nucleic acids as are described for protein.

An alternative indication that two nucleic acid molecules are closely related is that the two molecules hybridize to each other under stringent conditions. Representative hybridization conditions are discussed above.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Specific Binding Agent: An agent that binds substantially only to a defined target. Thus a protein-specific binding agent binds substantially only the defined protein, or to a specific region within the protein. As used herein, a protein-specific binding agent includes antibodies and other agents that bind substantially to a specified polypeptide. The antibodies may be monoclonal or polyclonal antibodies that are specific for the polypeptide, as well as immunologically effective portions ("fragments") thereof.

The determination that a particular agent binds substantially only to a specific polypeptide may readily be made by using or adapting routine procedures. One suitable in vitro assay makes use of the Western blotting procedure (described in many standard texts, including Harlow and Lane, *Using Antibodies: A Laboratory Manual*, CSHL, New York, 1999).

Transformed: A "transformed" cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Virus: Microscopic infectious organism that reproduces inside living cells. A virus typically consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

"Coronaviruses" are large, enveloped, RNA viruses that cause respiratory and enteric diseases in humans and other animals. Coronavirus genomes are non-segmented, single-stranded, positive-sense RNA, approximately 27-31 kb in length. Genomes have a 5' methylated cap and 3' poly-A tail, and function directly as mRNA. Host cell entry occurs via endocytosis and membrane fusion, and replication occurs in the cytoplasm. Initially, the 5' 20 kb of the positive-sense genome is translated to produce a viral polymerase, which then produces a full-length negative-sense strand used as a template to produce subgenomic mRNA as a "nested set" of transcripts. Assembly occurs by budding into the golgi apparatus, and particles are transported to the surface of the cell and released.

III. Overview of Several Embodiments

A newly isolated human coronavirus (SARS-CoV) is disclosed herein. The entire genomic nucleic acid sequence of this virus is also provided herein. Also disclosed are the nucleic acid sequences of the SARS-CoV ORFs, and the polypeptide sequences encoded by these ORFs. Pharmaceutical and immune stimulatory compositions are also disclosed that include one or more SARS-CoV viral nucleic acids, polypeptides encoded by these viral nucleic acids and antibodies that bind to a SARS-CoV polypeptide or SARS-CoV polypeptide fragment.

In one embodiment, a method is provided for detecting the presence of SARS-CoV in a sample. This method includes contacting the sample with a pair of nucleic acid primers that hybridize to a SARS-CoV nucleic acid, wherein at least one primer is 5'-end labeled with a reporter dye, amplifying the SARS-CoV nucleic acid or a fragment thereof from the sample utilizing the pair of nucleic acid primers, electrophoresing the amplified products, and detecting the 5'-end labeled reporter dye, thereby detecting a SARS-CoV. In a specific, non-limiting example, the amplification utilizes RT-PCR. In a further specific example of the provided method, at least one of the nucleic acid primers that hybridize to a SARS-CoV nucleic acid includes a sequence as set forth in any one of SEQ ID NOs: 13-15.

In another example of the provided method, detecting the presence of SARS-CoV in a sample includes contacting the sample with a pair of nucleic acid primers that hybridize to a SARS-CoV nucleic acid, amplifying the SARS-CoV nucleic acid or a fragment thereof from the sample utilizing the pair of nucleic acid primers, adding to the amplified SARS-CoV nucleic acid or the fragment thereof a TaqMan SARS-CoV probe that hybridizes to the SARS-CoV nucleic acid, wherein the TaqMan SARS-CoV probe is labeled with a 5'-reporter dye and a 3'-quencher dye, performing one or more additional rounds of amplification, and detecting fluorescence of the 5'-reporter dye, thereby detecting a SARS-CoV. In a specific, non-limiting example, the amplification utilizes RT-PCR. In a further specific example of the provided method, at least one of the nucleic acid primers that hybridize to a SARS-CoV nucleic acid and/or the TaqMan SARS-CoV probe that hybridizes to the SARS-CoV nucleic acid includes a sequence as set forth in any one of SEQ ID NOs: 16-33.

In another embodiment, a method is provided for detecting a SARS-CoV in a biological sample that contains antibodies. This method includes contacting the biological sample with a SARS-CoV-specific antigen, wherein the antigen includes a SARS-CoV organism and determining whether a binding reaction occurs between the SARS-CoV-specific antigen and an antibody in the biological sample if such is present, thereby detecting SARS-CoV.

In a further embodiment, a method is provided for detecting a SARS-CoV in a biological sample that contains polypeptides and/or fragments thereof. This method includes contacting the biological sample with a SARS-CoV-specific antibody and determining whether a binding reaction occurs between the SARS-CoV-specific antibody and a SARS-CoV polypeptide or fragment thereof in the biological sample if such is present, thereby detecting SARS-CoV. In a specific, non-limiting example, determining whether a binding reaction occurs between the SARS-CoV-specific antibody and a SARS-CoV polypeptide or fragment thereof is carried out in situ or in a tissue sample. In a further specific example, determining whether a binding reaction occurs between the SARS-CoV-specific antibody and a SARS-CoV polypeptide or fragment thereof includes an immunohistochemical assay.

An additional embodiment includes a kit for detecting a SARS-CoV in a sample, including a pair of nucleic acid primers that hybridize under stringent conditions to a SARS-CoV nucleic acid, wherein one primer is 5'-end labeled with a reporter dye. In a specific, non-limiting example, at least one of the nucleic acid primers that hybridize to a SARS-CoV nucleic acid includes a sequence as set forth in any one of SEQ ID NOs: 13-15.

Another example of the provided kit includes a pair of nucleic acid primers that hybridize under high stringency conditions to a SARS-CoV nucleic acid and a TaqMan SARS-CoV probe that hybridizes to the SARS-CoV nucleic acid, wherein the TaqMan SARS-CoV probe is labeled with a 5'-reporter dye and a 3'-quencher dye. In a specific, non-limiting example, at least one of the nucleic acid primers that hybridize to a SARS-CoV nucleic acid and/or the TaqMan SARS-CoV probe that hybridizes to the SARS-CoV nucleic acid includes a sequence as set forth in any one of SEQ ID NOs: 16-33.

Also disclosed herein is a composition including an isolated SARS-CoV organism. In one embodiment, the isolated SARS-CoV organism is an inactive isolated SARS-CoV organism. In another embodiment, the composition includes at least one component selected from the group consisting of pharmaceutically acceptable carriers, adjuvants and combinations of two or more thereof. In yet another embodiment, the composition is introduced into a subject, thereby eliciting an immune response against a SARS-CoV antigenic epitope in a subject.

IV. SARS-CoV Nucleotide and Amino Acid Sequences

The current disclosure provides an isolated SARS-CoV genome, isolated SARS-CoV polypeptides, and isolated nucleic acid molecules encoding the same. In one embodiment, the isolated SARS-CoV genome has a sequence as shown in SEQ ID NO: 1 or an equivalent thereof. Polynucleotides encoding a SARS-CoV polypeptide (encoded by an ORF from within the genome) are also provided, and are termed SARS-CoV nucleic acid molecules. These nucleic acid molecules include DNA, cDNA and RNA sequences which encode a SARS-CoV polypeptide. Specific, non-limiting examples of a SARS-CoV nucleic acid molecule encoding an ORF are nucleic acid 265 to nucleic acid 13,398 of SEQ ID NO: 1 (encoding SARS-CoV 1a, SEQ ID NO: 2), nucleic acid 13,398 to 21,482 of SEQ ID NO: 1 (encoding SARS-CoV 1b, SEQ ID NO: 3), nucleic acid 21,492 to 25,256 of SEQ ID NO: 1 (encoding SARS-CoV S, SEQ ID NO: 4), nucleic acid 25,268 to 26,089 of SEQ ID NO: 1 (encoding SARS-CoV X1, SEQ ID NO: 5), nucleic acid 25,689 to 26,150 of SEQ ID NO: 1 (encoding SARS-CoV X2, SEQ ID NO: 6), nucleic acid 26,117 to 26,344 of SEQ ID NO: 1 (encoding SARS-CoV E, SEQ ID NO: 7), nucleic acid 26,398 to 27,060 of SEQ ID NO: 1 (encoding SARS-CoV M, SEQ ID NO: 8), nucleic acid 27,074 to 27,262 of SEQ ID NO: 1 (encoding SARS-CoV X3, SEQ ID NO: 9), nucleic acid 27,273 to 27,638 of SEQ ID NO: 1 (encoding SARS-CoV X4, SEQ ID NO: 10), nucleic acid 27,864 to 28,115 of SEQ ID NO: 1 (encoding SARS-CoV X5, SEQ ID NO: 11), and nucleic acid 28,120 to 29,385 of SEQ ID NO: 1 (encoding SARS-CoV N, SEQ ID NO: 12).

Oligonucleotide primers and probes derived from the SARS-CoV genome (SEQ ID NO: 1) are also encompassed within the scope of the present disclosure. Such oligonucleotide primers and probes may comprise a sequence of at least about 15 consecutive nucleotides of the SARS-CoV nucleic acid sequence, such as at least about 20, 25, 30, 35, 40, 45, or 50 or more consecutive nucleotides. These primers and probes may be obtained from any region of the disclosed SARS-CoV genome (SEQ ID NO: 1), including particularly from any of the ORFs disclosed herein. Specific, non-limiting examples of oligonucleotide primers derived from the SARS-CoV genome (SEQ ID NO: 1) include: Cor-p-F2 (SEQ ID NO: 13), Cor-p-F3 (SEQ ID NO: 14), Cor-p-R1 (SEQ ID NO: 15), SARS1-F (SEQ ID NO: 16), SARS1—R (SEQ ID NO: 17), SARS2-F (SEQ ID NO: 19), SARS2—R (SEQ ID NO: 20), SARS3-F (SEQ ID NO: 22), SARS3—R (SEQ ID NO: 23), N3-F (SEQ ID NO: 25), N3-R (SEQ ID NO: 26), 3'NTR-F (SEQ ID NO: 28), 3'NTR-R (SEQ ID NO: 29), M-F (SEQ ID NO: 31), and M-R (SEQ ID NO: 32). Specific, non-limiting examples of oligonucleotide probes derived from the SARS-CoV genome (SEQ ID NO: 1) include: SARS1-P (SEQ ID NO: 18), SARS2-P (SEQ ID NO: 21), SARS3-P (SEQ ID NO: 24), N3-P (SEQ ID NO: 27), 3'NTR-P (SEQ ID NO: 30), and M-P (SEQ ID NO: 33).

Nucleic acid molecules encoding a SARS-CoV polypeptide can be operatively linked to regulatory sequences or elements. Regulatory sequences or elements include, but are not limited to promoters, enhancers, transcription terminators, a start codon (for example, ATG), stop codons, and the like.

Additionally, nucleic acid molecules encoding a SARS-CoV polypeptide can be inserted into an expression vector. Specific, non-limiting examples of vectors include, plasmids, bacteriophages, cosmids, animal viruses and yeast artificial chromosomes (YACs) (Burke et al., *Science* 236:806-12, 1987). Such vectors may then be introduced into a variety of hosts including somatic cells, and simple or complex organisms, such as bacteria, fungi (Timberlake and Marshall, *Science* 244:1313-17, 1989), invertebrates, plants (Gasser et al., *Plant Cell* 1:15-24, 1989), and animals (Pursel et al., *Science* 244:1281-88, 1989).

Transformation of a host cell with an expression vector carrying a nucleic acid molecule encoding a SARS-CoV polypeptide may be carried out by conventional techniques, as are well known to those skilled in the art. By way of example, where the host is prokaryotic, such as *E. coli*, competent cells that are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, methods of transfection of DNA, such as calcium phosphate coprecipitates, conventional mechanical procedures such as microinjection, electroporation, insertion of a plasmid encased in liposomes, or virus vectors, may be used. Eukaryotic cells can also be cotransformed with SARS-CoV nucleic acid molecules, and a second foreign DNA molecule encoding a selectable phenotype, such as the herpes simplex thymidine kinase gene. Another method is to use a eukaryotic viral vector, such as simian virus 40 or bovine papilloma virus, to transiently infect or transform eukaryotic cells and express the protein (see, for example, *Eukaryotic Viral Vectors,* Cold Spring Harbor Laboratory, Gluzman ed., 1982).

The SARS-CoV polypeptides of this disclosure include proteins encoded by any of the ORFs disclosed herein, and equivalents thereof. Specific, non-limiting examples of SARS-CoV proteins are provided in SEQ ID NOs: 2-12. Fusion proteins are also contemplated that include a heterologous amino acid sequence chemically linked to a SARS-CoV polypeptide. Exemplary heterologous sequences include short amino acid sequence tags (such as six histidine residues), as well as a fusion of other proteins (such as c-myc or green fluorescent protein fusions). Epitopes of the SARS-CoV proteins, that are recognized by an antibody or that bind the major histocompatibility complex, and can be used to induce a SARS-CoV-specific immune response, are also encompassed by this disclosure.

Methods for expressing large amounts of protein from a cloned gene introduced into *E. coli* may be utilized for the purification and functional analysis of proteins. For example, fusion proteins consisting of amino terminal peptides encoded by a portion of the *E. coli* lacZ or trpE gene linked to SARS-CoV proteins may be used to prepare polyclonal and monoclonal antibodies against these proteins.

Intact native protein may also be produced in *E. coli* in large amounts for functional studies. Methods and plasmid vectors for producing fusion proteins and intact native proteins in bacteria are described by Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989. Such fusion proteins may be made in large amounts, are easy to purify, and can be used to elicit antibody response. Native proteins can be produced in bacteria by placing a strong, regulated promoter and an efficient ribosome-binding site upstream of the cloned gene. If low levels of protein are produced, additional steps may be taken to increase protein production; if high levels of protein are produced, purification is relatively easy. Suitable methods are presented by Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989, and are well known in the art. Often, proteins expressed at high levels are found in insoluble inclusion bodies. Methods for extracting proteins from these aggregates are described by Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989.

Isolation and purification of recombinantly expressed proteins may be carried out by conventional means including preparative chromatography and immunological separations. Additionally, the proteins can be chemically synthesized by any of a number of manual or automated methods of synthesis known in the art.

V. Specific Binding Agents

The disclosure provides specific binding agents that bind to SARS-CoV polypeptides disclosed herein. The binding agent may be useful for purifying and detecting the polypeptides, as well as for detection and diagnosis of SARS-CoV. Examples of the binding agents are a polyclonal or monoclonal antibody, and fragments thereof, that bind to any of the SARS-CoV polypeptides disclosed herein.

Monoclonal or polyclonal antibodies may be raised to recognize a SARS-CoV polypeptide described herein, or a fragment or variant thereof. Optimally, antibodies raised against these polypeptides would specifically detect the polypeptide with which the antibodies are generated. That is, antibodies raised against a specific SARS-CoV polypeptide will recognize and bind that polypeptide, and will not substantially recognize or bind to other polypeptides or antigens. The determination that an antibody specifically binds to a target polypeptide is made by any one of a number of standard immunoassay methods; for instance, the Western blotting technique (Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989).

Substantially pure SARS-CoV recombinant polypeptide antigens suitable for use as immunogen may be isolated from the transformed cells described above, using methods well known in the art. Monoclonal or polyclonal antibodies to the antigens may then be prepared.

Monoclonal antibodies to the polypeptides can be prepared from murine hybridomas according to the classic method of Kohler & Milstein (*Nature* 256:495-97, 1975), or a derivative method thereof. Briefly, a mouse is repetitively inoculated with a few micrograms of the selected protein immunogen (for example, a polypeptide comprising at least one SARS-CoV-specific epitope, a portion of a polypeptide comprising at least one SARS-CoV-specific epitope, or a synthetic peptide comprising at least one SARS-CoV-specific epitope) over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Meth. Enzymol.,* 70:419-39, 1980), or a derivative method thereof. Selected positive clones can be expanded and their monoclonal antibody product harvested for use. Detailed procedures for monoclonal antibody production are described in Harlow and Lane, *Using Antibodies: A Laboratory Manual,* CSHL, New York, 1999.

Polyclonal antiserum containing antibodies can be prepared by immunizing suitable animals with a polypeptide comprising at least one SARS-CoV-specific epitope, a portion of a polypeptide comprising at least one SARS-CoV-specific epitope, or a synthetic peptide comprising at least one SARS-CoV-specific epitope, which can be unmodified or modified, to enhance immunogenicity.

Effective antibody production (whether monoclonal or polyclonal) is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.,* 33:988-91, 1971).

Booster injections can be given at regular intervals, and antiserum harvested when the antibody titer thereof, as determined semi-quantitatively, for example, by double immunodiffusion in agar against known concentrations of the antigen, begins to fall. See, for example, Ouchterlony et al., *Handbook of Experimental Immunology,* Wier, D. (ed.), Chapter 19, Blackwell, 1973. A plateau concentration of antibody is usually in the range of 0.1 to 0.2 mg/ml of serum (about 12 µM). Affinity of the antisera for the antigen is determined by preparing competitive binding curves, as described, for example, by Fisher (*Manual of Clinical Immunology*, Ch. 42, 1980).

Antibody fragments may be used in place of whole antibodies and may be readily expressed in prokaryotic host cells. Methods of making and using immunologically effective portions of monoclonal antibodies, also referred to as "antibody fragments," are well known and include those described in Better & Horowitz, *Methods Enzymol.* 178:476-96, 1989; Glockshuber et al., *Biochemistry* 29:1362-67, 1990; and U.S. Pat. Nos. 5,648,237 (Expression of Functional Antibody Fragments); 4,946,778 (Single Polypeptide Chain Binding Molecules); and 5,455,030 (Immunotherapy Using Single Chain Polypeptide Binding Molecules), and references cited therein. Conditions whereby a polypeptide/binding agent complex can form, as well as assays for the detection of the formation of a polypeptide/binding agent complex and quantitation of binding affinities of the binding agent and polypeptide, are standard in the art. Such assays can include, but are not limited to, Western blotting, immunoprecipitation, immunofluorescence, immunocytochemistry, immunohistochemistry, fluorescence activated cell sorting (FACS), fluorescence in situ hybridization (FISH), immunomagnetic assays, ELISA, ELISPOT (Coligan et al., *Current Protocols in Immunology*, Wiley, NY, 1995), agglutination assays, flocculation assays, cell panning, and the like, as are well known to one of skill in the art.

Binding agents of this disclosure can be bound to a substrate (for example, beads, tubes, slides, plates, nitrocellulose sheets, and the like) or conjugated with a detectable moiety, or both bound and conjugated. The detectable moieties contemplated for the present disclosure can include, but are not limited to, an immunofluorescent moiety (for example, fluorescein, rhodamine), a radioactive moiety (for example, $^{32}P$, $^{125}I$, $^{35}S$), an enzyme moiety (for example, horseradish peroxidase, alkaline phosphatase), a colloidal gold moiety, and a biotin moiety. Such conjugation techniques are standard in the art (for example, see Harlow and Lane, *Using Antibodies: A Laboratory Manual*, CSHL, New York, 1999; Yang et al., *Nature*, 382:319-24, 1996).

VI. Detection and Diagnosis of SARS-CoV

A. Nucleic Acid Based Methods of Detection and Diagnosis

A major application of the SARS-CoV sequence information presented herein is in the area of detection and diagnostic testing for SARS-CoV infection. Methods for screening a subject to determine if the subject has been or is currently infected with SARS-CoV are disclosed herein.

One such method includes providing a sample, which sample includes a nucleic acid such as DNA or RNA, and providing an assay for detecting in the sample the presence of a SARS-CoV nucleic acid molecule. Suitable samples include all biological samples useful for detection of viral infection in subjects, including, but not limited to, cells, tissues (for example, lung and kidney), bodily fluids (for example, blood, serum, urine, saliva, sputum, and cerebrospinal fluid), bone marrow aspirates, BAL, and oropharyngeal wash. Additional suitable samples include all environmental samples useful for detection of viral presence in the environment, including, but not limited to, a sample obtained from inanimate objects or reservoirs within an indoor or outdoor environment. The detection in the sample of a SARS-CoV nucleic acid molecule may be performed by a number of methodologies, non-limiting examples of which are outlined below.

In one embodiment, detecting in the sample the presence of a SARS-CoV nucleic acid molecule includes the amplification of a SARS-CoV nucleic acid sequence (or a fragment thereof). Any nucleic acid amplification method can be used. In one specific, non-limiting example, PCR is used to amplify the SARS-CoV nucleic acid sequence(s). In another non-limiting example, RT-PCR can be used to amplify the SARS-CoV nucleic acid sequences. In an additional non-limiting example, transcription-mediated amplification can be used to amplify the SARS-CoV nucleic acid sequences.

In some embodiments, a pair of SARS-CoV-specific primers are utilized in the amplification reaction. One or both of the primers can be end-labeled (for example, radiolabeled, fluoresceinated, or biotinylated). In one specific, non-limiting example, at least one of the primers is 5'-end labeled with the reporter dye 6-carboxyfluorescein (6-FAM). The pair of primers includes an upstream primer (which binds 5' to the downstream primer) and a downstream primer (which binds 3' to the upstream primer). In one embodiment, either the upstream primer or the downstream primer is labeled. Specific, non-limiting examples of SARS-CoV-specific primers include, but are not limited to: Cor-p-F2 (SEQ ID NO: 13), Cor-p-F3 (SEQ ID NO: 14), Cor-p-R1 (SEQ ID NO: 15), SARS1-F (SEQ ID NO: 16), SARS1-R (SEQ ID NO: 17), SARS2-F (SEQ ID NO: 19), SARS2-R (SEQ ID NO: 20), SARS3-F (SEQ ID NO: 22), SARS3R (SEQ ID NO: 23), N3-F (SEQ ID NO: 25), N3-R (SEQ ID NO: 26), 3'NTR-F (SEQ ID NO: 28), 3'NTR-R (SEQ ID NO: 29), M-F (SEQ ID NO: 31), and M-R (SEQ ID NO: 32). Additional primer pairs can be generated, for instance, to amplify any of the specific ORFs described herein, using well known primer design principles and methods.

In one specific, non-limiting example, electrophoresis is used to detect amplified SARS-CoV-specific sequences. Electrophoresis can be automated using many methods well know in the art. In one embodiment, a genetic analyzer is used, such as an ABI 3100 Prism Genetic Analyzer (PE Applied Biosystems, Foster City, Calif.), wherein the bands are analyzed using GeneScan software (PE Applied Biosystems, Foster City, Calif.).

In another specific, non-limiting example, hybridization assays are used to detect amplified SARS-CoV-specific sequences using distinguishing oligonucleotide probes. Such probes include "TaqMan" probes. TaqMan probes consist of an oligonucleotide with a reporter at the 5'-end and a quencher at the 3'-end. In one specific, non-limiting example, the reporter is 6-FAM and the quencher is Blackhole Quencher (Biosearch Tech., Inc., Novato, Calif.). When the probe is intact, the proximity of the reporter to the quencher results in suppression of reporter fluorescence, primarily by fluorescence resonance energy transfer. If the target of interest is present, the TaqMan probe specifically hybridizes between the forward and reverse primer sites during the PCR annealing step. In the process of PCR elongation, the 5'-3' nucleolytic activity of the Taq DNA polymerase cleaves the hybridized probe between the reporter and the quencher. The probe fragments are then displaced from the target, and polymerization of the strand continues. Taq DNA polymerase does not cleave non-hybridized probe, and cleaves the hybridized probe only during polymerization. The 3'-end of the probe is blocked to prevent extension of the probe during PCR. The 5'-3' nuclease cleavage of the hybridized probe occurs in every cycle and does not interfere with the exponential accumulation of PCR product. Accumulation of PCR products is detected directly by monitoring the increase in fluorescence of the released reporter. The increase in fluorescence signal is detected only if the target sequence is complementary to the probe and is amplified during PCR. Therefore, non-specific amplification is not detected. SARS-CoV-specific TaqMan probes of the present disclosure include, but are not limited to: SARS1-P (SEQ ID NO: 18), SARS2-P (SEQ ID NO: 21), SARS3-P (SEQ ID NO: 24), N3-P (SEQ ID NO: 27), 3'NTR-P (SEQ ID NO: 30), and M-P (SEQ ID NO: 33), and hybridization assays include, but are not limited to, a real-time RT-PCR assay.

B. Protein Based Methods of Detection and Diagnosis

The present disclosure further provides methods of detecting a SARS-CoV antigen in a sample, and/or diagnosing SARS-CoV infection in a subject by detecting a SARS-CoV antigen. Examples of such methods comprise contacting the sample with a SARS-CoV-specific binding agent under conditions whereby an antigen/binding agent complex can form; and detecting formation of the complex, thereby detecting SARS-CoV antigen in a sample and/or diagnosing SARS-CoV infection in a subject. It is contemplated that at least certain antigens will be on an intact SARS-CoV virion, will be a SARS-CoV-encoded protein displayed on the surface of a SARS-CoV-infected cell expressing the antigen, or will be a fragment of the antigen. Contemplated samples subject to analysis by these methods can comprise any sample, such as a clinical sample, useful for detection of viral infection in a subject.

Methods for detecting antigens in a sample are discussed, for example, in Ausubel et al. *Short Protocols in Molecular Biology*, 4$^{th}$ ed., John Wiley & Sons, Inc., 1999. Enzyme immunoassays such as IFA, ELISA and immunoblotting can be readily adapted to accomplish the detection of SARS-CoV antigens according to the methods of this disclosure. An ELISA method effective for the detection of soluble SARS-CoV antigens is the direct competitive ELISA. This method is most useful when a specific SARS-CoV antibody and purified SARS-CoV antigen are available. Briefly: 1) coat a substrate (for example, a microtiter plate) with a sample suspected of containing a SARS-CoV antigen; 2) contact the bound SARS-CoV antigen with a SARS-CoV-specific antibody bound to a detectable moiety (for example, horseradish peroxidase enzyme or alkaline phosphatase enzyme); 3) add purified inhibitor SARS-CoV antigen; 4) contact the above with the substrate for the enzyme; and 5) observe/measure inhibition of color change or fluorescence and quantitate antigen concentration (for example, using a microtiter plate reader).

An additional ELISA method effective for the detection of soluble SARS-CoV antigens is the antibody-sandwich ELISA. This method is frequently more sensitive in detecting antigen than the direct competitive ELISA method. Briefly: 1) coat a substrate (for example, a microtiter plate) with a SARS-CoV-specific antibody; 2) contact the bound SARS-CoV antibody with a sample suspected of containing a SARS-CoV antigen; 3) contact the above with SARS-CoV-specific antibody bound to a detectable moiety (for example, horseradish peroxidase enzyme or alkaline phosphatase enzyme); 4) contact the above with the substrate for the enzyme; and 5) observe/measure color change or fluorescence and quantitate antigen concentration (for example, using a microtiter plate reader).

An ELISA method effective for the detection of cell-surface SARS-CoV antigens is the direct cellular ELISA. Briefly, cells suspected of exhibiting a cell-surface SARS-CoV antigen are fixed (for example, using glutaraldehyde) and incubated with a SARS-CoV-specific antibody bound to a detectable moiety (for example, horseradish peroxidase enzyme or alkaline phosphatase enzyme). Following a wash to remove unbound antibody, substrate for the enzyme is added and color change or fluorescence is observed/measured.

The present disclosure further provides methods of detecting a SARS-CoV-reactive antibody in a sample, and/or diagnosing SARS-CoV infection in a subject by detecting a SARS-CoV-reactive antibody. Examples of such methods comprise contacting the sample with a SARS-CoV polypeptide of this disclosure under conditions whereby a polypeptide/antibody complex can form; and detecting formation of the complex, thereby detecting SARS-CoV antibody in a sample and/or diagnosing SARS-CoV infection in a subject. Contemplated samples subject to analysis by these methods can comprise any sample, such as a clinical sample, as described herein as being useful for detection of viral infection in a subject.

Methods for detecting antibodies in a sample are discussed, for example, in Ausubel et al. *Short Protocols in Molecular Biology*, 4$^{th}$ ed., John Wiley & Sons, Inc., 1999. Enzyme immunoassays such as IFA, ELISA and immunoblotting can be readily adapted to accomplish the detection of SARS-CoV antibodies according to the methods of this disclosure. An ELISA method effective for the detection of specific SARS-CoV antibodies is the indirect ELISA method. Briefly: 1) bind a SARS-CoV polypeptide to a substrate (for example, a microtiter plate); 2) contact the bound polypeptide with a sample suspected of containing SARS-CoV antibody; 3) contact the above with a secondary antibody bound to a detectable moiety which is reactive with the bound antibody (for example, horseradish peroxidase enzyme or alkaline phosphatase enzyme); 4) contact the above with the substrate for the enzyme; and 5) observe/measure color change or fluorescence.

Another immunologic technique that can be useful in the detection of SARS-CoV antibodies uses monoclonal antibodies for detection of antibodies specifically reactive with SARS-CoV polypeptides in a competitive inhibition assay. Briefly, a sample suspected of containing SARS-CoV antibodies is contacted with a SARS-CoV polypeptide of this disclosure which is bound to a substrate (for example, a microtiter plate). Excess sample is thoroughly washed away. A labeled (for example, enzyme-linked, fluorescent, radioactive, and the like) monoclonal antibody specific for the SARS-CoV polypeptide is then contacted with any previously formed polypeptide-antibody complexes and the amount of monoclonal antibody binding is measured. The amount of inhibition of monoclonal antibody binding is measured relative to a control (no monoclonal antibody), allowing for detection and measurement of antibody in the sample. The degree of monoclonal antibody inhibition can be a very specific assay for detecting SARS-CoV. Monoclonal antibodies can also be used for direct detection of SARS-CoV in cells or tissue samples by, for example, IFA analysis according to standard methods.

As a further example, a micro-agglutination test can be used to detect the presence of SARS-CoV antibodies in a sample. Briefly, latex beads, red blood cells or other agglutinable particles are coated with a SARS-CoV polypeptide of this disclosure and mixed with a sample, such that antibodies in the sample that are specifically reactive with the antigen crosslink with the antigen, causing agglutination. The agglutinated polypeptide-antibody complexes form a precipitate, visible with the naked eye or measurable by spectrophotometer. In a modification of the above test, SARS-CoV-specific antibodies of this disclosure can be bound to the agglutinable particles and SARS-CoV antigen in the sample thereby detected.

VII. Pharmaceutical and Immune Stimulatory Compositions and Uses Thereof

Pharmaceutical compositions including SARS-CoV nucleic acid sequences, SARS-CoV polypeptides, or antibodies that bind these polypeptides, are also encompassed by the present disclosure. These pharmaceutical compositions include a therapeutically effective amount of one or more SARS-CoV polypeptides, one or more nucleic acid molecules encoding a SARS-CoV polypeptide, or an antibody that binds a SARS-CoV polypeptide, in conjunction with a pharmaceutically acceptable carrier.

Disclosed herein are substances suitable for use as immune stimulatory compositions for the inhibition or treatment of SARS. Particular immune stimulatory compositions are directed against SARS-CoV, and include antigens obtained from SARS-CoV. In one embodiment, an immune stimulatory composition contains attenuated SARS-CoV. Methods of viral attenuation are well known in the art, and include, but are not limited to, high serial passage (for example, in susceptible host cells under specific environmental conditions to select for attenuated virions), exposure to a mutagenic agent (for example, a chemical mutagen or radiation), genetic engineering using recombinant DNA technology (for example, using gene replacement or gene knockout to disable one or more viral genes), or some combination thereof.

In another embodiment, the immune stimulatory composition contains inactivated SARS-CoV. Methods of viral inactivation are well known in the art, and include, but are not limited to, heat and chemicals (for example, formalin, β-propiolactone, and ethylenimines).

In yet another embodiment, the immune stimulatory composition contains a nucleic acid vector that includes SARS-CoV nucleic acid molecules described herein, or that includes a nucleic acid sequence encoding an immunogenic polypeptide or polypeptide fragment of SARS-CoV or derived from SARS-CoV, such as a polypeptide that encodes a surface protein of SARS-CoV.

In a further embodiment, the immune stimulatory composition contains a SARS-CoV subunit, such as glycoprotein, major capsid protein, or other gene products found to elicit humoral and/or cell mediated immune responses.

The provided immune stimulatory SARS-CoV polypeptides, constructs or vectors encoding such polypeptides, are combined with a pharmaceutically acceptable carrier or vehicle for administration as an immune stimulatory composition to human or animal subjects. In some embodiments, more than one immune stimulatory SARS-CoV polypeptide may be combined to form a single preparation.

The immunogenic formulations may be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The compositions provided herein, including those for use as immune stimulatory compositions, may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes.

The volume of administration will vary depending on the route of administration. By way of example, intramuscular injections may range from about 0.1 ml to about 1.0 ml. Those of ordinary skill in the art will know appropriate volumes for different routes of administration.

A relatively recent development in the field of immune stimulatory compounds (for example, vaccines) is the direct injection of nucleic acid molecules encoding peptide antigens (broadly described in Janeway & Travers, *Immunobiology: The Immune System In Health and Disease*, page 13.25, Garland Publishing, Inc., New York, 1997; and McDonnell & Askari, N. *Engl. J. Med.* 334:42-45, 1996). Vectors that include nucleic acid molecules described herein, or that include a nucleic acid sequence encoding an immunogenic SARS-CoV polypeptide may be utilized in such DNA vaccination methods.

Thus, the term "immune stimulatory composition" as used herein also includes nucleic acid vaccines in which a nucleic acid molecule encoding a SARS-CoV polypeptide is administered to a subject in a pharmaceutical composition. For genetic immunization, suitable delivery methods known to those skilled in the art include direct injection of plasmid DNA into muscles (Wolff et al., *Hum. Mol. Genet.* 1:363, 1992), delivery of DNA complexed with specific protein carriers (Wu et al., *J. Biol. Chem.* 264:16985, 1989), co-precipitation of DNA with calcium phosphate (Benvenisty and Reshef, *Proc. Natl. Acad. Sci.* 83:9551, 1986), encapsulation of DNA in liposomes (Kaneda et al., *Science* 243:375, 1989), particle bombardment (Tang et al., *Nature* 356:152, 1992; Eisenbraun et al., *DNA Cell Biol.* 12:791, 1993), and in vivo infection using cloned retroviral vectors (Seeger et al., *Proc. Natl. Acad. Sci.* 81:5849, 1984). Similarly, nucleic acid vaccine preparations can be administered via viral carrier.

The amount of immunostimulatory compound in each dose of an immune stimulatory composition is selected as an amount that induces an immunostimulatory or immunoprotective response without significant, adverse side effects. Such amount will vary depending upon which specific immunogen is employed and how it is presented. Initial injections may range from about 1 µg to about 1 mg, with some embodiments having a range of about 10 µg to about 800 µg, and still other embodiments a range of from about 25 µg to about 500 µg. Following an initial administration of the immune stimulatory composition, subjects may receive one or several booster administrations, adequately spaced. Booster administrations may range from about 1 µg to about 1 mg, with other embodiments having a range of about 10 µg to about 750 µg, and still others a range of about 50 µg to about 500 µg.

Periodic boosters at intervals of 1-5 years, for instance three years, may be desirable to maintain the desired levels of protective immunity.

It is also contemplated that the provided immunostimulatory molecules and compositions can be administered to a subject indirectly, by first stimulating a cell in vitro, which stimulated cell is thereafter administered to the subject to elicit an immune response. Additionally, the pharmaceutical or immune stimulatory compositions or methods of treatment may be administered in combination with other therapeutic treatments.

VIII. Kits

Also provided herein are kits useful in the detection and/or diagnosis of SARS-CoV. This includes kits for use with nucleic acid and protein detection methods, such as those disclosed herein.

The SARS-CoV-specific oligonucleotide primers and probes described herein can be supplied in the form of a kit for use in detection of SARS-CoV. In such a kit, an appropriate amount of one or more of the oligonucleotides is provided in one or more containers, or held on a substrate. An oligonucleotide primer or probe can be provided in an aqueous solution or as a freeze-dried or lyophilized powder, for instance. The container(s) in which the oligonucleotide(s) are supplied can be any conventional container that is capable of holding the supplied form, for instance, microfuge tubes, ampoules, or bottles. In some applications, pairs of primers are provided in pre-measured single use amounts in individual (typically disposable) tubes or equivalent containers. With such an arrangement, the sample to be tested for the presence of a SARS-CoV nucleic acid can be added to the individual tubes and amplification carried out directly.

The amount of each oligonucleotide supplied in the kit can be any appropriate amount, and can depend on the market to which the product is directed. For instance, if the kit is adapted for research or clinical use, the amount of each oligonucleotide primer provided would likely be an amount sufficient to prime several PCR amplification reactions. General guidelines for determining appropriate amounts can be found, for example, in Sambrook et al., *Molecular Cloning: A Laboratory Manual*, Cold Spring Harbor Laboratory Press, Cold Spring Harbor, N.Y., 2001; Ausubel et al. (eds.), *Short Protocols in Molecular Biology*, John Wiley and Sons, New York, N.Y., 1999; and Innis et al., *PCR Applications, Protocols for Functional Genomics*, Academic Press, Inc., San Diego, Calif., 1999. A kit can include more than two primers, in order to facilitate the amplification of a larger number of SARS-CoV nucleotide sequences.

In some embodiments, kits also include one or more reagents necessary to carry out in vitro amplification reactions, including DNA sample preparation reagents, appropriate buffers (for example, polymerase buffer), salts (for example, magnesium chloride), and deoxyribonucleotides (dNTP5).

Kits can include either labeled or unlabeled oligonucleotide primers and/or probes for use in detection of SARS-CoV nucleotide sequences. The appropriate sequences for such a probe will be any sequence that falls between the annealing sites of the two provided oligonucleotide primers, such that the sequence that the probe is complementary to is amplified during the amplification reaction.

One or more control sequences for use in the amplification reactions also can be supplied in the kit. In other particular embodiments, the kit includes equipment, reagents, and instructions for extracting and/or purifying nucleotides from a sample.

Kits for the detection of SARS-CoV antigen include for instance at least one SARS-CoV antigen-specific binding agent (for example, a polyclonal or monoclonal antibody or antibody fragment). The kits may also include means for detecting antigen:specific binding agent complexes, for instance the specific binding agent may be detectably labeled. If the specific binding agent is not labeled, it may be detected by second antibodies or protein A, for example, which may also be provided in some kits in one or more separate containers. Such techniques are well known.

Another example of an assay kit provided herein is a recombinant SARS-CoV-specific polypeptide (or fragment thereof) as an antigen and an enzyme-conjugated anti-human antibody as a second antibody. Examples of such kits also can include one or more enzymatic substrates. Such kits can be used to test if a sample from a subject contains antibodies against a SARS-CoV-specific protein.

The subject matter of the present disclosure is further illustrated by the following non-limiting Examples.

EXAMPLES

Example 1

Isolation and Characterization of SARS-CoV

Virus Isolation and Ultrastructural Characterization

This example describes the original isolation and characterization of a new human coronavirus from patients with SARS.

A variety of clinical specimens (blood, serum, material from oropharyngeal swabs or washings, material from nasopharyngeal swabs, and tissues of major organs collected at autopsy) from patients meeting the case definition of SARS were sent to the Centers for Disease Control and Prevention (CDC) as part of the etiologic investigation of SARS. These samples were inoculated onto a number of continuous cell lines, including Vero E6, NCI-H292, MDCK, LLC-MK2, and B95-8 cells, and into suckling ICR mice by the intracranial and intraperitoneal routes. All cultures were observed daily for CPE. Maintenance medium was replenished at day seven, and cultures were terminated fourteen days after inoculation. Any cultures exhibiting identifiable CPE were subjected to several procedures to identify the cause of the effect. Suckling mice were observed daily for fourteen days, and any sick or dead mice were further tested by preparing a brain suspension that was filtered and subcultured. Mice that remained well after fourteen days were killed, and their test results were recorded as negative.

Two cell lines, Vero E6 cells and NCI-H292 cells, inoculated with oropharyngeal specimens from Patient 16 (a 46 year old male physician with an epidemiologic link to a hospital with multiple SARS patients) initially showed CPE (Table 1)

TABLE 1

Specimens from patients with SARS that were positive for SARS-CoV by one or more methods*.

| Patient No | Exposure and Setting | Age/Sex | Findings on Chest Radiograph | Hospital-ization | Serologic Results | Specimen | Isolation | RT-PCR |
|---|---|---|---|---|---|---|---|---|
| 1 | Singapore, hospital | 53 yr/F | Pneumonia | Yes | + | Nasal, oropharyngeal swabs | − | Not done |
| 2† | Hong Kong, hotel | 36 yr/F | Pneumonia | Yes | + | Nasal, swab | − | Not done |
| 3 | Hong Kong, hotel | 22 yr/M | Pneumonia | Yes | + | Swab | − | − |
| 4† | Hong Kong, hotel | 39 yr/M | Pneumonia | Yes | + | Nasal, pharyngeal swab | − | − |
| 5 | Hong Kong, hotel | 49 Yr/M | Pneumonia | Yes | Not done | Sputum | + | + |
| 6‡ | Hong Kong, hotel | 46 yr/M | Pneumonia | Yes | + | Kidney, lung, broncho-alveolar lavage | +§ | + |
| 7 | Vietnam, hospital | Adult/unknown | Pneumonia | Yes | − | Oropharyngeal wash | + | + |
| 8 | Vietnam, hospital | Adult/unknown | Pneumonia | Yes | − | Oropharyngeal wash | − | + |
| 9 | Vietnam, hospital | Adult/unknown | Pneumonia | Yes | − | Oropharyngeal wash | − | + |
| 10 | Vietnam, hospital | Adult/unknown | Pneumonia | Yes | − | Oropharyngeal wash | − | + |
| 11 | Vietnam, hospital | Adult/unknown | Pneumonia | Yes | − | Oropharyngeal wash | − | + |
| 12 | Vietnam, hospital | Adult/unknown | Pneumonia | Yes | − | Oropharyngeal wash | − | + |
| 13 | Vietnam, hospital | Adult/unknown | Pneumonia | Yes | − | Oropharyngeal wash | + | + |
| 14 | Vietnam, hospital | Adult/unknown | Pneumonia | Yes | − | Oropharyngeal wash | − | + |
| 15 | Vietnam, hospital | Adult/unknown | Pneumonia | Yes | − | Oropharyngeal wash | − | + |
| 16 | Vietnam, hospital | 46 yr/M | Pneumonia | Yes | + | Nasal, oropharyngeal swabs | +¶ | + |
| 17 | Canada, family | 43 yr/M | Pneumonia | Yes | Not done | Lung, bone marrow | − | |
| 18 | Taiwan, family | 51 yr/F | Pneumonia | Yes | − | Sputum | − | + |
| 19 | Hong Kong, hotel | Adult/F | Pneumonia | Yes | + | Oropharyngeal wash | − | + |

*Plus signs denote positive results, and minus signs negative results. The serologic and RT-PCR assays were not necessarily performed on samples obtained at the same time.
†This was a late specimen, antibody positive at first sample.
‡Travel included China, Hong Kong (hotel), and Hanoi (the patient was the index patient in the French Hospital).
§Isolation was from the kidney only.
¶Isolation was from the oropharyngeal only.

The CPE in the Vero E6 cells was first noted on the fifth day post-inoculation; it was focal, with cell rounding and a refractive appearance in the affected cells that was soon followed by cell detachment (FIG. 1A). The CPE spread quickly to involve the entire cell monolayer within 24 to 48 hours. Subculture of material after preparation of a master seed stock (used for subsequent antigen production) resulted in the rapid appearance of CPE, as noted above, and in complete destruction of the monolayer in the inoculated flasks within 48 hours. Similar CPE was also noted in four additional cultures: three cultures of respiratory specimens (two oropharyngeal washes and one sputum specimen) and one culture of a suspension of kidney tissue obtained at autopsy. In these specimens, the initial CPE was observed between day two and day four and, as noted above, the CPE rapidly progressed to involve the entire cell monolayer.

Tissue culture samples showing CPE were prepared for electron-microscopical examination. Negative-stain electron-microscopical specimens were prepared by drying culture supernatant, mixed 1:1 with 2.5% paraformaldehyde, onto Formvarcarbon-coated grids and staining with 2% methylamine tungstate. Thin-section electron-microscopical specimens were prepared by fixing a washed cell pellet with 2.5% glutaraldehyde and embedding the cell pellet in epoxy resin. In addition, a master seed stock was prepared from the remaining culture supernatant and cells by freeze-thawing the culture flask, clarifying the thawed contents by centrifugation at 1000×g, and dispensing the supernatant into aliquots stored in gas phase over liquid nitrogen. The master seed stock was subcultured into 850-cm$^2$ roller bottles of Vero E6 cells for the preparation of formalin-fixed positive control cells for immunohistochemical analysis, mixed with normal Vero E6 cells, and gamma-irradiated for preparation of spot slides for IFA tests or extracted with detergent and gamma-irradiated for use as an ELISA antigen for antibody tests.

Figure 2A:
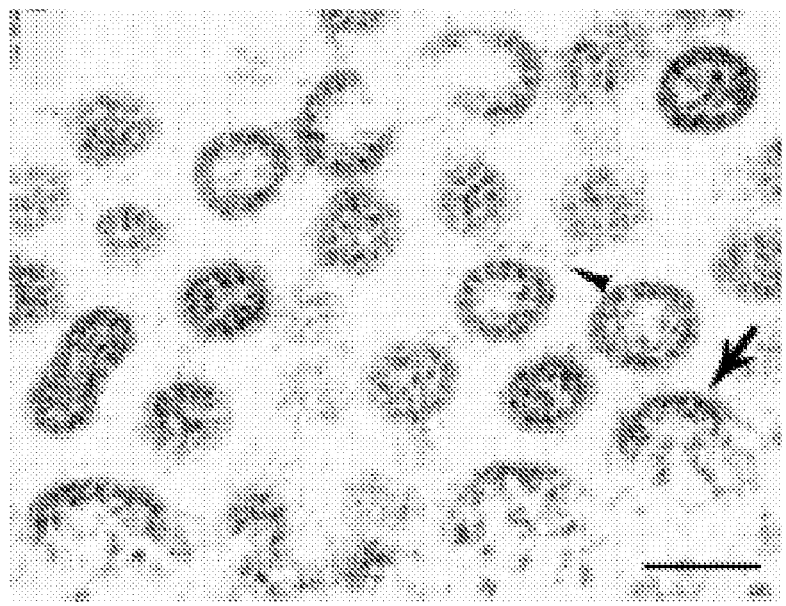
Figure 2B:
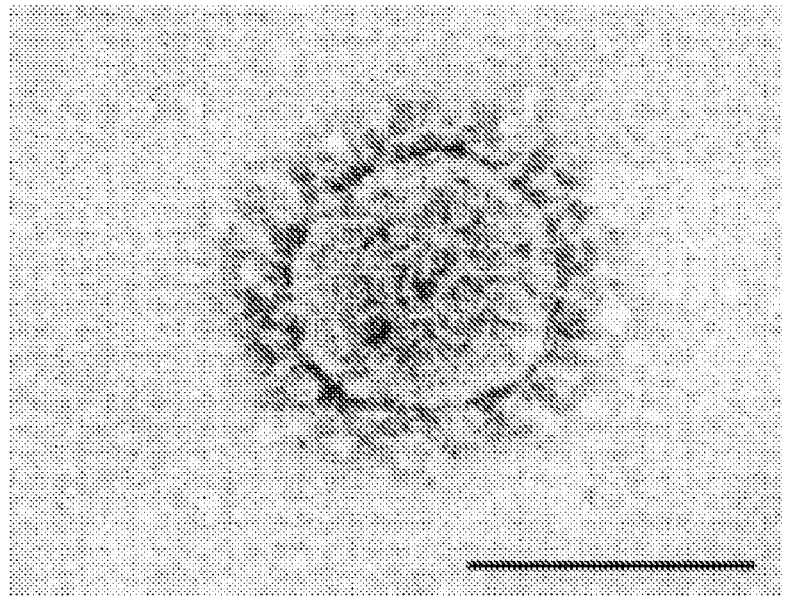

Examination of CPE-positive Vero E6 cells by thin-section electron microscopy revealed characteristic coronavirus particles within the cisternae of the rough endoplasmic reticulum and in vesicles (FIG. 2A) (Becker et al., *J. Virol.* 1:1019-27, 1967; Oshiro et al. *J. Gen. Virol.* 12:161-8, 1971). Extracellular particles were found in large clusters and adhering to the surface of the plasma membrane. Negative-stain electron microscopy identified coronavirus particles, 80 to 140 nm in diameter, with 20- to 40-nm complex surface projections surrounding the periphery (FIG. 2B). Hemagglutinin esterase-type glycoprotein projections were not seen.

The isolation and growth of a human-derived coronavirus in Vero E6 cells were unexpected. The previously known human coronaviruses are notably fastidious, preferring select cell lines, organ culture, or suckling mice for propagation. The only human or animal coronavirus which has been shown to grow in Vero E6 cells is PEDV, and it requires the addition of trypsin to culture medium for growth in the cells. Moreover, PEDV adapted to growth in Vero E6 cells results in a strikingly different CPE, with cytoplasmic vacuoles and the formation of large syncytia. Syncytial cells were only observed occasionally in monolayers of Vero E6 cells infected with the SARS-CoV; they clearly do not represent the dominant CPE.

Reverse Transcription-Polymerase Chain Reaction and Sequencing

For RT-PCR assays, cell-culture supernatants were placed in lysis buffer. RNA extracts were prepared from 100 µl of each specimen (or culture supernatant) with the automated NucliSens extraction system (bioMérieux, Durham, N.C.). Initially, degenerate, inosine-containing primers IN-2 (+) 5'GGGTTGGGACTA TCCTAAGTGTGA3' (SEQ ID NO: 34) and IN-4(−) 5'TAACACACAACICCATCA TCA3' (SEQ ID NO: 35) were designed to anneal to sites encoding conserved amino acid motifs that were identified on the basis of alignments of available coronavirus ORF1a, ORF1b, S, HE, M, and N gene sequences. Additional, SARS-specific, primers Cor-p-F2 (+) 5'CTAACATGCTTAGGATAATGG3' (SEQ ID NO: 13), Cor-p-F3 (+) 5'GCCTCTCTTGTTCT-TGCTCGC3' (SEQ ID NO: 14), and Cor-p-R1 (−) 5' CAG-GTAAGCGTAAAACTCATC3' (SEQ ID NO: 15) were designed as sequences were generated from RT-PCR products amplified with the degenerate primers. These SARS-specific primers were used to test patient specimens for SARS (see below). Primers used for specific amplification of human metapneumovirus have been described by Falsey et al. (*J. Infect. Dis.* 87:785-90, 2003).

For RT-PCR products of less than 3 kb, cDNA was synthesized in a 20 µl reaction mixture containing 500 ng of RNA, 200 U of Superscript™ II reverse transcriptase (Invitrogen Life Technologies, Carlsbad, Calif.), 40 U of RNasin (Promega Corp., Madison, Wis.), 100 mM each dNTP (Roche Molecular Biochemicals, Indianapolis, Ind.), 4 µl of 5× reaction buffer (Invitrogen Life Technologies, Carlsbad, Calif.), and 200 pmol of the reverse primer. The reaction mixture, except for the reverse transcriptase, was heated to 70° C. for 2 minutes, cooled to 4° C. for 5 minutes and then heated to 42° C. in a thermocycler. The mixture was held at 42° C. for 4 minutes, and then the reverse transcriptase was added, and the reactions were incubated at 42° C. for 45 minutes. Two microliters of the cDNA reaction was used in a 50 µl PCR reaction containing 67 mM Tris-HCl (pH 8.8), 1 mM each primer, 17 mM ammonium sulfate, 6 mM EDTA, 2 mM MgCl$_2$, 200 mM each dNTP, and 2.5 U of Taq DNA polymerase (Roche Molecular Biochemicals, Indianapolis, Ind.). The thermocycler program for the PCR consisted of 40 cycles of denaturation at 95° C. for 30 seconds, annealing at 42° C. for 30 seconds, and extension at 65° C. for 30 seconds. For SARS-CoV-specific primers, the annealing temperature was increased to 55° C.

For amplification of fragments longer than 3 kb, regions of the genome between sections of known sequence were amplified by means of a long RT-PCR protocol and SARS-CoV-specific primers. First-strand cDNA synthesis was performed at 42° C. or 50° C. using Superscript™ II RNase H reverse transcriptase (Invitrogen Life Technologies, Carlsbad, Calif.) according to the manufacturer's instructions with minor modifications. Coronavirus-specific primers (500 ng) and SARS-CoV RNA (350 ng) were combined with the PCR Nucleotide Mix (Roche Molecular Biochemicals, Indianapolis, Ind.), heated for 1 minute at 94° C., and cooled to 4° C. in a thermocycler. The 5× first-strand buffer, dithiothreitol (Invitrogen Life Technologies, Carlsbad, Calif.), and Protector RNase Inhibitor (Roche Molecular Biochemicals, Indianapolis, Ind.) were added, and the samples were incubated at 42° C. or 50° C. for 2 minutes. After reverse transcriptase (200 U) was added, the samples were incubated at 42° C. or 50° C. for 1.5 to 2 hours. Samples were inactivated at 70° C. for 15 minutes and subsequently treated with 2 U of RNase H (Roche Molecular Biochemicals, Indianapolis, Ind.) at 37° C. for 30 minutes. Long RT-PCR amplification of 5- to 8-kb fragments was performed using Taq Plus Precision (Stratagene, La Jolla, Calif.) and AmpliWax PCR Gem 100 beads (Applied Biosystems; Foster City, Calif.) for "hot start" PCR with the following thermocycling parameters: denaturation at 94° C. for 1 minute followed by 35 cycles of 94° C. for 30 seconds, 55° C. for 30 seconds, an increase of 0.4 degrees per second up to 72° C., and 72° C. for 7 to 10 minutes, with a final extension at 72° C. for 10 minutes. RT-PCR products were separated by electrophoresis on 0.9% agarose TAE gels and purified by use of a QIAquick Gel Extraction Kit (Qiagen, Inc., Santa Clarita, Calif.).

In all cases, the RT-PCR products were gel-isolated and purified for sequencing by means of a QIAquick Gel Extraction kit (Qiagen, Inc., Santa Clarita, Calif.). Both strands were sequenced by automated methods, using fluorescent dideoxy-chain terminators (Applied Biosystems; Foster City, Calif.).

The sequence of the leader was obtained from the subgenomic mRNA coding for the N gene and from the 5' terminus of genomic RNA. The 5' rapid amplification of cDNA ends (RACE) technique (Harcourt et al., *Virology* 271:334-49, 2000) was used with reverse primers specific for the N gene or for the 5' untranslated region. RACE products were either sequenced directly or were cloned into a plasmid vector before sequencing. A primer that was specific for the leader of SARS-CoV was used to amplify the region between the 5'-terminus of the genome and known sequences in the rep gene. The 3'-terminus of the genome was amplified for sequencing by use of an oligo-(dT) primer and primers specific for the N gene.

Once the complete SARS-CoV genomic sequence had been determined, it was confirmed by sequencing a series of independently amplified RT-PCR products spanning the entire genome. Positive- and negative-sense sequencing primers, at intervals of approximately 300 nt, were used to generate a confirmatory sequence with an average redundancy of 9.1. The confirmatory sequence was identical to the original sequence. The genomic sequence (SEQ ID NO: 1) was published in the GenBank sequence database (Accession No. AY278741) on Apr. 21, 2003.

Sequence Analysis

Predicted amino acid sequences were compared with those from reference viruses representing each species for which complete genomic sequence information was available: group 1 representatives included human coronavirus 229E (GenBank Accession No. AF304460), porcine epidemic diarrhea virus (GenBank Accession No. AF353511), and transmissible gastroenteritis virus (GenBank Accession No. AF271965); group 2 representatives included bovine coronavirus (GenBank Accession No. AF220295) and mouse hepatitis virus (GenBank Accession No. AF201929); group 3 was represented by infectious bronchitis virus (GenBank Accession No. M95169). Sequences for representative strains of other coronavirus species for which partial sequence information was available were included for some of the structural protein comparisons: group 1 representative strains included canine coronavirus (GenBank Accession No. D13096), feline coronavirus (GenBank Accession No. AY204704), and porcine respiratory coronavirus (GenBank Accession No. Z24675); and group 2 representatives included three strains of human coronavirus OC43 (GenBank Accession Nos. M76373, L14643 and M93390), porcine hemagglutinating encephalomyelitis virus (GenBank Accession No. AY078417), and rat coronavirus (GenBank Accession No. AF207551).

Figure 3:
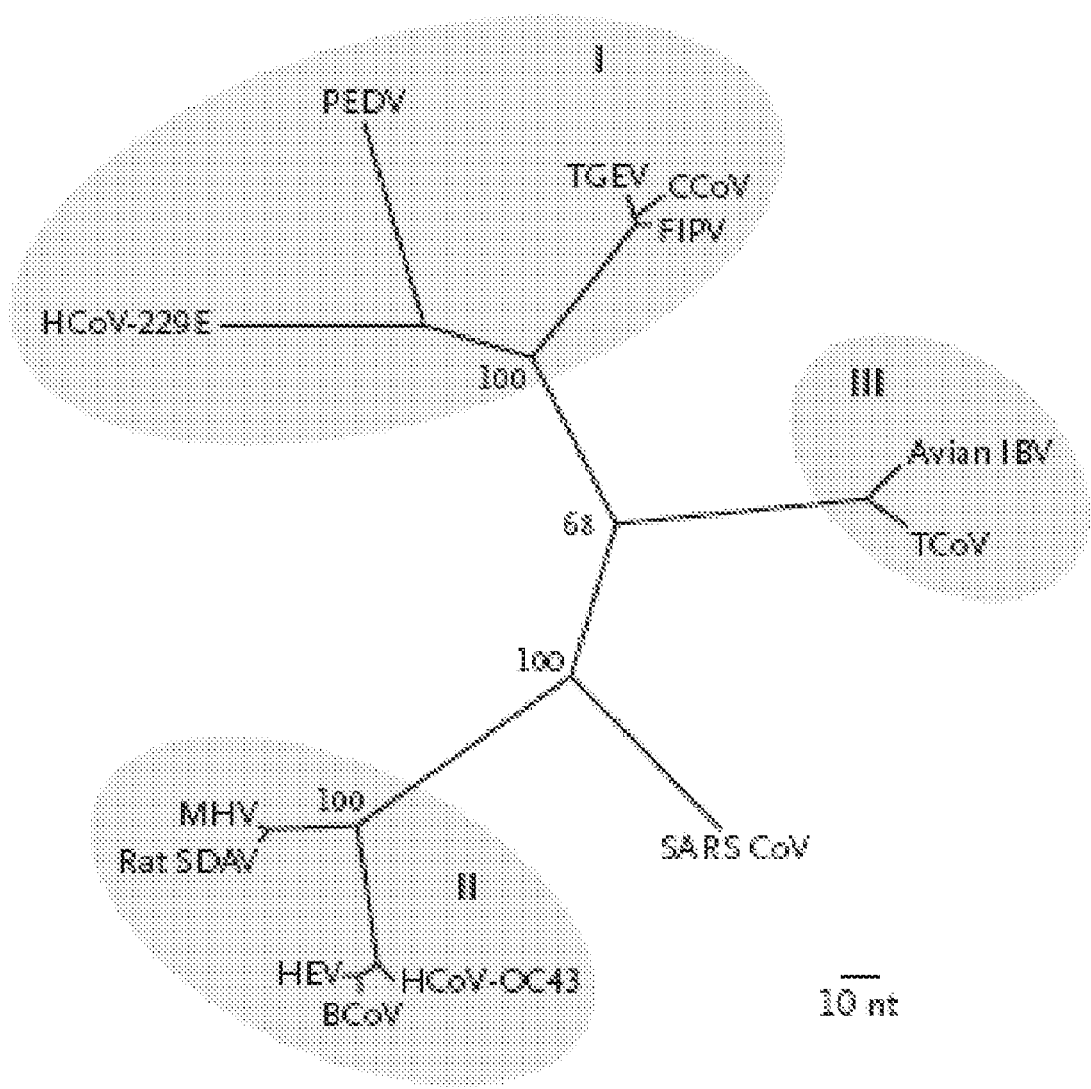

Partial nucleotide sequences of the polymerase gene were aligned with published coronavirus sequences, using CLUSTAL W for Unix (version 1.7; Thompson et al., *Nucleic Acids Res.* 22:4673-80, 1994). Phylogenetic trees were computed by maximum parsimony, distance, and maximum likelihood-based criteria analysis with PAUP (version 4.0.d10; Swofford ed., *Phylogenetic Analysis using Parsimony and other Methods*, Sinauer Associates, Sunderland, Mass.). When compared with other human and animal coronaviruses, the nucleotide and deduced amino acid sequence from this region had similarity scores ranging from 0.56 to 0.63 and from 0.57 to 0.74, respectively. The highest sequence similarity was obtained with group II coronaviruses. The maximum-parsimony tree obtained from the nucleotide-sequence alignment is shown in FIG. 3. Bootstrap analyses of the internal nodes at the internal branches of the tree provided strong evidence that the SARS-CoV is genetically distinct from other known coronaviruses.

Microarray analyses (using a long oligonucleotide DNA microarray with array elements derived from highly conserved regions within viral families) of samples from infected and uninfected cell cultures gave a positive signal for a group of eight oligonucleotides derived from two virus families: Coronaviridae and Astroviridae (Wang et al., PNAS 99:15687-92, 2002). All of the astroviruses and two of the coronavirus oligonucleotides share a consensus sequence motif that maps to the extreme 3'-end of astroviruses and two members of the coronavirus family: avian infectious bronchitis and turkey coronavirus (Jonassen et al., *J. Gen. Virol.* 79:715-8, 1998). Results were consistent with the identity of the isolate as a coronavirus.

Figure 4:
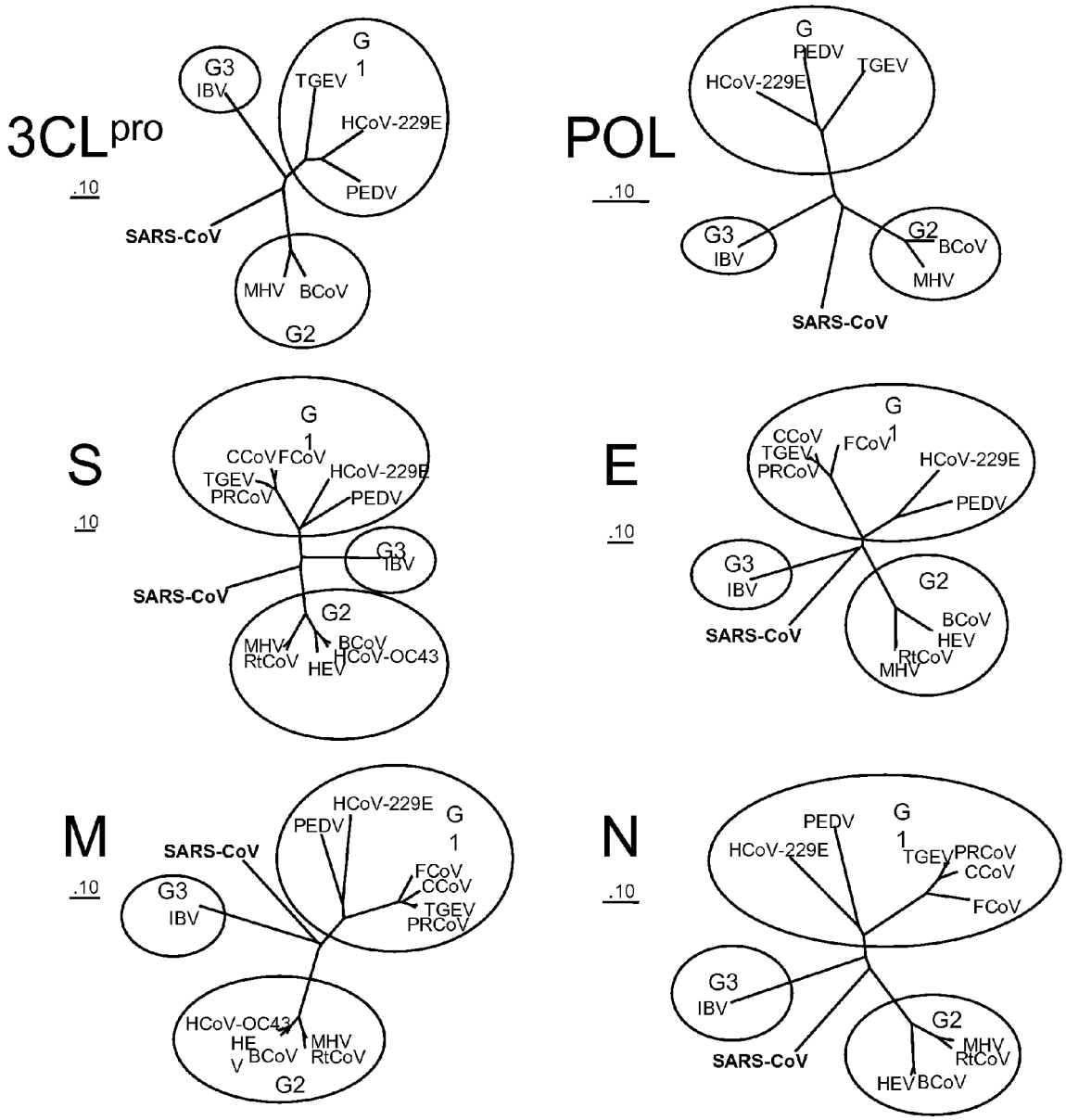
Figure 6A:
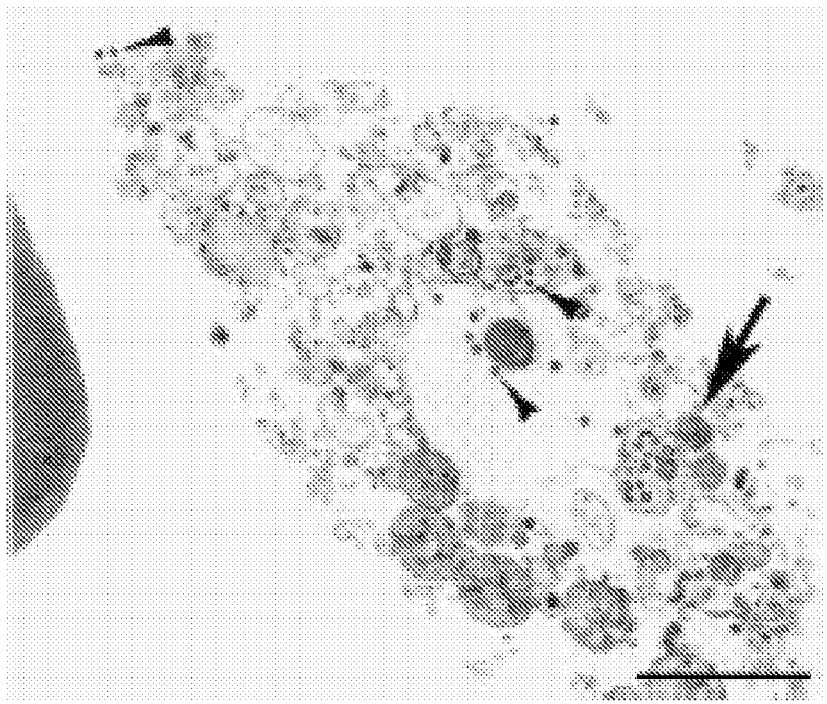
Figure 6B:
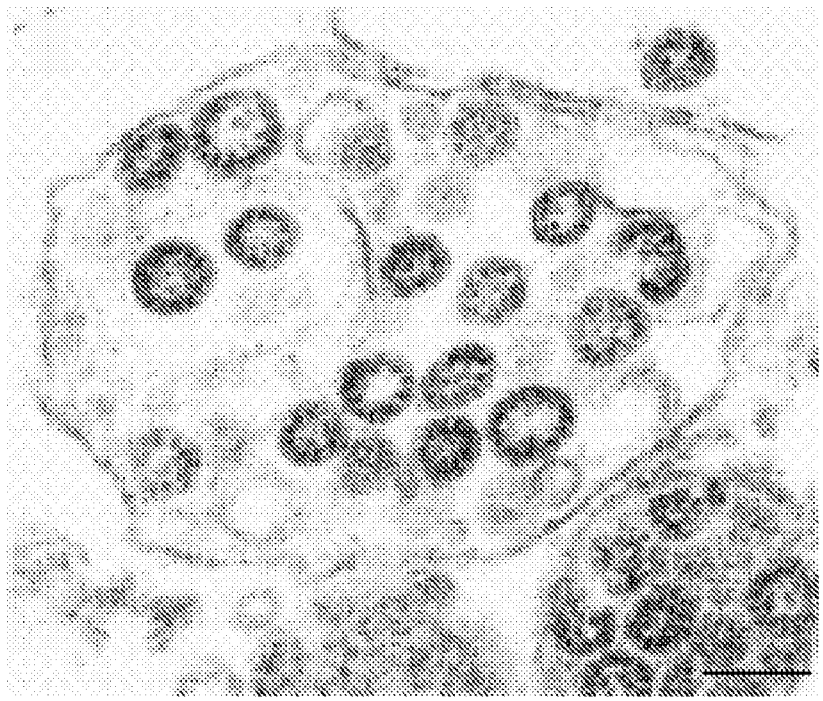

Additional sequence alignments and neighbor-joining trees were generated by using ClustalX (Thompson et al., *Nucleic Acids Res.* 25:4876-82, 1997), version 1.83, with the Gonnet protein comparison matrix. The resulting trees were adjusted for final output by using treetool version 2.0.1. Uncorrected pairwise distances were calculated from the aligned sequences by using the Distances program from the Wisconsin Sequence Analysis Package, version 10.2 (Accelrys, Burlington, Mass.). Distances were converted to percent identity by subtracting from 100. The amino acid sequences for three well-defined enzymatic proteins encoded by the rep gene and the four major structural proteins of SARS-CoV were compared with those from representative viruses for each of the species of coronavirus for which complete genomic sequence information was available (FIG. 4, Table 2). The topologies of the resulting phylograms are remarkably similar (FIG. 4). For each protein analyzed, the species formed monophyletic clusters consistent with the established taxonomic groups. In all cases, SARS-CoV sequences segregated into a fourth, well-resolved branch. These clusters were supported by bootstrap values above 90% (1000 replicates). Consistent with pairwise comparisons between the previously characterized coronavirus species (Table 2), there was greater sequence conservation in the enzymatic proteins (3CL$^{pro}$, polymerase (POL), and helicase (HEL)) than among the structural proteins (S, E, M, and N). These results indicate that SARS-CoV is not closely related to any of the previously characterized coronaviruses and forms a distinct group within the genus *Coronavirus*.

TABLE 2

Pairwise amino acid identities of coronavirus proteins.

| Group | Virus | 3CLPRO | POL | HEL | S | E | M | N |
|---|---|---|---|---|---|---|---|---|
| | | Pairwise Amino Acid Identity (Percent) | | | | | | |
| G1 | HCoV-229E | 40.1 | 58.8 | 59.7 | 23.9 | 22.7 | 28.8 | 23.0 |
| | PEDV | 44.4 | 59.5 | 61.7 | 21.7 | 17.6 | 31.8 | 22.6 |
| | TGEV | 44.0 | 59.4 | 61.2 | 20.6 | 22.4 | 30.0 | 25.6 |
| G2 | BCoV | 48.8 | 66.3 | 68.3 | 27.1 | 20.0 | 39.7 | 31.9 |
| | MHV | 49.2 | 66.5 | 67.3 | 26.5 | 21.1 | 39.0 | 33.0 |
| G3 | IBV | 41.3 | 62.5 | 58.6 | 21.8 | 18.4 | 27.2 | 24.0 |
| | | Predicted Protein Length (aa) | | | | | | |
| | SARS-CoV | 306 | 932 | 601 | 1255 | 76 | 221 | 422 |
| | CoV Range | 302-307 | 923-940 | 506-600 | 1173-1452 | 76-108 | 225-262 | 377-454 |

Example 2

Detection of SARS-CoV in a Subject

This example demonstrates the detection of SARS-CoV in patient specimens using SARS-CoV-specific primers.

The SARS-specific primers Cor-p-F2 (SEQ ID NO: 13), Cor-p-F3 (SEQ ID NO: 14) and Cor-p-R1 (SEQ ID NO: 15) were used to test patient specimens for SARS. One primer for each set was 5'-end-labeled with 6-FAM to facilitate GeneScan analysis. One-step amplification reactions were performed with the Access RT-PCR System (Promega, Madison, Wis.) as described by Falsey et al., *J. Infect. Dis.* 87:785-90, 2003. Positive and negative RT-PCR controls, containing standardized viral RNA extracts, and nuclease-free water were included in each run. Amplified 6-FAM-labeled products were analyzed by capillary electrophoresis on an ABI 3100 Prism Genetic Analyzer with GeneScan software (version 3.1.2; Applied Biosystems; Foster City, Calif.). Specimens were considered positive for SARS-CoV if the amplification products were within one nucleotide of the expected product size (368 nucleotides for Cor-p-F2 or Cor-p-R1 and 348 nucleotides for Cor-p-F3 or Cor-p-R1) for both specific primer sets, as confirmed by a second PCR reaction from another aliquot of RNA extract in a separate laboratory. Where DNA yield was sufficient, the amplified products were also sequenced. Additionally, as described above, microarray-based detection of SARS-CoV in patient specimens was carried out (Wang et al., *PNAS* 99:15687-92, 2002 and Bohlander et al., *Genomics* 13:1322-24, 1992).

Example 3

Immunohistochemical and Histopathological Analysis, and Electron-Microscopical Analysis of Bronchoalveolar Lavage Fluid This example illustrates immunohistochemical, histopathological and electron-microscopical analysis of Vero E6 cells infected with the SARS-CoV and tissue samples from SARS patients.

Formalin-fixed, paraffin-embedded Vero E6 cells infected with the SARS-CoV and tissues obtained from patients with SARS were stained with hematoxylin and eosin and various immunohistochemical stains. Immunohistochemical assays were based on a method described previously for hantavirus (Zaki et al., *Amer. J. Pathol.* 146:552-79, 1995). Briefly, 4-μm sections were deparaffinized, rehydrated, and digested in Proteinase K for 15 minutes. Slides were then incubated for 60 minutes at room temperature with monoclonal antibodies, polyclonal antiserum or ascitic fluids derived from animal species with reactivities to various known coronaviruses, and with a convalescent-phase serum specimen from a patient with SARS.

Optimal dilutions of the primary antibodies were determined by titration experiments with coronavirus-infected cells from patients with SARS and with noninfected cells or, when available, with concentrations recommended by the manufacturers. After sequential application of the appropriate biotinylated link antibody, avidin-alkaline phosphatase complex, and naphthol-fast red substrate, sections were counterstained in Mayer's hematoxylin and mounted with aqueous mounting medium. The following antibody and tissue controls were used: serum specimens from noninfected animals, various coronavirus-infected cell cultures and animal tissues, noninfected cell cultures, and normal human and animal tissues. Tissues from patients were also tested by immunohistochemical assays for various other viral and bacterial pulmonary pathogens. In addition, a BAL specimen was available from one patient for thin-section electron-microscopical evaluation.

Lung tissues were obtained from the autopsy of three patients and by open lung biopsy of one patient, 14-19 days following onset of SARS symptoms. Confirmatory laboratory evidence of infection with coronavirus was available for two patients (patients 6 and 17) and included PCR amplification of coronavirus nucleic acids from tissues, viral isolation from BAL fluid or detection of serum antibodies reactive with coronavirus (Table 1). For two patients, no samples were available for molecular, cell culture, or serological analysis; however, both patients met the CDC definition for probable SARS cases and had strong epidemiologic links with laboratory-confirmed SARS cases. Histopathologic evaluation of lung tissues of the four patients showed diffuse alveolar damage at various levels of progression and severity. Changes included hyaline membrane formation, interstitial mononuclear inflammatory infiltrates, and desquamation of pneumocytes in alveolar spaces (FIG. 5A). Other findings identified in some patients included focal intraalveolar hemorrhage, necrotic inflammatory debris in small airways, and organizing pneumonia. Multinucleated syncytial cells were identified in the intraalveolar spaces of two patients who died 14 and 17 days, respectively, after onset of illness. These cells contained abundant vacuolated cytoplasm with cleaved and convoluted nuclei. No obvious intranuclear or intracytoplasmic viral inclusions were identified (FIG. 5B), and electron-microscopical examination of a limited number of these syncytial cells revealed no coronavirus particles. No definitive immunostaining was identified in tissues from SARS patients with the use of a battery of immunohistochemical stains reactive with coronaviruses from antigenic groups I, II, and III. In addition, no staining of patient tissues was identified with the use of immunohistochemical stains for influenzaviruses A and B, adenoviruses, Hendra and Nipah viruses, human metapneumovirus, respiratory syncytial virus, measles virus, *Mycoplasma pneumoniae*, and *Chlamydia pneumoniae*.

Evaluation of Vero E6 cells infected with coronavirus isolated from a patient with SARS revealed viral CPE that included occasional multinucleated syncytial cells but no obvious viral inclusions (FIG. 5C). Immunohistochemical assays with various antibodies reactive with coronaviruses from antigenic group I, including HCoV-229E, FIPV and TGEV, and with an immune serum specimen from a patient with SARS, demonstrated strong cytoplasmic and membranous staining of infected cells (FIG. 5C and Table 3); however, cross-reactivity with the same immune human serum sample and FIPV antigen was not observed. No staining was identified with any of several monoclonal or polyclonal antibodies reactive with coronaviruses in antigenic group II (HCoV-OC43, BCoV and MHV) or group III (TCoV and IBV-Avian). Electron microscopical examination of a BAL fluid from one patient revealed many coronavirus-infected cells (FIGS. 6A-B).

TABLE 3

Immunohistochemical reactivities of various polyclonal group I anti-coronavirus reference antiserum samples with a coronavirus isolated from a patient with SARS and with selected antigenic group I coronaviruses.

| | Immunohistochemical reactivity of antiserum with coronavirus-infected culture cells | | |
|---|---|---|---|
| Antiserum | SARS-CoV (Vero E6) | HCoV-229E (mouse 3T3-hAPN) | FIPV-1 (BHK-fAPN) |
| Convalescent-phase SARS (patient 3) | + | + | − |
| Guinea pig anti-HCoV-229E | + | + | − |
| Rabbit anti HCoV-229E | + | + | + |
| Feline anti-FIPV-1 | + | + | + |
| Porcine anti-TGEV | + | − | + |

Example 4

SARS-CoV Serologic Analysis

This example illustrates representative methods of performing serological analysis of SARS-CoV.

Spot slides were prepared by applying 15 μl of the suspension of gamma-irradiated mixed infected and noninfected cells onto 12-well Teflon-coated slides. Slides were allowed to air dry before being fixed in acetone. Slides were then stored at −70° C. until used for IFA tests (Wulff and Lange, *Bull. WHO* 52:429-36, 1975). An ELISA antigen was prepared by detergent extraction and subsequent gamma irradiation of infected Vero E6 cells (Ksiazek et al., *J. Infect. Dis.* 179 (suppl. 1):S191-8, 1999). The optimal dilution (1:1000) for the use of this antigen was determined by checkerboard titration against SARS patient serum from the convalescent phase; a control antigen, similarly prepared from uninfected Vero E6 cells, was used to control for specific reactivity of tested sera. The conjugates used were goat antihuman IgG, IgA, and IgM conjugated to fluorescein isothiocyanate and horseradish peroxidase (Kirkegaard and Perry, Gaithersburg, Md.), for the IFA test and ELISA, respectively. Specificity and cross-reactivity of a variety of serum samples to the newly identified virus were evaluated by using the tests described herein. For this evaluation, serum from SARS patients in Singapore, Bangkok and Hong Kong was used, along with serum from healthy blood donors from the CDC serum bank and from persons infected with known human coronavirus (human coronaviruses OC43 and 229E) (samples provided by E. Walsh and A. Falsey, University of Rochester School of Medicine and Dentistry, Rochester, N.Y.).

Figure 1B:
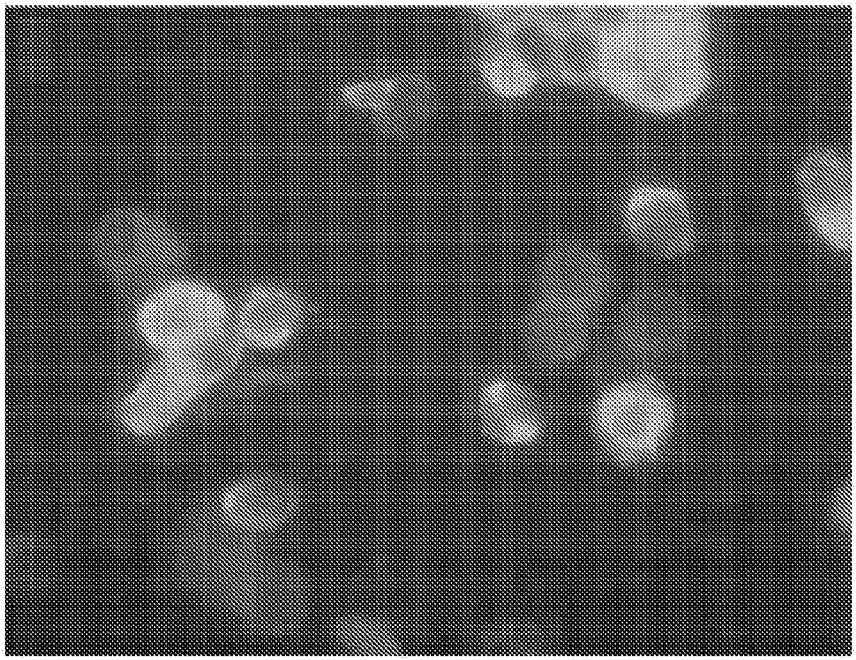

Spot slides with infected cells reacted with serum from patients with probable SARS in the convalescent phase (FIG. 1B). Screening of a panel of serum from patients with suspected SARS from Hong Kong, Bangkok, Singapore as well as the United States showed a high level of specific reaction with infected cells, and conversion from negative to positive reactivity or diagnostic rises in the IFA test by a factor of four. Similarly, tests of these same serum samples with the ELISA antigen showed high specific signal in the convalescent-phase samples and conversion from negative to positive antibody reactivity or diagnostic increases in titer (Table 4).

TABLE 4

Results of serological testing with both IFA assay and ELISA in SARS patients tested against the newly isolated human coronavirus.

| Source | Serum No. | Days After Onset | ELISA Titer* | IFA Titer* |
|---|---|---|---|---|
| Hong Kong | 1.1 | 4 | <100 | <25 |
| Hong Kong | 1.2 | 13 | ≧6400 | 1600 |
| Hong Kong | 2.1 | 11 | 400 | 100 |
| Hong Kong | 2.2 | 16 | 1600 | 200 |
| Hong Kong | 3.1 | 7 | <100 | <25 |
| Hong Kong | 3.2 | 17 | ≧6400 | 800 |
| Hong Kong | 4.1 | 8 | <100 | <25 |
| Hong Kong | 4.2 | 13 | 1600 | 50 |
| Hong Kong | 5.1 | 10 | 100 | <25 |
| Hong Kong | 5.2 | 17 | ≧6400 | 1600 |
| Hong Kong | 6.1 | 12 | 1600 | 200 |
| Hong Kong | 6.2 | 20 | ≧6400 | 6400 |
| Hong Kong | 7.1 | 17 | 400 | 50 |
| Hong Kong | 7.2 | 24 | ≧6400 | 3200 |
| Hong Kong | 8.1 | 3 | <100 | <25 |
| Hong Kong | 8.2 | 15 | ≧6400 | 200 |
| Hong Kong (Hanoi) | 9.1 | 5 | <100 | <25 |
| Hong Kong | 9.2 | 11 | ≧6400 | 1600 |
| Bangkok | 1.1 | 2 | <100 | <25 |
| Bangkok | 1.2 | 4 | <100 | <25 |
| Bangkok | 1.3 | 7 | <100 | <25 |
| Bangkok | 1.4 | 15 | 1600 | 200 |
| United States | 1.1 | 2 | <100 | <25 |
| United States | 1.2 | 6 | 400 | 50 |
| United States | 1.3 | 13 | ≧6400 | 800 |
| Singapore | 1.1 | 2 | 100 | <25 |
| Singapore | 1.2 | 11 | ≧6400 | 800 |
| Singapore | 2.1 | 6 | 100 | <25 |
| Singapore | 2.2 | 25 | ≧6400 | 400 |
| Singapore | 3.1 | 6 | 100 | <25 |
| Singapore | 3.2 | 14 | ≧6400 | 400 |
| Singapore | 4.1 | 5 | 100 | <25 |
| Singapore | 4.2 | 16 | 1600 | 400 |

*Reciprocal of dilution

Information from the limited numbers of samples tested suggests that antibody is first detectable by IFA assay and ELISA between one and two weeks after the onset of symptoms in the patient. IFA testing and ELISA of a panel of 384 randomly selected serum samples (from U.S. blood donors) were negative for antibodies to the new coronavirus, with the exception of one specimen that had minimal reactivity on ELISA. A panel of paired human serum samples with diagnostic increases (by a factor of four or more) in antibody (with very high titers to the homologous viral antigen in the convalescent-phase serum) to the two known human coronaviruses, OC43 (13 pairs) and 229E (14 pairs), showed no reactivity in either acute- or convalescent-phase serum with the newly isolated coronavirus by either the IFA test or the ELISA.

Example 5

Poly(A)+RNA Isolation and Northern Hybridization

This example illustrates a representative method of Northern hybrididization to detect SARS-CoV messages in Vero E6 cells.

Total RNA from infected or uninfected Vero E6 cells was isolated with Trizol reagent (Invitrogen Life Technologies, Carlsbad, Calif.) used according to the manufacturer's recommendations. Poly(A)+RNA was isolated from total RNA by use of the Oligotex Direct mRNA Kit (Qiagen, Inc., Santa Clarita, Calif.), following the instructions for the batch protocol, followed by ethanol precipitation. RNA isolated from 1 cm$^2$ of cells was separated by electrophoresis on a 0.9% agarose gel containing 3.7% formaldehyde, followed by partial alkaline hydrolysis (Ausubel et al. eds. *Current Protocols in Molecular Biology*, vol. 1, John Wiley & Sons, Inc., NY, N.Y., Ch. 4.9, 1996). RNA was transferred to a nylon membrane (Roche Molecular Biochemicals, Indianapolis, Ind.) by vacuum blotting (Bio-Rad, Hercules, Calif.) and fixed by UV cross-linking. The DNA template for probe synthesis was generated by RT-PCR amplification of SARS-CoV nt 29,083 to 29,608 (SEQ ID NO: 1), by using a reverse primer containing a T7 RNA polymerase promoter to facilitate generation of a negative-sense riboprobe. In vitro transcription of the digoxigenin-labeled riboprobe, hybridization, and detection of the bands were carried out with the digoxigenin system by using manufacturer's recommended procedures (Roche Molecular Biochemicals, Indianapolis, Ind.). Signals were visualized by chemiluminescence and detected with x-ray film.

Example 6

SARS-CoV Genome Organization

This example illustrates the genomic organization of the SARS-CoV genome, including the location of SARS-CoV ORFs.

The genome of SARS-CoV is a 29,727-nucleotide, polyadenylated RNA, and 41% of the residues are G or C (range for published coronavirus complete genome sequences, 37% to 42%). The genomic organization is typical of coronaviruses, having the characteristic gene order [5'-replicase (rep), spike (S), envelope (E), membrane (M), nucleocapsid (N)-3'] and short untranslated regions at both termini (FIG. 7A, Table 5). The SARS-CoV rep gene, which comprises approximately two-thirds of the genome, encodes two polyproteins (encoded by ORF1a and ORF1b) that undergo co-translational proteolytic processing. There are four ORFs downstream of rep that encode the structural proteins, S, E, M, and N, which are common to all known coronaviruses. The hemagglutinin-esterase gene, which is present between ORF1b and S in group 2 and some group 3 coronaviruses (Lai and Holmes, in *Fields Virology*, eds. Knipe and Howley, Lippincott Williams and Wilkins, New York, 4th edition, 2001, Ch. 35), was not found in SARS-CoV.

Coronaviruses also encode a number of non-structural proteins that are located between S and E, between M and N, or downstream of N. These non-structural proteins, which vary widely among the different coronavirus species, are of unknown function and are dispensable for virus replication (Lai and Holmes, in *Fields Virology*, eds. Knipe and Howley, Lippincott Williams and Wilkins, New York, 4th edition, 2001, Ch. 35). The genome of SARS-CoV contains ORFs for five non-structural proteins of greater than 50 amino acids (FIG. 7B, Table 5). Two overlapping ORFs encoding proteins of 274 and 154 amino acids (termed X1 (SEQ ID NO: 5) and X2 (SEQ ID NO: 6), respectively) are located between S (SEQ ID NO: 4) and E (SEQ ID NO: 7). Three additional non-structural genes, X3 (SEQ ID NO: 9), X4 (SEQ ID NO: 10), and X5 (SEQ ID NO: 11) (encoding proteins of 63, 122, and 84 amino acids, respectively), are located between M (SEQ ID NO: 8) and N (SEQ ID NO: 12). In addition to the five ORFs encoding the non-structural proteins described above, there are also two smaller ORFs between M and N, encoding proteins of less than 50 amino acids. Searches of the GenBank database (BLAST and FastA) indicated that there is no significant sequence similarity between these non-structural proteins of SARS-CoV and any other proteins.

The coronavirus rep gene products are translated from genomic RNA, but the remaining viral proteins are translated from subgenomic mRNAs that form a 3'-coterminal nested set, each with a 5'-end derived from the genomic 5'-leader sequence. The coronavirus subgenomic mRNAs are synthesized through a discontinuous transcription process, the mechanism of which has not been unequivocally established (Lai and Holmes, in *Fields Virology*, eds. Knipe and Howley, Lippincott Williams and Wilkins, New York, 4th edition, 2001, Ch. 35; Sawicki and Sawicki, *Adv. Exp. Med. Biol.* 440:215-19, 1998). The SARS-CoV leader sequence was mapped by comparing the sequence of 5'-RACE products synthesized from the N gene mRNA with those synthesized from genomic RNA. A sequence, AAACGAAC (nucleotides 65-72 of SEQ ID NO: 1), was identified immediately upstream of the site where the N gene mRNA and genomic sequences diverged. This sequence was also present upstream of ORF1a and immediately upstream of five other ORFs (Table 5), suggesting that it functions as the conserved core of the transcriptional regulatory sequence (TRS).

In addition to the site at the 5'-terminus of the genome, the TRS conserved core sequence appears six times in the remainder of the genome. The positions of the TRS in the genome of SARS-CoV predict that subgenomic mRNAs of 8.3, 4.5, 3.4, 2.5, 2.0, and 1.7 kb, not including the poly(A) tail, should be produced (FIGS. 7A-B, Table 5). At least five subgenomic mRNAs were detected by Northern hybridization of RNA from SARS-CoV-infected cells, using a probe derived from the 3'-untranslated region (FIG. 7C). The calculated sizes of the five predominant bands correspond to the sizes of five of the predicted subgenomic mRNAs of SARS-CoV; the possibility that other, low-abundance mRNAs are present cannot be excluded. By analogy with other coronaviruses (Lai and Holmes, in *Fields Virology*, eds. Knipe and Howley, Lippincott Williams and Wilkins, New York, 4th edition, 2001, Ch. 35), the 8.3-kb and 1.7-kb subgenomic mRNAs are monocistronic, directing translation of S and N, respectively, whereas multiple proteins are translated from the 4.5-kb (X1, X2, and E), 3.4-kb (M and X3), and 2.5-kb (X4 and X5) mRNAs. A consensus TRS is not found directly upstream of the ORF encoding the predicted E protein, and a monocistronic mRNA that would be predicted to code for E could not be clearly identified by Northern blot analysis. It is possible that the 3.6-kb band contains more than one mRNA species or that the monocistronic mRNA for E is a low-abundance message.

TABLE 5

Locations of SARS-CoV ORFs and sizes of proteins and mRNAs

| ORF | Genome Location | | | Predicted Size | |
| --- | --- | --- | --- | --- | --- |
| | TRS[a] | ORF Start | ORF End | Protein (aa) | mRNA (nt)[b] |
| 1a | 72 | 265 | 13,398 | 4,378 | 29,727 |
| 1b | | 13,398 | 21,482 | 2,695 | |
| S | 21,491 | 21,492 | 25,256 | 1,255 | 8,308[c] |
| X1 | 25,265 | 25,268 | 26,089 | 274 | 4,534[c] |
| X2 | | 25,689 | 26,150 | 154 | |
| E | | 26,117 | 26,344 | 76 | |
| M | 26,353 | 26,398 | 27,060 | 221 | 3,446[c] |
| X3 | | 27,074 | 27,262 | 63 | |
| X4 | 27,272 | 27,273 | 27,638 | 122 | 2,527[c] |
| X5 | 27,778 | 27,864 | 28,115 | 84 | 2,021[d] |
| N | 28,111 | 28,120 | 29,385 | 422 | 1,688[c] |

[a]The location is the 3'-most nucleotide in the consensus TRS, AAACGAAC.
[b]Not including poly(A). Predicted size is based on the position of the conserved TRS.
[c]Corresponding mRNA detected by Northern blot analysis (FIG. 7C)
[d]No mRNA corresponding to utilization of this consensus TRS was detected by Northern blot analysis (FIG. 7C)

Example 7

Real-Time RT-PCR Assay for SARS-CoV Detection

This example demonstrates the use of SARS-CoV-specific primers and probes in a real-time RT-PCR assay to detect SARS-CoV in patient specimens.

A variant of the real-time format, based on TaqMan probe hydrolysis technology (Applied Biosystems, Foster City, Calif.), was used to analyze a total of 340 clinical specimens collected from 246 persons with confirmed or suspected SARS-CoV infection. Specimens included oro- and nasopharyngeal swabs (dry and in viral transport media), sputa, nasal aspirates and washes, BAL, and lung tissue specimens collected at autopsy.

Nucleic Acid Extraction

SARS-CoV nucleic acids were recovered from clinical specimens using the automated NucliSens extraction system (bioMérieux, Durham, N.C.). Following manufacturer's instructions, specimens received in NucliSens lysis buffer were incubated at 37° C. for 30 min with intermittent mixing, and 50 µL of silica suspension, provided in the extraction kit, was added and mixed. The contents of the tube were then transferred to a nucleic acid extraction cartridge and processed on an extractor workstation. Approximately 40-50 µL of total nucleic acid eluate was recovered into nuclease-free vials and either tested immediately or stored at −70° C.

Primers and Probes

Multiple primer and probe sets were designed from the SARS-CoV polymerase 1b (nucleic acid 13,398 to 21,482 of SEQ ID NO: 1) and nucleocapsid gene (nucleic acid 28,120 to 29,385 of SEQ ID NO: 1) sequences by using Primer Express software version 1.5 or 2.0.0 (Applied Biosystems, Foster City, Calif.) with the following default settings: primer melting temperature ($T_M$) set at 60° C.; probe $T_M$ set at 10° C. greater than the primers at approximately 70° C.; and no guanidine residues permitted at the 5' probe termini. All primers and probes were synthesized by standard phosphoramidite chemistry techniques. TaqMan probes were labeled at the 5'-end with the reporter 6-FAM and at the 3'-end with the quencher Blackhole Quencher 1 (Biosearch Technologies, Inc., Novato, Calif.). Optimal primer and probe concentrations were determined by cross-titration of serial twofold dilutions of each primer against a constant amount of purified SARS-CoV RNA. Primer and probe concentrations that gave the highest amplification efficiencies were selected for further study (Table 6).

Real-Time RT-PCR Assay

The real-time RT-PCR assay was performed by using the Real-Time One-Step RT-PCR Master Mix (Applied Biosystems, Foster City, Calif.). Each 25-µL reaction mixture contained 12.5 µL of 2× Master Mix, 0.625 µL of the 40× MultiScribe and RNase Inhibitor mix, 0.25 µL of 10 µM probe, 0.25 µL each of 50 µM forward and reverse primers, 6.125 µL of nuclease-free water, and 5 µL of nucleic acid extract. Amplification was carried out in 96-well plates on an iCycler iQ Real-Time Detection System (Bio-Rad, Hercules, Calif.). Thermocycling conditions consisted of 30 minutes at 48° C. for reverse transcription, 10 minutes at 95° C. for activation of the AmpliTaq Gold DNA polymerase, and 45 cycles of 15 seconds at 95° C. and 1 minute at 60° C. Each run included one SARS-CoV genomic template control and at least two no-template controls for the extraction (to check for contamination during sample processing) and one no-template control for the PCR-amplification step. As a control for PCR inhibitors, and to monitor nucleic acid extraction efficiency, each sample was tested by real-time RT-PCR for the presence of the human ribonuclease (RNase) P gene (GenBank Accession No. NM_006413) by using the following primers and probe: forward primer 5'-AGATTTGGACCTGCGAGCG-3' (SEQ ID NO: 36); reverse primer 5'-GAGCGGCTGTCTCCACAAGT-3' (SEQ ID NO: 37); probe 5'-TTCTGACCTGAAGGCTCTGCGCG-3' (SEQ ID NO: 38). The assay reaction was performed identically to that described above except that primer concentrations used were 30 µM each. Fluorescence measurements were taken and the threshold cycle ($C_T$) value for each sample was calculated by determining the point at which fluorescence exceeded a threshold limit set at the mean plus 10 standard deviations above the baseline. A test result was considered positive if two or more of the SARS genomic targets showed positive results ($C_T \leq 45$ cycles) and all positive and negative control reactions gave expected values.

While this disclosure has been described with an emphasis upon preferred embodiments, it will be obvious to those of ordinary skill in the art that variations and equivalents of the preferred embodiments may be used and it is intended that the disclosure may be practiced otherwise than as specifically described herein. Accordingly, this disclosure includes all modifications encompassed within the spirit and scope of the disclosure as defined by the claims below.

TABLE 6

Primers and probes used for real-time RT-PCR assays[a]

| Assay ID | Primer/probe | Sequence | Genomic Region |
| --- | --- | --- | --- |
| Primary diagnostic assay | | | |
| SARS1 | F | CATGTGTGGCGGCTCACTATAT (SEQ ID NO: 16) | RNA Pol |
|  | R | GACACTATTAGCATAAGCAGTTGTAGCA (SEQ ID NO: 17) |  |
|  | P | TTAAACCAGGTGGAACATCATCCGGTG (SEQ ID NO: 18) |  |
| SARS2 | F | GGAGCCTTGAATACACCCAAAG (SEQ ID NO: 19) | Nucleocapsid |
|  | R | GCACGGTGGCAGCATTG (SEQ ID NO: 20) |  |
|  | P | CCACATTGGCACCCGCAATCC (SEQ ID NO: 21) |  |
| SARS3 | F | CAAACATTGGCCGCAAATT (SEQ ID NO: 22) | Nucleocapsid |
|  | R | CAATGCGTGACATTCCAAAGA (SEQ ID NO: 23) |  |
|  | P | CACAATTTGCTCCAAGTGCCTCTGCA (SEQ ID NO: 24) |  |
| To confirm positive results | | | |
| N3 | F | GAAGTACCATCTGGGGCTGAG (SEQ ID NO: 25) | Nucleocapsid |
|  | R | CCGAAGAGCTACCCGACG (SEQ ID NO: 26) |  |
|  | P | CTCTTTCATTTTGCCGTCACCACCAC (SEQ ID NO: 27) |  |
| 3'-NTR | F | AGCTCTCCCTAGCATTATTCACTG (SEQ ID NO: 28) | 3'-NTR |
|  | R | CACCACATTTTCATCGAGGC (SEQ ID NO: 29) |  |
|  | P | TACCCTCGATCGTACTCCGCGT (SEQ ID NO: 30) |  |
| M | F | TGTAGGCACTGATTCAGGTTTTG (SEQ ID NO: 31) | M protein |
|  | R | CGGCGTGGTCTGTATTTAATTTA (SEQ ID NO: 32) |  |
|  | P | CTGCATACAACCGCTACCGTATTGGAA (SEQ ID NO: 33) |  |

[a]RT-PCR, reverse transcription-polymerase chain reaction; F, forward primer; R, reverse primer; P, probe; NTR, nontranslated region.

The invention claimed is:

1. A method of detecting a severe acute respiratory syndrome-associated coronavirus (SARS-CoV) in a sample comprising:
   contacting the sample with a pair of nucleic acid primers that hybridize to a SARS-CoV nucleic acid, wherein at least one primer is 5'-end labeled with a reporter dye, and wherein at least one of the primers comprises the sequence as set forth in any one of SEQ ID NOs: 13-15;
   amplifying the SARS-CoV nucleic acid or a fragment thereof from the sample utilizing the pair of nucleic acid primers;
   electrophoresing the amplified products; and
   detecting the 5'-end labeled reporter dye, thereby detecting a SARS-CoV.

2. The method of claim 1, wherein the amplification utilizes reverse transcriptase-polymerase chain reaction.

3. A method of detecting a severe acute respiratory syndrome-associated coronavirus (SARS-CoV) in a sample, comprising:
   contacting the sample with a pair of nucleic acid primers that hybridize to a SARS-CoV nucleic acid, wherein at least one of the nucleic acid primers comprises the sequence as set forth in any one of SEQ ID NOs: 13-15;
   amplifying the SARS-CoV nucleic acid or a fragment thereof from the sample utilizing the pair of nucleic acid primers;
   adding to the amplified SARS-CoV nucleic acid or the fragment thereof a SARS-CoV probe that hybridizes to the SARS-CoV nucleic acid, wherein the SARS-CoV probe is labeled with a 5'-reporter dye and a 3'-quencher dye;
   performing one or more additional rounds of amplification with Taq DNA polymerase; and
   detecting fluorescence of the 5'-reporter dye, thereby detecting a SARS-CoV.

4. A kit for detecting a severe acute respiratory syndrome-associated coronavirus (SARS-CoV) in a sample, comprising a pair of nucleic acid primers that hybridize under stringent conditions to a SARS-CoV nucleic acid, wherein at least one of the primers comprises the sequence as set forth in any one of SEQ ID NOs: 13-15.

5. The kit of claim 4, wherein one primer is 5'-end labeled with a reporter dye.

6. The kit of claim 4, further comprising a SARS-CoV probe that hybridizes to the SARS-CoV nucleic acid amplified by the pair of primers, wherein the SARS-CoV probe is labeled with a 5'-reporter dye and a 3'-quencher dye.

7. The kit of claim 4, further comprising an isolated SARS-CoV organism.

* * * * *

SEQUENCE LISTING

<160> NUMBER OF SEQ ID NOS: 38

<210> SEQ ID NO 1
<211> LENGTH: 29727
<212> TYPE: DNA
<213> ORGANISM: Coronavirus
<220> FEATURE:
<221> NAME/KEY: misc_feature
<222> LOCATION: (265)..(13398)
<223> OTHER INFORMATION: ORF 1a
<220> FEATURE:
<221> NAME/KEY: misc_feature
<222> LOCATION: (13398)..(21482)
<223> OTHER INFORMATION: ORF 1b
<220> FEATURE:
<221> NAME/KEY: misc_feature
<222> LOCATION: (21492)..(25256)
<223> OTHER INFORMATION: ORF S
<220> FEATURE:
<221> NAME/KEY: misc_feature
<222> LOCATION: (25268)..(26089)
<223> OTHER INFORMATION: ORF X1
<220> FEATURE:
<221> NAME/KEY: misc_feature
<222> LOCATION: (25689)..(26150)
<223> OTHER INFORMATION: ORF X2
<220> FEATURE:
<221> NAME/KEY: misc_feature
<222> LOCATION: (26117)..(26344)
<223> OTHER INFORMATION: ORF E
<220> FEATURE:
<221> NAME/KEY: misc_feature
<222> LOCATION: (26398)..(27060)
<223> OTHER INFORMATION: ORF M
<220> FEATURE:
<221> NAME/KEY: misc_feature
<222> LOCATION: (27074)..(27262)
<223> OTHER INFORMATION: ORF X3
<220> FEATURE:
<221> NAME/KEY: misc_feature
<222> LOCATION: (27273)..(27638)
<223> OTHER INFORMATION: ORF X4
<220> FEATURE:
<221> NAME/KEY: misc_feature
<222> LOCATION: (27864)..(28115)
<223> OTHER INFORMATION: ORF X5
<220> FEATURE:
<221> NAME/KEY: misc_feature
<222> LOCATION: (28120)..(29385)
<223> OTHER INFORMATION: ORF N

<400> SEQUENCE: 1
ttattaggtt tttacctacc caggaaaagc caaccaacct cgatctcttg tagatctgtt      60
ctctaaacga actttaaaat ctgtgtagct gtcgctcggc tgcatgccta gtgcacctac     120
gcagtataaa caataataaa ttttactgtc gttgacaaga aacgagtaac tcgtccctct     180
tctgcagact gcttacggtt tcgtccgtgt tgcagtcgat catcagcata cctaggtttc     240
gtccgggtgt gaccgaaagg taagatggag agccttgttc ttggtgtcaa cgagaaaaca     300
cacgtccaac tcagtttgcc tgtccttcag gttagagacg tgctagtgcg tggcttcggg     360
gactctgtgg aagaggccct atcggaggca cgtgaacacc tcaaaaatgg cacttgtggt     420
ctagtagagc tggaaaaagg cgtactgccc cagcttgaac agccctatgt gttcattaaa     480
cgttctgatg ccttaagcac caatcacggc cacaaggtcg ttgagctggt tgcagaaatg     540
gacggcattc agtacggtcg tagcggtata acactgggag tactcgtgcc acatgtgggc     600
gaaaccccaa ttgcataccg caatgttctt cttcgtaaga acggtaataa gggagccggt     660
ggtcatagct atggcatcga tctaaagtct tatgacttag gtgacgagct tggcactgat     720

```
cccattgaag attatgaaca aaactggaac actaagcatg gcagtggtgc actccgtgaa    780
ctcactcgtg agctcaatgg aggtgcagtc actcgctatg tcgacaacaa tttctgtggc    840
ccagatgggt accctcttga ttgcatcaaa gattttctcg cacgcgcggg caagtcaatg    900
tgcactcttt ccgaacaact tgattacatc gagtcgaaga gaggtgtcta ctgctgccgt    960
gaccatgagc atgaaattgc ctggttcact gagcgctctg ataagagcta cgagcaccag   1020
acacccttcg aaattaagag tgccaagaaa tttgacactt caaagggga atgcccaaag    1080
tttgtgtttc ctcttaactc aaaagtcaaa gtcattcaac cacgtgttga aaagaaaaag   1140
actgagggtt tcatggggcg tatacgctct gtgtaccctg ttgcatctcc acaggagtgt   1200
aacaatatgc acttgtctac cttgatgaaa tgtaatcatt gcgatgaagt ttcatggcag   1260
acgtgcgact ttctgaaagc cacttgtgaa cattgtggca ctgaaaattt agttattgaa   1320
ggacctacta catgtgggta cctacctact aatgctgtag tgaaaatgcc atgtcctgcc   1380
tgtcaagacc cagagattgg acctgagcat agtgttgcag attatcacaa ccactcaaac   1440
attgaaactc gactccgcaa gggaggtagg actagatgtt ttggaggctg tgtgtttgcc   1500
tatgttggct gctataataa gcgtgcctac tgggttcctc gtgctagtgc tgatattggc   1560
tcaggccata ctggcattac tggtgacaat gtggagacct gaatgagga tctccttgag    1620
atactgagtc gtgaacgtgt taacattaac attgttggcg attttcattt gaatgaagag   1680
gttgccatca ttttggcatc tttctctgct tctacaagtg cctttattga cactataaag   1740
agtcttgatt acaagtcttt caaaaccatt gttgagtcct gcggtaacta taagttacc    1800
aagggaaagc ccgtaaaagg tgcttggaac attggacaac agagatcagt tttaacacca   1860
ctgtgtggtt ttccctcaca ggctgctggt gttatcagat caattttgc gcgcacactt   1920
gatgcagcaa accactcaat tcctgatttg caaagagcag ctgtcaccat acttgatggt   1980
atttctgaac agtcattacg tcttgtcgac gccatggttt atacttcaga cctgctcacc   2040
aacagtgtca ttattatggc atatgtaact ggtggtcttg tacaacagac ttctcagtgg   2100
ttgtctaatc ttttgggcac tactgttgaa aaactcaggc ctatctttga atggattgag   2160
gcgaaactta gtgcaggagt tgaatttctc aaggatgctt gggagattct caaatttctc   2220
attacaggtg ttttttgacat cgtcaagggt caaatacagg ttgcttcaga taacatcaag   2280
gattgtgtaa aatgcttcat tgatgttgtt aacaaggcac tcgaaatgtg cattgatcaa   2340
gtcactatcg ctggcgcaaa gttgcgatca ctcaacttag tgaagtctt catcgctcaa    2400
agcaagggac tttaccgtca gtgtatacgt ggcaaggagc agctgcaact actcatgcct   2460
cttaaggcac caaaagaagt aacctttctt gaaggtgatt cacatgacac agtacttacc   2520
tctgaggagg ttgttctcaa gaacggtgaa ctcgaagcac tcgagacgcc cgttgatagc   2580
ttcacaaatg gagctatcgt tggcacacca gtctgtgtaa atggcctcat gctcttagag   2640
attaaggaca agaacaata ctgcgcattg tctcctggtt tactggctac aaacaatgtc    2700
tttcgcttaa aaggggggtgc accaattaaa ggtgtaacct tgggagaaga tactgtttgg   2760
gaagttcaag gttacaagaa tgtgagaatc acatttgagc ttgatgaacg tgttgacaaa   2820
gtgcttaatg aaaagtgctc tgtctacact gttgaatccg gtaccgaagt tactgagttt   2880
gcatgtgttg tagcagaggc tgttgtgaag actttacaac cagtttctga tctccttacc   2940
aacatgggta ttgatcttga tgagtggagt gtagctacat tctacttatt tgatgatgct   3000
ggtgaagaaa acttttcatc acgtatgtat tgttcctttt accctccaga tgaggaagaa   3060
```

-continued

```
gaggacgatg cagagtgtga ggaagaagaa attgatgaaa cctgtgaaca tgagtacggt    3120
acagaggatg attatcaagg tctccctctg gaatttggtg cctcagctga aacagttcga    3180
gttgaggaag aagaagagga agactggctg gatgatacta ctgagcaatc agagattgag    3240
ccagaaccag aacctacacc tgaagaacca gttaatcagt ttactggtta tttaaaactt    3300
actgacaatg ttgccattaa atgtgttgac atcgttaagg aggcacaaag tgctaatcct    3360
atggtgattg taaatgctgc taacatacac ctgaaacatg gtggtggtgt agcaggtgca    3420
ctcaacaagg caaccaatgg tgccatgcaa aaggagagtg atgattacat taagctaaat    3480
ggccctctta cagtaggagg gtcttgtttg ctttctggac ataatcttgc taagaagtgt    3540
ctgcatgttg ttggacctaa cctaaatgca ggtgaggaca tccagcttct taaggcagca    3600
tatgaaaatt tcaattcaca ggacatctta cttgcaccat tgttgtcagc aggcatattt    3660
ggtgctaaac cacttcagtc tttacaagtg tgcgtgcaga cggttcgtac acaggtttat    3720
attgcagtca atgacaaagc tctttatgag caggttgtca tggattatct tgataacctg    3780
aagcctagag tggaagcacc taaacaagag gagccaccaa acacagaaga ttccaaaact    3840
gaggagaaat ctgtcgtaca gaagcctgtc gatgtgaagc caaaaattaa ggcctgcatt    3900
gatgaggtta ccacaacact ggaagaaact aagtttctta ccaataagtt actcttgttt    3960
gctgatatca atggtaagct ttaccatgat tctcagaaca tgcttagagg tgaagatatg    4020
tctttccttg agaaggatgc accttacatg gtaggtgatg ttatcactag tggtgatatc    4080
acttgtgttg taatacccctc caaaaaggct ggtggcacta ctgagatgct ctcaagagct    4140
ttgaagaaag tgccagttga tgagtatata accacgtacc ctggacaagg atgtgctggt    4200
tatacacttg aggaagctaa gactgctctt aagaaatgca aatctgcatt ttatgtacta    4260
ccttcagaag cacctaatgc taaggaagag attctaggaa ctgtatcctg gaatttgaga    4320
gaaatgcttg ctcatgctga agagacaaga aaattaatgc ctatatgcat ggatgttaga    4380
gccataatgg caaccatcca acgtaagtat aaaggaatta aaattcaaga gggcatcgtt    4440
gactatggtg tccgattctt cttttatact agtaaagagc tgtagcttc tattattacg     4500 aagctgaact ctctaaatga gccgcttgtc acaatgccaa ttggttatgt gacacatggt    4560
tttaatcttg aagaggctgc gcgctgtatg cgttctctta agctcctgc cgtagtgtca     4620 gtatcatcac cagatgctgt tactacatat aatggatacc tcacttcgtc atcaaagaca    4680
tctgaggagc actttgtaga aacagtttct ttggctggct cttacagaga ttggtcctat    4740
tcaggacagc gtacagagtt aggtgttgaa tttcttaagc gtggtgacaa aattgtgtac    4800
cacactctgg agagccccgt cgagtttcat cttgacggtg aggttctttc acttgacaaa    4860
ctaaagagtc tcttatccct gcgggaggtt aagactataa aagtgttcac aactgtggac    4920
aacactaatc tccacacaca gcttgtggat atgtctatga catatggaca gcagtttggt    4980
ccaacatact tggatggtgc tgatgttaca aaaattaaac tcatgtaaa tcatgagggt     5040 aagactttct ttgtactacc tagtgatgac acactacgta gtgaagcttt cgagtactac    5100
catactcttg atgagagttt tcttggtagg tacatgtctg ctttaaacca cacaaagaaa    5160
tggaaatttc ctcaagttgg tggtttaact tcaattaaat gggctgataa caattgttat    5220
ttgtctagtg ttttattagc acttcaacag cttgaagtca aattcaatgc accagcactt    5280
caagaggctt attatagagc ccgtgctggt gatgctgcta acttttgtgc actcatactc    5340
gcttacagta ataaaactgt tggcgagctt ggtgatgtca gagaaactat gacccatctt    5400
ctacagcatg ctaatttgga atctgcaaag cgagttctta atgtggtgtg taaacattgt    5460
```

```
ggtcagaaaa ctactacctt aacgggtgta gaagctgtga tgtatatggg tactctatct    5520
tatgataatc ttaagacagg tgtttccatt ccatgtgtgt gtggtcgtga tgctacacaa    5580
tatctagtac aacaagagtc ttcttttgtt atgatgtctg caccacctgc tgagtataaa    5640
ttacagcaag gtacattctt atgtgcgaat gagtacactg gtaactatca gtgtggtcat    5700
tacactcata taactgctaa ggagaccctc tatcgtattg acggagctca ccttacaaag    5760
atgtcagagt acaaaggacc agtgactgat gttttctaca aggaaacatc ttacactaca    5820
accatcaagc ctgtgtcgta taaactcgat ggagttactt acacagagat tgaaccaaaa    5880
ttggatgggt attataaaaa ggataatgct tactatacag agcagcctat agaccttgta    5940
ccaactcaac cattaccaaa tgcgagtttt gataatttca aactcacatg ttctaacaca    6000
aaatttgctg atgatttaaa tcaaatgaca ggcttcacaa agccagcttc acgagagcta    6060
tctgtcacat tcttcccaga cttgaatggc gatgtagtgg ctattgacta tagacactat    6120
tcagcgagtt tcaagaaagg tgctaaatta ctgcataagc caattgtttg gcacattaac    6180
caggctacaa ccaagacaac gttcaaacca aacacttggt gtttacgttg tctttggagt    6240
acaaagccag tagatacttc aaattcattt gaagttctgg cagtagaaga cacacaagga    6300
atggacaatc ttgcttgtga aagtcaacaa cccacctctg aagaagtagt ggaaaatcct    6360
accatacaga aggaagtcat agagtgtgac gtgaaaacta ccgaagttgt aggcaatgtc    6420
atacttaaac catcagatga aggtgttaaa gtaacacaag agttaggtca tgaggatctt    6480
atggctgctt atgtggaaaa cacaagcatt accattaaga aacctaatga ctttcacta    6540 gccttaggtt taaaaacaat tgccactcat ggtattgctg caattaatag tgttccttgg    6600
agtaaaattt tggcttatgt caaaccattc ttaggacaag cagcaattac aacatcaaat    6660
tgcgctaaga gattagcaca acgtgtgttt aacaattata tgccttatgt gtttacatta    6720
ttgttccaat tgtgtacttt tactaaaagt accaattcta gaattagagc ttcactacct    6780
acaactattg ctaaaaatag tgttaagagt gttgctaaat tatgtttgga tgccggcatt    6840
aattatgtga agtcacccaa attttctaaa ttgttcacaa tcgctatgtg gctattgttg    6900
ttaagtattt gcttaggttc tctaatctgt gtaactgctg cttttggtgt actcttatct    6960
aattttggtg ctccttctta ttgtaatggc gttagagaat tgtatcttaa ttcgtctaac    7020
gttactacta tggatttctg tgaaggttct tttccttgca gcatttgttt aagtggatta    7080
gactcccttg attcttatcc agctcttgaa accattcagg tgacgatttc atcgtacaag    7140
ctagacttga caattttagg tctggccgct gagtgggttt tggcatatat gttgttcaca    7200
aaattctttt atttattagg tctttcagct ataatgcagg tgttctttgg ctattttgct    7260
agtcatttca tcagcaattc ttggctcatg tggtttatca ttagtattgt acaaatggca    7320
cccgtttctg caatggttag gatgtacatc ttctttgctt cttctactac atatggaag    7380 agctatgttc atatcatgga tggttgcacc tcttcgactt gcatgatgtg ctataagcgc    7440
aatcgtgcca cacgcgttga gtgtacaact attgttaatg gcatgaagag atctttctat    7500
gtctatgcaa atggaggccg tggcttctgc aagactcaca attggaattg tctcaattgt    7560
gacacatttt gcactggtag tacattcatt agtgatgaag ttgctcgtga tttgtcactc    7620
cagtttaaaa gaccaatcaa ccctactgac cagtcatcgt atattgttga tagtgttgct    7680
gtgaaaaatg cgcgcttca cctctacttt gacaaggctg tcaaaagac ctatgagaga    7740 catccgctct cccatttgt caatttgac aatttgagag ctaacaacac taaaggttca    7800
```

-continued

```
ctgcctatta atgtcatagt ttttgatggc aagtccaaat gcgacgagtc tgcttctaag    7860
tctgcttctg tgtactacag tcagctgatg tgccaaccta ttctgttgct tgaccaagtt    7920
cttgtatcag acgttggaga tagtactgaa gtttccgtta agatgtttga tgcttatgtc    7980
gacaccttt cagcaacttt tagtgttcct atggaaaaac ttaaggcact tgttgctaca    8040
gctcacagcg agttagcaaa gggtgtagct ttagatggtg tcctttctac attcgtgtca    8100
gctgcccgac aaggtgttgt tgataccgat gttgacacaa aggatgttat tgaatgtctc    8160
aaactttcac atcactctga cttagaagtg acaggtgaca gttgtaacaa tttcatgctc    8220
acctataata aggttgaaaa catgacgccc agagatcttg gcgcatgtat tgactgtaat    8280
gcaaggcata tcaatgccca agtagcaaaa agtcacaatg tttcactcat ctggaatgta    8340
aaagactaca tgtcttatc tgaacagctg cgtaaacaaa ttcgtagtgc tgccaagaag    8400
aacaacatac cttttagact aacttgtgct acaactagac aggttgtcaa tgtcataact    8460
actaaaatct cactcaaggg tggtaagatt gttagtactt gttttaaact tatgcttaag    8520
gccacattat tgtgcgttct tgctgcattg gtttgttata tcgttatgcc agtacataca    8580
ttgtcaatcc atgatggtta cacaaatgaa atcattggtt acaaagccat tcaggatggt    8640
gtcactcgtg acatcatttc tactgatgat tgttttgcaa ataaacatgc tggttttgac    8700
gcatggttta gccagcgtgg tggttcatac aaaaatgaca aaagctgccc tgtagtagct    8760
gctatcatta aagagagat tggtttcata gtgcctggct taccgggtac tgtgctgaga    8820
gcaatcaatg tgacttctt gcattttcta cctcgtgttt ttagtgctgt tggcaacatt    8880
tgctacacac cttccaaact cattgagtat agtgattttg ctacctctgc ttgcgttctt    8940
gctgctgagt gtacaatttt taaggatgct atgggcaaac tgtgccata ttgttatgac    9000
actaatttgc tagagggttc tatttcttat agtgagcttc gtccagacac tcgttatgtg    9060
cttatggatg gttccatcat acagtttcct aacacttacc tggagggttc tgttagagta    9120
gtaacaactt ttgatgctga gtactgtaga catggtacat gcgaaaggtc agaagtaggt    9180
atttgcctat ctaccagtgg tagatgggtt cttaataatg agcattacag agctctatca    9240
ggagttttct gtggtgttga tgcgatgaat ctcatagcta acatctttac tcctcttgtg    9300
caacctgtgg gtgctttaga tgtgtctgct tcagtagtgg ctggtggtat tattgccata    9360
ttggtgactt gtgctgccta ctactttatg aaattcagac gtgtttttgg tgagtacaac    9420
catgttgttg ctgctaatgc actttttgtt ttgatgtctt tcactatact ctgtctggta    9480
ccagcttaca gctttctgcc gggagtctac tcagtctttt acttgtactt gacattctat    9540
ttcaccaatg atgtttcatt cttggctcac cttcaatggt ttgccatgtt ttctcctatt    9600
gtgccttttt ggataacagc aatctatgta ttctgtattt ctctgaagca ctgccattgg    9660
ttctttaaca actatcttag gaaaagagtc atgtttaatg gagttacatt tagtaccttc    9720
gaggaggctg ctttgtgtac ctttttgctc aacaaggaaa tgtacctaaa attgcgtagc    9780
gagacactgt tgccacttac acagtataac aggtatcttg ctctatataa caagtacaag    9840
tatttcagtg gagccttaga tactaccagc tatcgtgaag cagcttgctg ccacttagca    9900
aaggctctaa atgactttag caactcaggt gctgatgttc tctaccaacc accacagaca    9960
tcaatcactt ctgctgttct gcagagtggt tttaggaaaa tggcattccc gtcaggcaaa    10020
gttgaagggt gcatggtaca agtaacctgt ggaactacaa ctcttaatgg attgtggttg    10080
gatgacacag tatactgtcc aagacatgtc atttgcacag cagaagacat gcttaatcct    10140
aactatgaag atctgctcat tcgcaaatcc aaccatagct ttcttgttca ggctggcaat    10200
```

```
gttcaacttc gtgttattgg ccattctatg caaaattgtc tgcttaggct taaagttgat    10260
acttctaacc ctaagacacc caagtataaa tttgtccgta tccaacctgg tcaaacattt    10320
tcagttctag catgctacaa tggttcacca tctggtgttt atcagtgtgc catgagacct    10380
aatcatacca ttaaaggttc tttccttaat ggatcatgtg gtagtgttgg ttttaacatt    10440
gattatgatt gcgtgtcttt ctgctatatg catcatatgg agcttccaac aggagtacac    10500
gctggtactg acttagaagg taaattctat ggtccatttg ttgacagaca aactgcacag    10560
gctgcaggta cagacacaac cataacatta aatgttttgg catggctgta tgctgctgtt    10620
atcaatggtg ataggtggtt tcttaataga ttcaccacta ctttgaatga ctttaacctt    10680
gtggcaatga agtacaacta tgaacctttg acacaagatc atgttgacat attgggacct    10740
cttttctgct caaacaggaa tgccgtctta gatatgtgtg ctgctttgaa agagctgctg    10800
cagaatggta tgaatggtcg tactatcctt ggtagcacta ttttagaaga tgagtttaca    10860
ccatttgatg ttgttagaca atgctctggt gttaccttcc aaggtaagtt caagaaaatt    10920
gttaagggca ctcatcattg gatgcttttta actttcttga catcactatt gattcttgtt    10980
caaagtacac agtggtcact gttttttcttt gtttacgaga atgctttctt gccatttact    11040
cttggtatta tggcaattgc tgcatgtgct atgctgcttg ttaagcataa gcacgcattc    11100
ttgtgcttgt ttctgttacc ttctcttgca acagttgctt actttaatat ggtctacatg    11160
cctgctagct gggtgatgcg tatcatgaca tggcttgaat tggctgacac tagcttgtct    11220
ggttataggc ttaaggattg tgttatgtat gcttcagctt tagttttgct tattctcatg    11280
acagctcgca ctgtttatga tgatgctgct agacgtgttt ggacactgat gaatgtcatt    11340
acacttgttt acaaagtcta ctatggtaat gctttagatc aagctatttc catgtgggcc    11400
ttagttattt ctgtaacctc taactattct ggtgtcgtta cgactatcat gtttttagct    11460
agagctctag tgtttgtgtg tgttgagtat tacccattgt tatttattac tggcaacacc    11520
ttacagtgta tcatgcttgt ttattgtttc ttaggctatt gttgctgctg ctactttggc    11580
cttttctgtt tactcaaccg ttacttcagg cttactcttg gtgtttatga ctacttggtc    11640
tctacacaag aatttaggta tatgaactcc caggggcttt tgcctcctaa gagtagtatt    11700
gatgctttca agcttaacat taagttgttg ggtattggag gtaaaccatg tatcaaggtt    11760
gctactgtac agtctaaaat gtctgacgta aagtgcacat ctgtggtact gctctcggtt    11820
cttcaacaac ttagagtaga gtcatcttct aaaattgtgg gcacaatgtgt acaactccac    11880 aatgatattc ttcttgcaaa agacacaact gaagctttcg agaagatggt ttctcttttg    11940
tctgttttgc tatccatgca gggtgctgta gacattaata ggttgtgcga ggaaatgctc    12000
gataaccgtg ctactcttca ggctattgct tcagaattta gttctttacc atcatatgcc    12060
gcttatgcca ctgcccagga ggcctatgag caggctgtag ctaatggtga ttctgaagtc    12120
gttctcaaaa agttaaagaa atctttgaat gtggctaaat ctgagtttga ccgtgatgct    12180
gccatgcaac gcaagttgga aaagatggca gatcaggcta tgacccaaat gtacaaacag    12240
gcaagatctg aggacaagag ggcaaaagta actagtgcta tgcaaacaat gctcttcact    12300
atgcttagga agcttgataa tgatgcactt aacaacatta tcaacaatgc gcgtgatggt    12360
tgtgttccac tcaacatcat accattgact acagcagcca aactcatggt tgttgtccct    12420
gattatggta cctacaagaa cacttgtgat ggtaacacct ttacatatgc atctgcactc    12480
tgggaaatcc agcaagttgt tgatgcggat agcaagatta ttcaacttag tgaaattaac    12540
```

```
atggacaatt caccaaattt ggcttggcct cttattgtta cagctctaag agccaactca    12600
gctgttaaac tacagaataa tgaactgagt ccagtagcac tacgacagat gtcctgtgcg    12660
gctggtacca cacaaacagc ttgtactgat gacaatgcac ttgcctacta taacaattcg    12720
aagggaggta ggtttgtgct ggcattacta tcagaccacc aagatctcaa atgggctaga    12780
ttccctaaga gtgatggtac aggtacaatt tacacagaac tggaaccacc ttgtaggttt    12840
gttacagaca caccaaaagg gcctaaagtg aaatacttgt acttcatcaa aggcttaaac    12900
aacctaaata gaggtatggt gctgggcagt ttagctgcta cagtacgtct tcaggctgga    12960
aatgctacag aagtacctgc caattcaact gtgctttcct tctgtgcttt tgcagtagac    13020
cctgctaaag catataagga ttacctagca agtggaggac aaccaatcac caactgtgtg    13080
aagatgttgt gtacacacac tggtacagga caggcaatta ctgtaacacc agaagctaac    13140
atggaccaag agtcctttgg tggtgcttca tgttgtctgt attgtagatg ccacattgac    13200
catccaaatc ctaaaggatt ctgtgacttg aaaggtaagt acgtccaaat acctaccact    13260
tgtgctaatg acccagtggg ttttacactt agaaacacag tctgtaccgt ctgcggaatg    13320
tggaaaggtt atggctgtag ttgtgaccaa ctccgcgaac ccttgatgca gtctgcggat    13380
gcatcaacgt ttttaaacgg gtttgcggtg taagtgcagc ccgtcttaca ccgtgcggca    13440
caggcactag tactgatgtc gtctacaggg cttttgatat ttacaacgaa aaagttgctg    13500
gttttgcaaa gttcctaaaa actaattgct gtcgcttcca ggagaaggat gaggaaggca    13560
atttattaga ctcttacttt gtagttaaga ggcatactat gtctaactac aacatgaag     13620 agactattta aacttggtt aaagattgtc cagcggttgc tgtccatgac ttttttcaagt    13680 ttagagtaga tggtgacatg gtaccacata tatcacgtca gcgtctaact aaatacacaa    13740
tggctgattt agtctatgct ctacgtcatt ttgatgaggg taattgtgat acattaaaag    13800
aaatactcgt cacatacaat tgctgtgatg atgattattt caataagaag gattggtatg    13860
acttcgtaga gaatcctgac atcttacgcg tatatgctaa cttaggtgag cgtgtacgcc    13920
aatcattatt aaagactgta caattctgcg atgctatgcg tgatgcaggc attgtaggcg    13980
tactgacatt agataatcag gatcttaatg ggaactggta cgatttcggt gatttcgtac    14040
aagtagcacc aggctgcgga gttcctattg tggattcata ttactcattg ctgatgccca    14100
tcctcacttt gactagggca ttggctgctg agtcccatat ggatgctgat ctcgcaaaac    14160
cacttattaa gtgggatttg ctgaaatatg attttacgga agagagactt gtctcttcg    14220 accgttattt taaatattgg gaccagacat accatcccaa ttgtattaac tgtttggatg    14280
ataggtgtat ccttcattgt gcaaacttta atgtgttatt ttctactgtg tttccaccta    14340
caagttttgg accactagta agaaaaatat tgtagatgg tgttcctttt gttgtttcaa     14400
ctggatacca ttttcgtgag ttaggagtcg tacataatca ggatgtaaac ttacatagct    14460
cgcgtctcag tttcaaggaa cttttagtgt atgctgctga tccagctatg catgcagctt    14520
ctggcaattt attgctagat aaacgcacta catgctttc agtagctgca ctaacaaaca    14580
atgttgcttt tcaaactgtc aaacccggta attttaataa agacttttat gactttgctg    14640
tgtctaaagg tttctttaag gaaggaagtt ctgttgaact aaaacacttc ttctttgctc    14700
aggatggcaa cgctgctatc agtgattatg actattatcg ttataatctg ccaacaatgt    14760
gtgatatcag acaactccta ttcgtagttg aagttgttga taaatacttt gattgttacg    14820
atggtggctg tattaatgcc aaccaagtaa tcgttaacaa tctggataaa tcagctggtt    14880
tcccatttaa taaatggggt aaggctagac tttattatga ctcaatgagt tatgaggatc    14940
```

-continued

```
aagatgcact tttcgcgtat actaagcgta atgtcatccc tactataact caaatgaatc  15000
ttaagtatgc cattagtgca aagaatagag ctcgcaccgt agctggtgtc tctatctgta  15060
gtactatgac aaatagacag tttcatcaga aattattgaa gtcaatagcc gccactagag  15120
gagctactgt ggtaattgga acaagcaagt tttacggtgg ctggcataat atgttaaaaa  15180
ctgtttacag tgatgtagaa actccacacc ttatgggttg ggattatcca aaatgtgaca  15240
gagccatgcc taacatgctt aggataatgg cctctcttgt tcttgctcgc aaacataaca  15300
cttgctgtaa cttatcacac cgtttctaca ggttagctaa cgagtgtgcg caagtattaa  15360
gtgagatggt catgtgtggc ggctcactat atgttaaacc aggtggaaca tcatccggtg  15420
atgctacaac tgcttatgct aatagtgtct ttaacatttg tcaagctgtt acagccaatg  15480
taaatgcact tctttcaact gatggtaata agatagctga caagtatgtc cgcaatctac  15540
aacacaggct ctatgagtgt ctctatagaa atagggatgt tgatcatgaa ttcgtggatg  15600
agttttacgc ttacctgcgt aaacatttct ccatgatgat tctttctgat gatgccgttg  15660
tgtgctataa cagtaactat gcggctcaag gtttagtagc tagcattaag aactttaagg  15720
cagttctttta ttatcaaaat aatgtgttca tgtctgaggc aaaatgttgg actgagactg  15780
accttactaa aggacctcac gaattttgct cacagcatac aatgctagtt aaacaaggag  15840
atgattacgt gtacctgcct tacccagatc catcaagaat attaggcgca ggctgttttg  15900
tcgatgatat tgtcaaaaca gatggtacac ttatgattga aggttcgtg tcactggcta  15960
ttgatgctta cccacttaca aaacatccta atcaggagta tgctgatgtc tttcacttgt  16020
atttacaata cattagaaag ttacatgatg agcttactgg ccacatgttg gacatgtatt  16080
ccgtaatgct aactaatgat aacacctcac ggtactggga acctgagttt tatgaggcta  16140
tgtacacacc acatacagtc ttgcaggctg taggtgcttg tgtattgtgc aattcacaga  16200
cttcacttcg ttgcggtgcc tgtattagga gaccattcct atgttgcaag tgctgctatg  16260
accatgtcat ttcaacatca cacaaattag tgttgtctgt taatccctat gtttgcaatg  16320
ccccaggttg tgatgtcact gatgtgacac aactgtatct aggaggtatg agctattatt  16380
gcaagtcaca taagcctccc attagttttc cattatgtgc taatggtcag gtttttggtt  16440
tatacaaaaa cacatgtgta ggcagtgaca atgtcactga cttcaatgcg atagcaacat  16500
gtgattggac taatgctggc gattacatac ttgccaacac ttgtactgag agactcaagc  16560
ttttcgcagc agaaacgctc aaagccactg aggaaacatt taagctgtca tatggtattg  16620
ctactgtacg cgaagtactc tctgacagag aattgcatct ttcatgggag gttggaaaac  16680
ctagaccacc attgaacaga aactatgtct ttactggtta ccgtgtaact aaaaatagta  16740
aagtacagat tggagagtac accttttgaaa aaggtgacta tggtgatgct gttgtgtaca  16800
gaggtactac gacatacaag ttgaatgttg gtgattactt tgtgttgaca tctcacactg  16860
taatgccact tagtgcacct actctagtgc cacaagagca ctatgtgaga attactggct  16920
tgtacccaac actcaacatc tcagatgagt tttctagcaa tgttgcaaat tatcaaaagg  16980
tcggcatgca aaagtactct acactccaag gaccacctgg tactggtaag agtcattttg  17040
ccatcggact tgctctctat tacccatctg ctcgcatagt gtatacggca tgctctcatg  17100
cagctgttga tgccctatgt gaaaaggcat taaaatattt gcccatagat aaatgtagta  17160
gaatcatacc tgcgcgtgcg cgcgtagagt gttttgataa attcaaagtg aattcaacac  17220
tagaacagta tgttttctgc actgtaaatg cattgccaga aacaactgct gacattgtag  17280
```

```
tctttgatga aatctctatg gctactaatt atgacttgag tgttgtcaat gctagacttc    17340
gtgcaaaaca ctacgtctat attggcgatc ctgctcaatt accagccccc cgcacattgc    17400
tgactaaagg cacactagaa ccagaatatt ttaattcagt gtgcagactt atgaaaacaa    17460
taggtccaga catgttcctt ggaacttgtc gccgttgtcc tgctgaaatt gttgacactg    17520
tgagtgcttt agtttatgac aataagctaa aagcacacaa ggataagtca gctcaatgct    17580
tcaaaatgtt ctacaaaggt gttattacac atgatgtttc atctgcaatc aacagacctc    17640
aaataggcgt tgtaagagaa tttcttacac gcaatcctgc ttggagaaaa gctgttttta    17700
tctcacctta taattcacag aacgctgtag cttcaaaaat cttaggattg cctacgcaga    17760
ctgttgattc atcacagggt tctgaatatg actatgtcat attcacacaa actactgaaa    17820
cagcacactc ttgtaatgtc aaccgcttca atgtggctat cacaagggca aaaattggca    17880
ttttgtgcat aatgtctgat agagatcttt atgacaaact gcaatttaca agtctagaaa    17940
taccacgtcg caatgtggct acattacaag cagaaaatgt aactggactt tttaaggact    18000
gtagtaagat cattactggt cttcatccta cacaggcacc tacacacctc agcgttgata    18060
taaagttcaa gactgaagga ttatgtgttg acataccagg cataccaaag gacatgacct    18120
accgtagact catctctatg atgggtttca aaatgaatta ccaagtcaat ggttacccta    18180
atatgtttat cacccgcgaa gaagctattc gtcacgttcg tgcgtggatt ggctttgatg    18240
tagagggctg tcatgcaact agagatgctg tgggtactaa cctacctctc cagctaggat    18300
tttctacagg tgttaactta gtagctgtac cgactggtta tgttgacact gaaaataaca    18360
cagaattcac cagagttaat gcaaaacctc caccaggtga ccagtttaaa catcttatac    18420
cactcatgta taaaggcttg ccctggaatg tagtgcgtat taagatagta caaatgctca    18480
gtgatacact gaaaggattg tcagacagag tcgtgttcgt cctttgggcg catggctttg    18540
agcttacatc aatgaagtac tttgtcaaga ttggacctga agaacgtgt tgtctgtgtg    18600
acaaacgtgc aacttgcttt tctacttcat cagatactta tgcctgctgg aatcattctg    18660
tgggttttga ctatgtctat aacccattta tgattgatgt tcagcagtgg ggctttacgg    18720
gtaaccttca gagtaaccat gaccaacatt gccaggtaca tggaaatgca catgtggcta    18780
gttgtgatgc tatcatgact agatgtttag cagtccatga gtgctttgtt aagcgcgttg    18840
attggtctgt tgaataccct attataggag atgaactgag ggttaattct gcttgcagaa    18900
aagtacaaca catggttgtg aagtctgcat tgcttgctga taagttttca gttcttcatg    18960
acattggaaa tccaaaggct atcaagtgtg tgcctcaggc tgaagtagaa tggaagttct    19020
acgatgctca gccatgtagt gacaaagctt acaaaataga ggagctcttc tattcttatg    19080
ctacacatca cgataaattc actgatggtg tttgtttgtt ttggaattgt aacgttgatc    19140
gttacccagc caatgcaatt gtgtgtaggt ttgacacaag agcttgtca aacttgaact    19200
taccaggctg tgatggtggt agtttgtatg tgaataagca tgcattccac actccagctt    19260
tcgataaaag tgcatttact aatttaaagc aattgccttt cttttactat tctgatagtc    19320
cttgtgagtc tcatggcaaa caagtagtgt cggatattga ttatgttcca ctcaaatctg    19380
ctacgtgtat tacacgatgc aatttaggtg gtgctgtttg cagacaccat gcaaatgagt    19440
accgacagta cttggatgca tataatatga tgatttctgc tggatttagc ctatggattt    19500
acaaacaatt tgatacttat aacctgtgga atacatttac caggttacag agtttagaaa    19560
atgtggctta taatgttgtt aataaaggac actttgatgg acacgccggc gaagcacctg    19620
tttccatcat taataatgct gtttacacaa aggtagatgg tattgatgtg gagatctttg    19680
```

```
aaaataagac aacacttcct gttaatgttg catttgagct ttgggctaag cgtaacatta   19740
aaccagtgcc agagattaag atactcaata atttgggtgt tgatatcgct gctaatactg   19800
taatctggga ctacaaaaga gaagccccag cacatgtatc tacaataggt gtctgcacaa   19860
tgactgacat tgccaagaaa cctactgaga gtgcttgttc ttcacttact gtcttgtttg   19920
atggtagagt ggaaggacag gtagacccttt ttagaaacgc ccgtaatggt gttttaataa   19980
cagaaggttc agtcaaaggt ctaacacctt caaagggacc agcacaagct agcgtcaatg   20040
gagtcacatt aattggagaa tcagtaaaaa cacagtttaa ctactttaag aaagtagacg   20100
gcattattca acagttgcct gaaacctact ttactcagag cagagactta gaggatttta   20160
agcccagatc acaaatggaa actgactttc tcgagctcgc tatggatgaa ttcatacagc   20220
gatataagct cgagggctat gccttcgaac acatcgttta tggagatttc agtcatggac   20280
aacttggcgg tcttcattta atgataggct tagccaagcg ctcacaagat tcaccactta   20340
aattagagga ttttatccct atggacagca cagtgaaaaa ttacttcata acagatgcgc   20400
aaacaggttc atcaaaatgt gtgtgttctg tgattgatct tttacttgat gactttgtcg   20460
agataataaa gtcacaagat ttgtcagtga tttcaaaagt ggtcaaggtt acaattgact   20520
atgctgaaat ttcattcatg ctttggtgta aggatggaca tgttgaaacc ttctacccaa   20580
aactacaagc aagtcaagcg tggcaaccag gtgttgcgat gcctaacttg tacaagatgc   20640
aaagaatgct tcttgaaaag tgtgaccttc agaattatgg tgaaaatgct gttataccaa   20700
aaggaataat gatgaatgtc gcaaagtata ctcaactgtg tcaatactta aatacactta   20760
ctttagctgt accctacaac atgagagtta ttcactttgg tgctggctct gataaaggag   20820
ttgcaccagg tacagctgtg ctcagacaat ggttgccaac tggcacacta cttgtcgatt   20880
cagatcttaa tgacttcgtc tccgacgcag attctacttt aattggagac tgtgcaacag   20940
tacatacggc taataaatgg gaccttatta ttagcgatat gtatgaccct aggaccaaac   21000
atgtgacaaa agagaatgac tctaaagaag ggttttcac ttatctgtgt ggatttataa   21060
agcaaaaact agccctgggt ggttctatag ctgtaaagat aacagagcat tcttggaatg   21120 ctgacctta caagcttatg ggccatttct catggtggac agcttttgtt acaaatgtaa   21180
atgcatcatc atcggaagca ttttaattg gggctaacta tcttggcaag ccgaaggaac   21240
aaattgatgg ctataccatg catgctaact acatttctg gaggaacaca atcctatcc   21300 agttgtcttc ctattcactc tttgacatga gcaaatttcc tcttaaatta agaggaactg   21360
ctgtaatgtc tcttaaggag aatcaaatca atgatatgat ttattctctt ctggaaaaag   21420
gtaggcttat cattagagaa aacaacgag ttgtggtttc aagtgatatt cttgttaaca   21480
actaaacgaa catgtttatt ttcttattat ttcttactct cactagtggt agtgaccttg   21540
accggtgcac cacttttgat gatgttcaag ctcctaatta cactcaacat acttcatcta   21600
tgaggggggt ttactatcct gatgaaattt ttagatcaga cactctttat ttaactcagg   21660
atttatttct tccatttat tctaatgtta cagggtttca tactattaat catacgtttg   21720
gcaaccctgt catacctttt aaggatggta tttattttgc tgccacagag aaatcaaatg   21780
ttgtccgtgg ttgggttttt ggttctacca tgaacaacaa gtcacagtcg gtgattatta   21840
ttaacaattc tactaatgtt gttatacgag catgtaactt tgaattgtgt gacaacccct   21900
tctttgctgt ttctaaaccc atgggtacac agacacatac tatgatattc gataatgcat   21960
ttaattgcac tttcgagtac atatctgatg ccttttcgct tgatgtttca gaaaagtcag   22020
```

```
gtaatttttaa acacttacga gagtttgtgt ttaaaaataa agatgggttt ctctatgttt    22080
ataagggcta tcaacctata gatgtagttc gtgatctacc ttctggtttt aacactttga    22140
aacctatttt taagttgcct cttggtatta acattacaaa ttttagagcc attcttacag    22200
ccttttcacc tgctcaagac atttggggca cgtcagctgc agcctatttt gttggctatt    22260
taaagccaac tacatttatg ctcaagtatg atgaaaatgg tacaatcaca gatgctgttg    22320
attgttctca aaatccactt gctgaactca atgctctgt taagagcttt gagattgaca     22380
aaggaattta ccagacctct aatttcaggg ttgttccctc aggagatgtt gtgagattcc    22440
ctaatattac aaacttgtgt cctttggag aggttttaa tgctactaaa ttcccttctg      22500
tctatgcatg ggagagaaaa aaaatttcta attgtgttgc tgattactct gtgctctaca    22560
actcaacatt ttttcaacc tttaagtgct atggcgtttc tgccactaag ttgaatgatc     22620
tttgcttctc caatgtctat gcagattctt ttgtagtcaa gggagatgat gtaagacaaa    22680
tagcgccagg acaaactggt gttattgctg attataatta taaattgcca gatgatttca    22740
tgggttgtgt ccttgcttgg aatactagga acattgatgc tacttcaact ggtaattata    22800
attataaata taggtatctt agacatggca agcttaggcc ctttgagaga gacatatcta    22860
atgtgccttt ctcccctgat ggcaaacctt gcaccccacc tgctcttaat tgttattggc    22920
cattaaatga ttatggtttt tacaccacta ctggcattgg ctaccaacct tacagagttg    22980
tagtactttc ttttgaactt ttaaatgcac cggccacggt tgtggacca aaattatcca     23040
ctgaccttat taagaaccag tgtgtcaatt ttaattttaa tggactcact ggtactggtg    23100
tgttaactcc ttcttcaaag agatttcaac catttcaaca atttggccgt gatgtttctg    23160
atttcactga ttccgttcga gatcctaaaa catctgaaat attagacatt tcaccttgct    23220
cttttgggg tgtaagtgta attacacctg gaacaaatgc ttcatctgaa gttgctgttc     23280
tatatcaaga tgttaactgc actgatgttt ctacagcaat tcatgcagat caactcacac    23340
cagcttggcg catatattct actggaaaca atgtattcca gactcaagca ggctgtctta    23400
taggagctga gcatgtcgac acttcttatg agtgcgacat tcctattgga gctggcattt    23460
gtgctagtta ccatacagtt tctttattac gtagtactag ccaaaaatct attgtggctt    23520
atactatgtc tttaggtgct gatagttcaa ttgcttactc taataacacc attgctatac    23580
ctactaactt ttcaattagc attactacag aagtaatgcc tgtttctatg gctaaaacct    23640
ccgtagattg taatatgtac atctgcggag attctactga atgtgctaat ttgcttctcc    23700
aatatggtag cttttgcaca caactaaatc gtgcactctc aggtattgct gctgaacagg    23760
atcgcaacac acgtgaagtg ttcgctcaag tcaaacaaat gtacaaaacc ccaactttga    23820
aatattttgg tggttttaat ttttcacaaa tattacctga ccctctaaag ccaactaaga    23880
ggtcttttat tgaggacttg ctctttaata aggtgacact cgctgatgct ggcttcatga    23940
agcaatatgg cgaatgccta ggtgatatta tgctagaga tctcatttgt gcgcagaagt     24000
tcaatggact tacagtgttg ccacctctgc tcactgatga tatgattgct gcctacactg    24060
ctgctctagt tagtggtact gccactgctg atggacatt tggtgctggc gctgctcttc      24120
aaataccttt tgctatgcaa atggcatata ggttcaatgg cattggagtt acccaaaatg    24180
ttctctatga gaaccaaaaa caaatcgcca accaatttaa caaggcgatt agtcaaattc    24240
aagaatcact tacaacaaca tcaactgcat tgggcaagct gcaagacgtt gttaaccaga    24300
atgctcaagc attaaacaca cttgttaaac aacttagctc taattttggt gcaatttcaa    24360
gtgtgctaaa tgatatcctt tcgcgacttg ataaagtcga ggcggaggta caaattgaca    24420
```

```
ggttaattac aggcagactt caaagccttc aaacctatgt aacacaacaa ctaatcaggg    24480
ctgctgaaat cagggcttct gctaatcttg ctgctactaa aatgtctgag tgtgttcttg    24540
gacaatcaaa aagagttgac ttttgtggaa agggctacca ccttatgtcc ttcccacaag    24600
cagccccgca tggtgttgtc ttcctacatg tcacgtatgt gccatcccag gagaggaact    24660
tcaccacagc gccagcaatt tgtcatgaag gcaaagcata cttccctcgt gaaggtgttt    24720
ttgtgtttaa tggcacttct tggttatta cacagaggaa cttcttttct ccacaaataa     24780
ttactacaga caatacattt gtctcaggaa attgtgatgt cgttattggc atcattaaca    24840
acacagttta tgatcctctg caacctgagc tcgactcatt caaagaagag ctggacaagt    24900
acttcaaaaa tcatacatca ccagatgttg atcttggcga catttcaggc attaacgctt    24960
ctgtcgtcaa cattcaaaaa gaaattgacc gcctcaatga ggtcgctaaa aatttaaatg    25020
aatcactcat tgaccttcaa gaattgggaa aatatgagca atatattaaa tggccttggt    25080
atgtttggct cggcttcatt gctggactaa ttgccatcgt catggttaca atcttgcttt    25140
gttgcatgac tagttgttgc agttgcctca agggtgcatg ctcttgtggt tcttgctgca    25200
agtttgatga ggatgactct gagccagttc tcaagggtgt caaattacat tacacataaa    25260
cgaacttatg gatttgtttta tgagattttt tactcttgga tcaattactg cacagccagt    25320
aaaaattgac aatgcttctc ctgcaagtac tgttcatgct acagcaacga taccgctaca    25380
agcctcactc cctttcggat ggcttgttat tggcgttgca tttcttgctg tttttcagag    25440
cgctaccaaa ataattgcgc tcaataaaag atggcagcta gccctttata agggcttcca    25500
gttcatttgc aatttactgc tgctatttgt taccatctat tcacatcttt gcttgtcgc     25560
tgcaggtatg gaggcgcaat ttttgtacct ctatgccttg atatatttc tacaatgcat      25620
caacgcatgt agaattatta tgagatgttg ctttgttgg aagtgcaaat ccaagaaccc      25680
attactttat gatgccaact actttgtttg ctggcacaca cataactatg actactgtat    25740
accatataac agtgtcacag atacaattgt cgttactgaa ggtgacggca tttcaacacc    25800
aaaactcaaa gaagactacc aaattggtgg ttattctgag gataggcact caggtgttaa    25860
agactatgtc gttgtacatg gctatttcac cgaagtttac taccagcttg agtctacaca    25920
aattactaca gacactggta ttgaaaatgc tacattcttc atctttaaca gcttgttaa     25980
agacccaccg aatgtgcaaa tacacacaat cgacggctct tcaggagttg ctaatccagc    26040
aatggatcca atttatgatg agccgacgac gactactagc gtgcctttgt aagcacaaga    26100
aagtgagtac gaacttatgt actcattcgt ttcggaagaa acaggtacgt taatagttaa    26160
tagcgtactt cttttttcttg ctttcgtggt attcttgcta gtcacactag ccatccttac   26220
tgcgcttcga ttgtgtgcgt actgctgcaa tattgttaac gtgagtttag taaaaccaac    26280
ggtttacgtc tactcgcgtg ttaaaaatct gaactcttct gaaggagttc ctgatcttct    26340
ggtctaaacg aactaactat tattattatt ctgtttggaa ctttaacatt gcttatcatg    26400
gcagacaacg gtactattac cgttgaggag cttaaacaac tcctggaaca atggaaccta    26460
gtaataggtt tcctattcct agcctggatt atgttactac aatttgccta ttctaatcgg    26520
aacaggtttt tgtacataat aaagcttgtt ttcctctggc tcttgtgcc agtaacactt      26580
gcttgttttg tgcttgctgc tgtctacaga attaattggg tgactggcgg gattgcgatt    26640
gcaatggctt gtattgtagg cttgatgtgg cttagctact tcgttgcttc cttcaggctg    26700
tttgctcgta cccgctcaat gtggtcattc aacccagaaa caaacattct tctcaatgtg    26760
```

```
cctctccggg ggacaattgt gaccagaccg ctcatggaaa gtgaacttgt cattggtgct     26820
gtgatcattc gtggtcactt gcgaatggcc ggacaccccc tagggcgctg tgacattaag     26880
gacctgccaa aagagatcac tgtggctaca tcacgaacgc tttcttatta caaattagga    26940
gcgtcgcagc gtgtaggcac tgattcaggt tttgctgcat acaaccgcta ccgtattgga    27000
aactataaat taaatacaga ccacgccggt agcaacgaca atattgcttt gctagtacag    27060
taagtgacaa cagatgtttc atcttgttga cttccaggtt acaatagcag agatattgat    27120
tatcattatg aggactttca ggattgctat ttggaatctt gacgttataa taagttcaat    27180
agtgagacaa ttatttaagc ctctaactaa gaagaattat tcggagttag atgatgaaga    27240
acctatggag ttagattatc cataaaacga acatgaaaat tattctcttc ctgacattga    27300
ttgtatttac atcttgcgag ctatatcact atcaggagtg tgttagaggt acgactgtac    27360
tactaaaaga accttgccca tcaggaacat acgagggcaa ttcaccattt caccctcttg    27420
ctgacaataa atttgcacta acttgcacta gcacacactt tgcttttgct tgtgctgacg    27480
gtactcgaca tacctatcag ctgcgtgcaa gatcagtttc accaaaactt ttcatcagac    27540
aagaggaggt tcaacaagag ctctactcgc cactttttct cattgttgct gctctagtat    27600
ttttaatact ttgcttcacc attaagagaa agacagaatg aatgagctca ctttaattga    27660
cttctatttg tgcttttttag cctttctgct attccttgtt ttaataatgc ttattatatt    27720
ttggttttca ctcgaaatcc aggatctaga agaaccttgt accaaagtct aaacgaacat    27780
gaaacttctc attgttttga cttgtatttc tctatgcagt tgcatatgca ctgtagtaca    27840
gcgctgtgca tctaataaac ctcatgtgct tgaagatcct tgtaaggtac aacactaggg    27900
gtaatactta tagcactgct tggctttgtg ctctaggaaa ggttttacct tttcatagat    27960
ggcacactat ggttcaaaca tgcacaccta atgttactat caactgtcaa gatccagctg    28020
gtggtgcgct tatagctagg tgttggtacc ttcatgaagg tcaccaaact gctgcattta    28080
gagacgtact tgttgtttta aataaacgaa caaattaaaa tgtctgataa tggaccccaa    28140
tcaaaccaac gtagtgcccc ccgcattaca tttggtggac ccacagattc aactgacaat    28200
aaccagaatg gaggacgcaa tggggcaagg ccaaaacagc gccgaccccca aggtttaccc    28260
aataatactg cgtcttggtt cacagctctc actcagcatg gcaaggagga acttagattc    28320
cctcgaggcc agggcgttcc aatcaacacc aatagtggtc cagatgacca aattggctac    28380
taccgaagag ctacccgacg agttcgtggt ggtgacggca aaatgaaaga gctcagcccc    28440
agatggtact tctattacct aggaactggc ccagaagctt cacttcccta cggcgctaac    28500
aaagaaggca tcgtatgggt tgcaactgag ggagccttga atacacccaa agaccacatt    28560
ggcacccgca atcctaataa caatgctgcc accgtgctac aacttcctca aggaacaaca    28620
ttgccaaaag gcttctacgc agagggaagc agaggcggca gtcaagcctc ttctcgctcc    28680
tcatcacgta gtcgcggtaa ttcaagaaat tcaactcctg gcagcagtag gggaaattct    28740
cctgctcgaa tggctagcgg aggtggtgaa actgccctcg cgctattgct gctagacaga    28800
ttgaaccagc ttgagagcaa agtttctggt aaaggccaac aacaacaagg ccaaactgtc    28860
actaagaaat ctgctgctga ggcatctaaa aagcctcgcc aaaaacgtac tgccacaaaa    28920
cagtacaacg tcactcaagc atttgggaga cgtggtccag aacaaaccca aggaaatttc    28980
ggggaccaag acctaatcag acaaggaact gattacaaac attggccgca aattgcacaa    29040
tttgctccaa gtgcctctgc attctttgga atgtcacgca ttggcatgga agtcacacct    29100
tcgggaacat ggctgactta tcatggagcc attaaattgg atgacaaaga tccacaattc    29160
```

-continued

```
aaagacaacg tcatactgct gaacaagcac attgacgcat acaaacatt cccaccaaca     29220 gagcctaaaa aggacaaaaa gaaaaagact gatgaagctc agccttgcc gcagagacaa     29280 aagaagcagc ccactgtgac tcttcttcct gcggctgaca tggatgattt ctccagacaa    29340
cttcaaaatt ccatgagtgg agcttctgct gattcaactc aggcataaac actcatgatg    29400
accacacaag gcagatgggc tatgtaaacg ttttcgcaat tccgtttacg atacatagtc    29460
tactcttgtg cagaatgaat tctcgtaact aaacagcaca gtaggttta gttaacttta     29520 atctcacata gcaatcttta atcaatgtgt aacattaggg aggacttgaa agagccacca    29580
cattttcatc gaggccacgc ggagtacgat cgagggtaca gtgaataatg ctagggagag    29640
ctgcctatat ggaagagccc taatgtgtaa aattaatttt agtagtgcta tccccatgtg    29700 atttaatag cttcttagga gaatgac                                         29727
```

<210> SEQ ID NO 2
<211> LENGTH: 4382
<212> TYPE: PRT
<213> ORGANISM: Coronavirus

<400> SEQUENCE: 2

```
Met Glu Ser Leu Val Leu Gly Val Asn Glu Lys Thr His Val Gln Leu
1               5                   10                  15

Ser Leu Pro Val Leu Gln Val Arg Asp Val Leu Val Arg Gly Phe Gly
                20                  25                  30

Asp Ser Val Glu Glu Ala Leu Ser Glu Ala Arg Glu His Leu Lys Asn
            35                  40                  45

Gly Thr Cys Gly Leu Val Glu Leu Glu Lys Gly Val Leu Pro Gln Leu
        50                  55                  60

Glu Gln Pro Tyr Val Phe Ile Lys Arg Ser Asp Ala Leu Ser Thr Asn
65                  70                  75                  80

His Gly His Lys Val Val Glu Leu Val Ala Glu Met Asp Gly Ile Gln
                85                  90                  95

Tyr Gly Arg Ser Gly Ile Thr Leu Gly Val Leu Val Pro His Val Gly
                100                 105                 110

Glu Thr Pro Ile Ala Tyr Arg Asn Val Leu Leu Arg Lys Asn Gly Asn
            115                 120                 125

Lys Gly Ala Gly Gly His Ser Tyr Gly Ile Asp Leu Lys Ser Tyr Asp
        130                 135                 140

Leu Gly Asp Glu Leu Gly Thr Asp Pro Ile Glu Asp Tyr Glu Gln Asn
145                 150                 155                 160

Trp Asn Thr Lys His Gly Ser Gly Ala Leu Arg Glu Leu Thr Arg Glu
                165                 170                 175

Leu Asn Gly Gly Ala Val Thr Arg Tyr Val Asp Asn Asn Phe Cys Gly
            180                 185                 190

Pro Asp Gly Tyr Pro Leu Asp Cys Ile Lys Asp Phe Leu Ala Arg Ala
        195                 200                 205

Gly Lys Ser Met Cys Thr Leu Ser Glu Gln Leu Asp Tyr Ile Glu Ser
    210                 215                 220

Lys Arg Gly Val Tyr Cys Cys Arg Asp His Glu His Glu Ile Ala Trp
225                 230                 235                 240

Phe Thr Glu Arg Ser Asp Lys Ser Tyr Glu His Gln Thr Pro Phe Glu
                245                 250                 255

Ile Lys Ser Ala Lys Lys Phe Asp Thr Phe Lys Gly Glu Cys Pro Lys
            260                 265                 270
```

-continued

```
Phe Val Phe Pro Leu Asn Ser Lys Val Lys Val Ile Gln Pro Arg Val
            275                 280                 285
Glu Lys Lys Lys Thr Glu Gly Phe Met Gly Arg Ile Arg Ser Val Tyr
            290                 295                 300
Pro Val Ala Ser Pro Gln Glu Cys Asn Asn Met His Leu Ser Thr Leu
305                 310                 315                 320
Met Lys Cys Asn His Cys Asp Glu Val Ser Trp Gln Thr Cys Asp Phe
            325                 330                 335
Leu Lys Ala Thr Cys Glu His Cys Gly Thr Glu Asn Leu Val Ile Glu
            340                 345                 350
Gly Pro Thr Thr Cys Gly Tyr Leu Pro Thr Asn Ala Val Lys Met
            355                 360                 365
Pro Cys Pro Ala Cys Gln Asp Pro Glu Ile Gly Pro Glu His Ser Val
            370                 375                 380
Ala Asp Tyr His Asn His Ser Asn Ile Glu Thr Arg Leu Arg Lys Gly
385                 390                 395                 400
Gly Arg Thr Arg Cys Phe Gly Gly Cys Val Phe Ala Tyr Val Gly Cys
            405                 410                 415
Tyr Asn Lys Arg Ala Tyr Trp Val Pro Arg Ala Ser Ala Asp Ile Gly
            420                 425                 430
Ser Gly His Thr Gly Ile Thr Gly Asp Asn Val Glu Thr Leu Asn Glu
            435                 440                 445
Asp Leu Leu Glu Ile Leu Ser Arg Glu Arg Val Asn Ile Asn Ile Val
450                 455                 460
Gly Asp Phe His Leu Asn Glu Glu Val Ala Ile Ile Leu Ala Ser Phe
465                 470                 475                 480
Ser Ala Ser Thr Ser Ala Phe Ile Asp Thr Ile Lys Ser Leu Asp Tyr
            485                 490                 495
Lys Ser Phe Lys Thr Ile Val Glu Ser Cys Gly Asn Tyr Lys Val Thr
            500                 505                 510
Lys Gly Lys Pro Val Lys Gly Ala Trp Asn Ile Gly Gln Gln Arg Ser
            515                 520                 525
Val Leu Thr Pro Leu Cys Gly Phe Pro Ser Gln Ala Ala Gly Val Ile
            530                 535                 540
Arg Ser Ile Phe Ala Arg Thr Leu Asp Ala Ala Asn His Ser Ile Pro
545                 550                 555                 560
Asp Leu Gln Arg Ala Ala Val Thr Ile Leu Asp Gly Ile Ser Glu Gln
            565                 570                 575
Ser Leu Arg Leu Val Asp Ala Met Val Tyr Thr Ser Asp Leu Leu Thr
            580                 585                 590
Asn Ser Val Ile Ile Met Ala Tyr Val Thr Gly Gly Leu Val Gln Gln
            595                 600                 605
Thr Ser Gln Trp Leu Ser Asn Leu Leu Gly Thr Thr Val Glu Lys Leu
            610                 615                 620
Arg Pro Ile Phe Glu Trp Ile Glu Ala Lys Leu Ser Ala Gly Val Glu
625                 630                 635                 640
Phe Leu Lys Asp Ala Trp Glu Ile Leu Lys Phe Leu Ile Thr Gly Val
            645                 650                 655
Phe Asp Ile Val Lys Gly Gln Ile Gln Val Ala Ser Asp Asn Ile Lys
            660                 665                 670
Asp Cys Val Lys Cys Phe Ile Asp Val Val Asn Lys Ala Leu Glu Met
            675                 680                 685
```

-continued

Cys Ile Asp Gln Val Thr Ile Ala Gly Ala Lys Leu Arg Ser Leu Asn
690                 695                 700

Leu Gly Glu Val Phe Ile Ala Gln Ser Lys Gly Leu Tyr Arg Gln Cys
705                 710                 715                 720

Ile Arg Gly Lys Glu Gln Leu Gln Leu Leu Met Pro Leu Lys Ala Pro
            725                 730                 735

Lys Glu Val Thr Phe Leu Glu Gly Asp Ser His Asp Thr Val Leu Thr
            740                 745                 750

Ser Glu Glu Val Val Leu Lys Asn Gly Glu Leu Glu Ala Leu Glu Thr
            755                 760                 765

Pro Val Asp Ser Phe Thr Asn Gly Ala Ile Val Gly Thr Pro Val Cys
770                 775                 780

Val Asn Gly Leu Met Leu Leu Glu Ile Lys Asp Lys Glu Gln Tyr Cys
785                 790                 795                 800

Ala Leu Ser Pro Gly Leu Leu Ala Thr Asn Asn Val Phe Arg Leu Lys
                805                 810                 815

Gly Gly Ala Pro Ile Lys Gly Val Thr Phe Gly Glu Asp Thr Val Trp
                820                 825                 830

Glu Val Gln Gly Tyr Lys Asn Val Arg Ile Thr Phe Glu Leu Asp Glu
            835                 840                 845

Arg Val Asp Lys Val Leu Asn Glu Lys Cys Ser Val Tyr Thr Val Glu
850                 855                 860

Ser Gly Thr Glu Val Thr Glu Phe Ala Cys Val Val Ala Glu Ala Val
865                 870                 875                 880

Val Lys Thr Leu Gln Pro Val Ser Asp Leu Leu Thr Asn Met Gly Ile
                885                 890                 895

Asp Leu Asp Glu Trp Ser Val Ala Thr Phe Tyr Leu Phe Asp Asp Ala
                900                 905                 910

Gly Glu Glu Asn Phe Ser Ser Arg Met Tyr Cys Ser Phe Tyr Pro Pro
            915                 920                 925

Asp Glu Glu Glu Glu Asp Asp Ala Glu Cys Glu Glu Glu Glu Ile Asp
930                 935                 940

Glu Thr Cys Glu His Glu Tyr Gly Thr Glu Asp Asp Tyr Gln Gly Leu
945                 950                 955                 960

Pro Leu Glu Phe Gly Ala Ser Ala Glu Thr Val Arg Val Glu Glu Glu
                965                 970                 975

Glu Glu Glu Asp Trp Leu Asp Asp Thr Thr Glu Gln Ser Glu Ile Glu
                980                 985                 990

Pro Glu Pro Glu Pro Thr Pro Glu Glu Pro Val Asn Gln Phe Thr Gly
            995                 1000                1005

Tyr Leu Lys Leu Thr Asp Asn Val Ala Ile Lys Cys Val Asp Ile
    1010                1015                1020

Val Lys Glu Ala Gln Ser Ala Asn Pro Met Val Ile Val Asn Ala
    1025                1030                1035

Ala Asn Ile His Leu Lys His Gly Gly Gly Val Ala Gly Ala Leu
    1040                1045                1050

Asn Lys Ala Thr Asn Gly Ala Met Gln Lys Glu Ser Asp Asp Tyr
    1055                1060                1065

Ile Lys Leu Asn Gly Pro Leu Thr Val Gly Gly Ser Cys Leu Leu
    1070                1075                1080

Ser Gly His Asn Leu Ala Lys Lys Cys Leu His Val Val Gly Pro
    1085                1090                1095

Asn Leu Asn Ala Gly Glu Asp Ile Gln Leu Leu Lys Ala Ala Tyr

-continued

```
              1100                1105                1110
Glu Asn Phe Asn Ser Gln Asp Ile Leu Leu Ala Pro Leu Leu Ser
    1115                1120                1125

Ala Gly Ile Phe Gly Ala Lys Pro Leu Gln Ser Leu Gln Val Cys
    1130                1135                1140

Val Gln Thr Val Arg Thr Gln Val Tyr Ile Ala Val Asn Asp Lys
    1145                1150                1155

Ala Leu Tyr Glu Gln Val Val Met Asp Tyr Leu Asp Asn Leu Lys
    1160                1165                1170

Pro Arg Val Glu Ala Pro Lys Gln Glu Pro Pro Asn Thr Glu
    1175                1180                1185

Asp Ser Lys Thr Glu Glu Lys Ser Val Val Gln Lys Pro Val Asp
    1190                1195                1200

Val Lys Pro Lys Ile Lys Ala Cys Ile Asp Glu Val Thr Thr Thr
    1205                1210                1215

Leu Glu Glu Thr Lys Phe Leu Thr Asn Lys Leu Leu Leu Phe Ala
    1220                1225                1230

Asp Ile Asn Gly Lys Leu Tyr His Asp Ser Gln Asn Met Leu Arg
    1235                1240                1245

Gly Glu Asp Met Ser Phe Leu Glu Lys Asp Ala Pro Tyr Met Val
    1250                1255                1260

Gly Asp Val Ile Thr Ser Gly Asp Ile Thr Cys Val Val Ile Pro
    1265                1270                1275

Ser Lys Lys Ala Gly Gly Thr Thr Glu Met Leu Ser Arg Ala Leu
    1280                1285                1290

Lys Lys Val Pro Val Asp Glu Tyr Ile Thr Thr Tyr Pro Gly Gln
    1295                1300                1305

Gly Cys Ala Gly Tyr Thr Leu Glu Glu Ala Lys Thr Ala Leu Lys
    1310                1315                1320

Lys Cys Lys Ser Ala Phe Tyr Val Leu Pro Ser Glu Ala Pro Asn
    1325                1330                1335

Ala Lys Glu Glu Ile Leu Gly Thr Val Ser Trp Asn Leu Arg Glu
    1340                1345                1350

Met Leu Ala His Ala Glu Glu Thr Arg Lys Leu Met Pro Ile Cys
    1355                1360                1365

Met Asp Val Arg Ala Ile Met Ala Thr Ile Gln Arg Lys Tyr Lys
    1370                1375                1380

Gly Ile Lys Ile Gln Glu Gly Ile Val Asp Tyr Gly Val Arg Phe
    1385                1390                1395

Phe Phe Tyr Thr Ser Lys Glu Pro Val Ala Ser Ile Ile Thr Lys
    1400                1405                1410

Leu Asn Ser Leu Asn Glu Pro Leu Val Thr Met Pro Ile Gly Tyr
    1415                1420                1425

Val Thr His Gly Phe Asn Leu Glu Glu Ala Ala Arg Cys Met Arg
    1430                1435                1440

Ser Leu Lys Ala Pro Ala Val Val Ser Val Ser Pro Asp Ala
    1445                1450                1455

Val Thr Thr Tyr Asn Gly Tyr Leu Thr Ser Ser Ser Lys Thr Ser
    1460                1465                1470

Glu Glu His Phe Val Glu Thr Val Ser Leu Ala Gly Ser Tyr Arg
    1475                1480                1485

Asp Trp Ser Tyr Ser Gly Gln Arg Thr Glu Leu Gly Val Glu Phe
    1490                1495                1500
```

```
Leu Lys Arg Gly Asp Lys Ile Val Tyr His Thr Leu Glu Ser Pro
    1505                1510                1515

Val Glu Phe His Leu Asp Gly Glu Val Leu Ser Leu Asp Lys Leu
    1520                1525                1530

Lys Ser Leu Leu Ser Leu Arg Glu Val Lys Thr Ile Lys Val Phe
    1535                1540                1545

Thr Thr Val Asp Asn Thr Asn Leu His Thr Gln Leu Val Asp Met
    1550                1555                1560

Ser Met Thr Tyr Gly Gln Gln Phe Gly Pro Thr Tyr Leu Asp Gly
    1565                1570                1575

Ala Asp Val Thr Lys Ile Lys Pro His Val Asn His Glu Gly Lys
    1580                1585                1590

Thr Phe Phe Val Leu Pro Ser Asp Asp Thr Leu Arg Ser Glu Ala
    1595                1600                1605

Phe Glu Tyr Tyr His Thr Leu Asp Glu Ser Phe Leu Gly Arg Tyr
    1610                1615                1620

Met Ser Ala Leu Asn His Thr Lys Lys Trp Lys Phe Pro Gln Val
    1625                1630                1635

Gly Gly Leu Thr Ser Ile Lys Trp Ala Asp Asn Asn Cys Tyr Leu
    1640                1645                1650

Ser Ser Val Leu Leu Ala Leu Gln Gln Leu Glu Val Lys Phe Asn
    1655                1660                1665

Ala Pro Ala Leu Gln Glu Ala Tyr Tyr Arg Ala Arg Ala Gly Asp
    1670                1675                1680

Ala Ala Asn Phe Cys Ala Leu Ile Leu Ala Tyr Ser Asn Lys Thr
    1685                1690                1695

Val Gly Glu Leu Gly Asp Val Arg Glu Thr Met Thr His Leu Leu
    1700                1705                1710

Gln His Ala Asn Leu Glu Ser Ala Lys Arg Val Leu Asn Val Val
    1715                1720                1725

Cys Lys His Cys Gly Gln Lys Thr Thr Thr Leu Thr Gly Val Glu
    1730                1735                1740

Ala Val Met Tyr Met Gly Thr Leu Ser Tyr Asp Asn Leu Lys Thr
    1745                1750                1755

Gly Val Ser Ile Pro Cys Val Cys Gly Arg Asp Ala Thr Gln Tyr
    1760                1765                1770

Leu Val Gln Gln Glu Ser Ser Phe Val Met Met Ser Ala Pro Pro
    1775                1780                1785

Ala Glu Tyr Lys Leu Gln Gln Gly Thr Phe Leu Cys Ala Asn Glu
    1790                1795                1800

Tyr Thr Gly Asn Tyr Gln Cys Gly His Tyr Thr His Ile Thr Ala
    1805                1810                1815

Lys Glu Thr Leu Tyr Arg Ile Asp Gly Ala His Leu Thr Lys Met
    1820                1825                1830

Ser Glu Tyr Lys Gly Pro Val Thr Asp Val Phe Tyr Lys Glu Thr
    1835                1840                1845

Ser Tyr Thr Thr Thr Ile Lys Pro Val Ser Tyr Lys Leu Asp Gly
    1850                1855                1860

Val Thr Tyr Thr Glu Ile Glu Pro Lys Leu Asp Gly Tyr Tyr Lys
    1865                1870                1875

Lys Asp Asn Ala Tyr Tyr Thr Glu Gln Pro Ile Asp Leu Val Pro
    1880                1885                1890
```

-continued

```
Thr Gln Pro Leu Pro Asn Ala Ser Phe Asp Asn Phe Lys Leu Thr
    1895                1900                1905

Cys Ser Asn Thr Lys Phe Ala Asp Asp Leu Asn Gln Met Thr Gly
    1910                1915                1920

Phe Thr Lys Pro Ala Ser Arg Glu Leu Ser Val Thr Phe Phe Pro
    1925                1930                1935

Asp Leu Asn Gly Asp Val Val Ala Ile Asp Tyr Arg His Tyr Ser
    1940                1945                1950

Ala Ser Phe Lys Lys Gly Ala Lys Leu Leu His Lys Pro Ile Val
    1955                1960                1965

Trp His Ile Asn Gln Ala Thr Thr Lys Thr Thr Phe Lys Pro Asn
    1970                1975                1980

Thr Trp Cys Leu Arg Cys Leu Trp Ser Thr Lys Pro Val Asp Thr
    1985                1990                1995

Ser Asn Ser Phe Glu Val Leu Ala Val Glu Asp Thr Gln Gly Met
    2000                2005                2010

Asp Asn Leu Ala Cys Glu Ser Gln Gln Pro Thr Ser Glu Glu Val
    2015                2020                2025

Val Glu Asn Pro Thr Ile Gln Lys Glu Val Ile Glu Cys Asp Val
    2030                2035                2040

Lys Thr Thr Glu Val Val Gly Asn Val Ile Leu Lys Pro Ser Asp
    2045                2050                2055

Glu Gly Val Lys Val Thr Gln Glu Leu Gly His Glu Asp Leu Met
    2060                2065                2070

Ala Ala Tyr Val Glu Asn Thr Ser Ile Thr Ile Lys Lys Pro Asn
    2075                2080                2085

Glu Leu Ser Leu Ala Leu Gly Leu Lys Thr Ile Ala Thr His Gly
    2090                2095                2100

Ile Ala Ala Ile Asn Ser Val Pro Trp Ser Lys Ile Leu Ala Tyr
    2105                2110                2115

Val Lys Pro Phe Leu Gly Gln Ala Ala Ile Thr Thr Ser Asn Cys
    2120                2125                2130

Ala Lys Arg Leu Ala Gln Arg Val Phe Asn Asn Tyr Met Pro Tyr
    2135                2140                2145

Val Phe Thr Leu Leu Phe Gln Leu Cys Thr Phe Thr Lys Ser Thr
    2150                2155                2160

Asn Ser Arg Ile Arg Ala Ser Leu Pro Thr Thr Ile Ala Lys Asn
    2165                2170                2175

Ser Val Lys Ser Val Ala Lys Leu Cys Leu Asp Ala Gly Ile Asn
    2180                2185                2190

Tyr Val Lys Ser Pro Lys Phe Ser Lys Leu Phe Thr Ile Ala Met
    2195                2200                2205

Trp Leu Leu Leu Ser Ile Cys Leu Gly Ser Leu Ile Cys Val
    2210                2215                2220

Thr Ala Ala Phe Gly Val Leu Leu Ser Asn Phe Gly Ala Pro Ser
    2225                2230                2235

Tyr Cys Asn Gly Val Arg Glu Leu Tyr Leu Asn Ser Ser Asn Val
    2240                2245                2250

Thr Thr Met Asp Phe Cys Glu Gly Ser Phe Pro Cys Ser Ile Cys
    2255                2260                2265

Leu Ser Gly Leu Asp Ser Leu Asp Ser Tyr Pro Ala Leu Glu Thr
    2270                2275                2280

Ile Gln Val Thr Ile Ser Ser Tyr Lys Leu Asp Leu Thr Ile Leu
```

-continued

```
              2285                2290                2295
Gly Leu Ala Ala Glu Trp Val Leu Ala Tyr Met Leu Phe Thr Lys
        2300                2305                2310

Phe Phe Tyr Leu Leu Gly Leu Ser Ala Ile Met Gln Val Phe Phe
        2315                2320                2325

Gly Tyr Phe Ala Ser His Phe Ile Ser Asn Ser Trp Leu Met Trp
        2330                2335                2340

Phe Ile Ile Ser Ile Val Gln Met Ala Pro Val Ser Ala Met Val
        2345                2350                2355

Arg Met Tyr Ile Phe Phe Ala Ser Phe Tyr Tyr Ile Trp Lys Ser
        2360                2365                2370

Tyr Val His Ile Met Asp Gly Cys Thr Ser Thr Cys Met Met
        2375                2380                2385

Cys Tyr Lys Arg Asn Arg Ala Thr Arg Val Glu Cys Thr Thr Ile
        2390                2395                2400

Val Asn Gly Met Lys Arg Ser Phe Tyr Val Tyr Ala Asn Gly Gly
        2405                2410                2415

Arg Gly Phe Cys Lys Thr His Asn Trp Asn Cys Leu Asn Cys Asp
        2420                2425                2430

Thr Phe Cys Thr Gly Ser Thr Phe Ile Ser Asp Glu Val Ala Arg
        2435                2440                2445

Asp Leu Ser Leu Gln Phe Lys Arg Pro Ile Asn Pro Thr Asp Gln
        2450                2455                2460

Ser Ser Tyr Ile Val Asp Ser Val Ala Val Lys Asn Gly Ala Leu
        2465                2470                2475

His Leu Tyr Phe Asp Lys Ala Gly Gln Lys Thr Tyr Glu Arg His
        2480                2485                2490

Pro Leu Ser His Phe Val Asn Leu Asp Asn Leu Arg Ala Asn Asn
        2495                2500                2505

Thr Lys Gly Ser Leu Pro Ile Asn Val Ile Val Phe Asp Gly Lys
        2510                2515                2520

Ser Lys Cys Asp Glu Ser Ala Ser Lys Ser Ala Ser Val Tyr Tyr
        2525                2530                2535

Ser Gln Leu Met Cys Gln Pro Ile Leu Leu Leu Asp Gln Val Leu
        2540                2545                2550

Val Ser Asp Val Gly Asp Ser Thr Glu Val Ser Val Lys Met Phe
        2555                2560                2565

Asp Ala Tyr Val Asp Thr Phe Ser Ala Thr Phe Ser Val Pro Met
        2570                2575                2580

Glu Lys Leu Lys Ala Leu Val Ala Thr Ala His Ser Glu Leu Ala
        2585                2590                2595

Lys Gly Val Ala Leu Asp Gly Val Leu Ser Thr Phe Val Ser Ala
        2600                2605                2610

Ala Arg Gln Gly Val Val Asp Thr Asp Val Asp Thr Lys Asp Val
        2615                2620                2625

Ile Glu Cys Leu Lys Leu Ser His His Ser Asp Leu Glu Val Thr
        2630                2635                2640

Gly Asp Ser Cys Asn Asn Phe Met Leu Thr Tyr Asn Lys Val Glu
        2645                2650                2655

Asn Met Thr Pro Arg Asp Leu Gly Ala Cys Ile Asp Cys Asn Ala
        2660                2665                2670

Arg His Ile Asn Ala Gln Val Ala Lys Ser His Asn Val Ser Leu
        2675                2680                2685
```

-continued

```
Ile Trp Asn Val Lys Asp Tyr Met Ser Leu Ser Glu Gln Leu Arg
    2690            2695                2700

Lys Gln Ile Arg Ser Ala Ala Lys Lys Asn Asn Ile Pro Phe Arg
    2705            2710                2715

Leu Thr Cys Ala Thr Thr Arg Gln Val Val Asn Val Ile Thr Thr
    2720            2725                2730

Lys Ile Ser Leu Lys Gly Gly Lys Ile Val Ser Thr Cys Phe Lys
    2735            2740                2745

Leu Met Leu Lys Ala Thr Leu Leu Cys Val Leu Ala Ala Leu Val
    2750            2755                2760

Cys Tyr Ile Val Met Pro Val His Thr Leu Ser Ile His Asp Gly
    2765            2770                2775

Tyr Thr Asn Glu Ile Ile Gly Tyr Lys Ala Ile Gln Asp Gly Val
    2780            2785                2790

Thr Arg Asp Ile Ile Ser Thr Asp Asp Cys Phe Ala Asn Lys His
    2795            2800                2805

Ala Gly Phe Asp Ala Trp Phe Ser Gln Arg Gly Gly Ser Tyr Lys
    2810            2815                2820

Asn Asp Lys Ser Cys Pro Val Val Ala Ala Ile Thr Arg Glu
    2825            2830                2835

Ile Gly Phe Ile Val Pro Gly Leu Pro Gly Thr Val Leu Arg Ala
    2840            2845                2850

Ile Asn Gly Asp Phe Leu His Phe Leu Pro Arg Val Phe Ser Ala
    2855            2860                2865

Val Gly Asn Ile Cys Tyr Thr Pro Ser Lys Leu Ile Glu Tyr Ser
    2870            2875                2880

Asp Phe Ala Thr Ser Ala Cys Val Leu Ala Ala Glu Cys Thr Ile
    2885            2890                2895

Phe Lys Asp Ala Met Gly Lys Pro Val Pro Tyr Cys Tyr Asp Thr
    2900            2905                2910

Asn Leu Leu Glu Gly Ser Ile Ser Tyr Ser Glu Leu Arg Pro Asp
    2915            2920                2925

Thr Arg Tyr Val Leu Met Asp Gly Ser Ile Ile Gln Phe Pro Asn
    2930            2935                2940

Thr Tyr Leu Glu Gly Ser Val Arg Val Val Thr Thr Phe Asp Ala
    2945            2950                2955

Glu Tyr Cys Arg His Gly Thr Cys Glu Arg Ser Glu Val Gly Ile
    2960            2965                2970

Cys Leu Ser Thr Ser Gly Arg Trp Val Leu Asn Asn Glu His Tyr
    2975            2980                2985

Arg Ala Leu Ser Gly Val Phe Cys Gly Val Asp Ala Met Asn Leu
    2990            2995                3000

Ile Ala Asn Ile Phe Thr Pro Leu Val Gln Pro Val Gly Ala Leu
    3005            3010                3015

Asp Val Ser Ala Ser Val Val Ala Gly Gly Ile Ile Ala Ile Leu
    3020            3025                3030

Val Thr Cys Ala Ala Tyr Tyr Phe Met Lys Phe Arg Arg Val Phe
    3035            3040                3045

Gly Glu Tyr Asn His Val Val Ala Ala Asn Ala Leu Leu Phe Leu
    3050            3055                3060

Met Ser Phe Thr Ile Leu Cys Leu Val Pro Ala Tyr Ser Phe Leu
    3065            3070                3075
```

-continued

| | | | | | | | | | | | |
|---|---|---|---|---|---|---|---|---|---|---|---|
| Pro | Gly | Val | Tyr | Ser | Val | Phe | Tyr | Leu | Tyr | Leu | Thr | Phe | Tyr | Phe |
| | 3080 | | | | 3085 | | | | 3090 | | |

Pro Gly Val Tyr Ser Val Phe Tyr Leu Tyr Leu Thr Phe Tyr Phe
    3080                      3085                      3090

Thr Asn Asp Val Ser Phe Leu Ala His Leu Gln Trp Phe Ala Met
    3095                      3100                      3105

Phe Ser Pro Ile Val Pro Phe Trp Ile Thr Ala Ile Tyr Val Phe
    3110                      3115                      3120

Cys Ile Ser Leu Lys His Cys His Trp Phe Phe Asn Asn Tyr Leu
    3125                      3130                      3135

Arg Lys Arg Val Met Phe Asn Gly Val Thr Phe Ser Thr Phe Glu
    3140                      3145                      3150

Glu Ala Ala Leu Cys Thr Phe Leu Leu Asn Lys Glu Met Tyr Leu
    3155                      3160                      3165

Lys Leu Arg Ser Glu Thr Leu Leu Pro Leu Thr Gln Tyr Asn Arg
    3170                      3175                      3180

Tyr Leu Ala Leu Tyr Asn Lys Tyr Lys Tyr Phe Ser Gly Ala Leu
    3185                      3190                      3195

Asp Thr Thr Ser Tyr Arg Glu Ala Ala Cys Cys His Leu Ala Lys
    3200                      3205                      3210

Ala Leu Asn Asp Phe Ser Asn Ser Gly Ala Asp Val Leu Tyr Gln
    3215                      3220                      3225

Pro Pro Gln Thr Ser Ile Thr Ser Ala Val Leu Gln Ser Gly Phe
    3230                      3235                      3240

Arg Lys Met Ala Phe Pro Ser Gly Lys Val Glu Gly Cys Met Val
    3245                      3250                      3255

Gln Val Thr Cys Gly Thr Thr Thr Leu Asn Gly Leu Trp Leu Asp
    3260                      3265                      3270

Asp Thr Val Tyr Cys Pro Arg His Val Ile Cys Thr Ala Glu Asp
    3275                      3280                      3285

Met Leu Asn Pro Asn Tyr Glu Asp Leu Leu Ile Arg Lys Ser Asn
    3290                      3295                      3300

His Ser Phe Leu Val Gln Ala Gly Asn Val Gln Leu Arg Val Ile
    3305                      3310                      3315

Gly His Ser Met Gln Asn Cys Leu Leu Arg Leu Lys Val Asp Thr
    3320                      3325                      3330

Ser Asn Pro Lys Thr Pro Lys Tyr Lys Phe Val Arg Ile Gln Pro
    3335                      3340                      3345

Gly Gln Thr Phe Ser Val Leu Ala Cys Tyr Asn Gly Ser Pro Ser
    3350                      3355                      3360

Gly Val Tyr Gln Cys Ala Met Arg Pro Asn His Thr Ile Lys Gly
    3365                      3370                      3375

Ser Phe Leu Asn Gly Ser Cys Gly Ser Val Gly Phe Asn Ile Asp
    3380                      3385                      3390

Tyr Asp Cys Val Ser Phe Cys Tyr Met His His Met Glu Leu Pro
    3395                      3400                      3405

Thr Gly Val His Ala Gly Thr Asp Leu Glu Gly Lys Phe Tyr Gly
    3410                      3415                      3420

Pro Phe Val Asp Arg Gln Thr Ala Gln Ala Ala Gly Thr Asp Thr
    3425                      3430                      3435

Thr Ile Thr Leu Asn Val Leu Ala Trp Leu Tyr Ala Ala Val Ile
    3440                      3445                      3450

Asn Gly Asp Arg Trp Phe Leu Asn Arg Phe Thr Thr Thr Leu Asn
    3455                      3460                      3465

Asp Phe Asn Leu Val Ala Met Lys Tyr Asn Tyr Glu Pro Leu Thr

-continued

```
              3470                3475                3480
Gln Asp His Val Asp Ile Leu Gly Pro Leu Ser Ala Gln Thr Gly
        3485                3490                3495
Ile Ala Val Leu Asp Met Cys Ala Ala Leu Lys Glu Leu Leu Gln
        3500                3505                3510
Asn Gly Met Asn Gly Arg Thr Ile Leu Gly Ser Thr Ile Leu Glu
        3515                3520                3525
Asp Glu Phe Thr Pro Phe Asp Val Val Arg Gln Cys Ser Gly Val
        3530                3535                3540
Thr Phe Gln Gly Lys Phe Lys Lys Ile Val Lys Gly Thr His His
        3545                3550                3555
Trp Met Leu Leu Thr Phe Leu Thr Ser Leu Leu Ile Leu Val Gln
        3560                3565                3570
Ser Thr Gln Trp Ser Leu Phe Phe Val Tyr Glu Asn Ala Phe
        3575                3580                3585
Leu Pro Phe Thr Leu Gly Ile Met Ala Ile Ala Ala Cys Ala Met
        3590                3595                3600
Leu Leu Val Lys His Lys His Ala Phe Leu Cys Leu Phe Leu Leu
        3605                3610                3615
Pro Ser Leu Ala Thr Val Ala Tyr Phe Asn Met Val Tyr Met Pro
        3620                3625                3630
Ala Ser Trp Val Met Arg Ile Met Thr Trp Leu Glu Leu Ala Asp
        3635                3640                3645
Thr Ser Leu Ser Gly Tyr Arg Leu Lys Asp Cys Val Met Tyr Ala
        3650                3655                3660
Ser Ala Leu Val Leu Leu Ile Leu Met Thr Ala Arg Thr Val Tyr
        3665                3670                3675
Asp Asp Ala Ala Arg Arg Val Trp Thr Leu Met Asn Val Ile Thr
        3680                3685                3690
Leu Val Tyr Lys Val Tyr Tyr Gly Asn Ala Leu Asp Gln Ala Ile
        3695                3700                3705
Ser Met Trp Ala Leu Val Ile Ser Val Thr Ser Asn Tyr Ser Gly
        3710                3715                3720
Val Val Thr Thr Ile Met Phe Leu Ala Arg Ala Ile Val Phe Val
        3725                3730                3735
Cys Val Glu Tyr Tyr Pro Leu Leu Phe Ile Thr Gly Asn Thr Leu
        3740                3745                3750
Gln Cys Ile Met Leu Val Tyr Cys Phe Leu Gly Tyr Cys Cys Cys
        3755                3760                3765
Cys Tyr Phe Gly Leu Phe Cys Leu Leu Asn Arg Tyr Phe Arg Leu
        3770                3775                3780
Thr Leu Gly Val Tyr Asp Tyr Leu Val Ser Thr Gln Glu Phe Arg
        3785                3790                3795
Tyr Met Asn Ser Gln Gly Leu Leu Pro Pro Lys Ser Ser Ile Asp
        3800                3805                3810
Ala Phe Lys Leu Asn Ile Lys Leu Leu Gly Ile Gly Gly Lys Pro
        3815                3820                3825
Cys Ile Lys Val Ala Thr Val Gln Ser Lys Met Ser Asp Val Lys
        3830                3835                3840
Cys Thr Ser Val Val Leu Leu Ser Val Leu Gln Gln Leu Arg Val
        3845                3850                3855
Glu Ser Ser Ser Lys Leu Trp Ala Gln Cys Val Gln Leu His Asn
        3860                3865                3870
```

-continued

```
Asp Ile Leu Leu Ala Lys Asp Thr Thr Glu Ala Phe Glu Lys Met
        3875                3880                3885

Val Ser Leu Leu Ser Val Leu Leu Ser Met Gln Gly Ala Val Asp
        3890                3895                3900

Ile Asn Arg Leu Cys Glu Glu Met Leu Asp Asn Arg Ala Thr Leu
        3905                3910                3915

Gln Ala Ile Ala Ser Glu Phe Ser Ser Leu Pro Ser Tyr Ala Ala
        3920                3925                3930

Tyr Ala Thr Ala Gln Glu Ala Tyr Glu Gln Ala Val Ala Asn Gly
        3935                3940                3945

Asp Ser Glu Val Val Leu Lys Lys Leu Lys Lys Ser Leu Asn Val
        3950                3955                3960

Ala Lys Ser Glu Phe Asp Arg Asp Ala Ala Met Gln Arg Lys Leu
        3965                3970                3975

Glu Lys Met Ala Asp Gln Ala Met Thr Gln Met Tyr Lys Gln Ala
        3980                3985                3990

Arg Ser Glu Asp Lys Arg Ala Lys Val Thr Ser Ala Met Gln Thr
        3995                4000                4005

Met Leu Phe Thr Met Leu Arg Lys Leu Asp Asn Asp Ala Leu Asn
        4010                4015                4020

Asn Ile Ile Asn Asn Ala Arg Asp Gly Cys Val Pro Leu Asn Ile
        4025                4030                4035

Ile Pro Leu Thr Thr Ala Ala Lys Leu Met Val Val Val Pro Asp
        4040                4045                4050

Tyr Gly Thr Tyr Lys Asn Thr Cys Asp Gly Asn Thr Phe Thr Tyr
        4055                4060                4065

Ala Ser Ala Leu Trp Glu Ile Gln Gln Val Val Asp Ala Asp Ser
        4070                4075                4080

Lys Ile Val Gln Leu Ser Glu Ile Asn Met Asp Asn Ser Pro Asn
        4085                4090                4095

Leu Ala Trp Pro Leu Ile Val Thr Ala Leu Arg Ala Asn Ser Ala
        4100                4105                4110

Val Lys Leu Gln Asn Asn Glu Leu Ser Pro Val Ala Leu Arg Gln
        4115                4120                4125

Met Ser Cys Ala Ala Gly Thr Thr Gln Thr Ala Cys Thr Asp Asp
        4130                4135                4140

Asn Ala Leu Ala Tyr Tyr Asn Asn Ser Lys Gly Gly Arg Phe Val
        4145                4150                4155

Leu Ala Leu Leu Ser Asp His Gln Asp Leu Lys Trp Ala Arg Phe
        4160                4165                4170

Pro Lys Ser Asp Gly Thr Gly Thr Ile Tyr Thr Glu Leu Glu Pro
        4175                4180                4185

Pro Cys Arg Phe Val Thr Asp Thr Pro Lys Gly Pro Lys Val Lys
        4190                4195                4200

Tyr Leu Tyr Phe Ile Lys Gly Leu Asn Asn Leu Asn Arg Gly Met
        4205                4210                4215

Val Leu Gly Ser Leu Ala Ala Thr Val Arg Leu Gln Ala Gly Asn
        4220                4225                4230

Ala Thr Glu Val Pro Ala Asn Ser Thr Val Leu Ser Phe Cys Ala
        4235                4240                4245

Phe Ala Val Asp Pro Ala Lys Ala Tyr Lys Asp Tyr Leu Ala Ser
        4250                4255                4260
```

-continued

```
Gly Gly Gln Pro Ile Thr Asn Cys Val Lys Met Leu Cys Thr His
    4265                4270                4275
Thr Gly Thr Gly Gln Ala Ile Thr Val Thr Pro Glu Ala Asn Met
    4280                4285                4290
Asp Gln Glu Ser Phe Gly Ala Ser Cys Cys Leu Tyr Cys Arg
    4295                4300                4305
Cys His Ile Asp His Pro Asn Pro Lys Gly Phe Cys Asp Leu Lys
    4310                4315                4320
Gly Lys Tyr Val Gln Ile Pro Thr Thr Cys Ala Asn Asp Pro Val
    4325                4330                4335
Gly Phe Thr Leu Arg Asn Thr Val Cys Thr Val Cys Gly Met Trp
    4340                4345                4350
Lys Gly Tyr Gly Cys Ser Cys Asp Gln Leu Arg Glu Pro Leu Met
    4355                4360                4365
Gln Ser Ala Asp Ala Ser Thr Phe Leu Asn Gly Phe Ala Val
    4370                4375                4380

<210> SEQ ID NO 3
<211> LENGTH: 2695
<212> TYPE: PRT
<213> ORGANISM: Coronavirus

<400> SEQUENCE: 3

Arg Val Cys Gly Val Ser Ala Ala Arg Leu Thr Pro Cys Gly Thr Gly
1               5                   10                  15
Thr Ser Thr Asp Val Val Tyr Arg Ala Phe Asp Ile Tyr Asn Glu Lys
                20                  25                  30
Val Ala Gly Phe Ala Lys Phe Leu Lys Thr Asn Cys Cys Arg Phe Gln
            35                  40                  45
Glu Lys Asp Glu Glu Gly Asn Leu Leu Asp Ser Tyr Phe Val Val Lys
        50                  55                  60
Arg His Thr Met Ser Asn Tyr Gln His Glu Glu Thr Ile Tyr Asn Leu
65                  70                  75                  80
Val Lys Asp Cys Pro Ala Val Ala Val His Asp Phe Phe Lys Phe Arg
                85                  90                  95
Val Asp Gly Asp Met Val Pro His Ile Ser Arg Gln Arg Leu Thr Lys
            100                 105                 110
Tyr Thr Met Ala Asp Leu Val Tyr Ala Leu Arg His Phe Asp Glu Gly
        115                 120                 125
Asn Cys Asp Thr Leu Lys Glu Ile Leu Val Thr Tyr Asn Cys Cys Asp
    130                 135                 140
Asp Asp Tyr Phe Asn Lys Lys Asp Trp Tyr Asp Phe Val Glu Asn Pro
145                 150                 155                 160
Asp Ile Leu Arg Val Tyr Ala Asn Leu Gly Glu Arg Val Arg Gln Ser
                165                 170                 175
Leu Leu Lys Thr Val Gln Phe Cys Asp Ala Met Arg Asp Ala Gly Ile
            180                 185                 190
Val Gly Val Leu Thr Leu Asp Asn Gln Asp Leu Asn Gly Asn Trp Tyr
        195                 200                 205
Asp Phe Gly Asp Phe Val Gln Val Ala Pro Gly Cys Gly Val Pro Ile
    210                 215                 220
Val Asp Ser Tyr Tyr Ser Leu Leu Met Pro Ile Leu Thr Leu Thr Arg
225                 230                 235                 240
Ala Leu Ala Ala Glu Ser His Met Asp Ala Asp Leu Ala Lys Pro Leu
                245                 250                 255
```

```
Ile Lys Trp Asp Leu Leu Lys Tyr Asp Phe Thr Glu Glu Arg Leu Cys
            260                 265                 270

Leu Phe Asp Arg Tyr Phe Lys Tyr Trp Asp Gln Thr Tyr His Pro Asn
            275                 280                 285

Cys Ile Asn Cys Leu Asp Asp Arg Cys Ile Leu His Cys Ala Asn Phe
            290                 295                 300

Asn Val Leu Phe Ser Thr Val Phe Pro Thr Ser Phe Gly Pro Leu
305                 310                 315                 320

Val Arg Lys Ile Phe Val Asp Gly Val Pro Phe Val Val Ser Thr Gly
                325                 330                 335

Tyr His Phe Arg Glu Leu Gly Val Val His Asn Gln Asp Val Asn Leu
            340                 345                 350

His Ser Ser Arg Leu Ser Phe Lys Glu Leu Leu Val Tyr Ala Ala Asp
            355                 360                 365

Pro Ala Met His Ala Ala Ser Gly Asn Leu Leu Leu Asp Lys Arg Thr
            370                 375                 380

Thr Cys Phe Ser Val Ala Ala Leu Thr Asn Asn Val Ala Phe Gln Thr
385                 390                 395                 400

Val Lys Pro Gly Asn Phe Asn Lys Asp Phe Tyr Asp Phe Ala Val Ser
                405                 410                 415

Lys Gly Phe Phe Lys Glu Gly Ser Ser Val Glu Leu Lys His Phe Phe
            420                 425                 430

Phe Ala Gln Asp Gly Asn Ala Ala Ile Ser Asp Tyr Asp Tyr Tyr Arg
            435                 440                 445

Tyr Asn Leu Pro Thr Met Cys Asp Ile Arg Gln Leu Leu Phe Val Val
            450                 455                 460

Glu Val Val Asp Lys Tyr Phe Asp Cys Tyr Asp Gly Gly Cys Ile Asn
465                 470                 475                 480

Ala Asn Gln Val Ile Val Asn Asn Leu Asp Lys Ser Ala Gly Phe Pro
                485                 490                 495

Phe Asn Lys Trp Gly Lys Ala Arg Leu Tyr Tyr Asp Ser Met Ser Tyr
            500                 505                 510

Glu Asp Gln Asp Ala Leu Phe Ala Tyr Thr Lys Arg Asn Val Ile Pro
            515                 520                 525

Thr Ile Thr Gln Met Asn Leu Lys Tyr Ala Ile Ser Ala Lys Asn Arg
530                 535                 540

Ala Arg Thr Val Ala Gly Val Ser Ile Cys Ser Thr Met Thr Asn Arg
545                 550                 555                 560

Gln Phe His Gln Lys Leu Leu Lys Ser Ile Ala Ala Thr Arg Gly Ala
                565                 570                 575

Thr Val Val Ile Gly Thr Ser Lys Phe Tyr Gly Gly Trp His Asn Met
            580                 585                 590

Leu Lys Thr Val Tyr Ser Asp Val Glu Thr Pro His Leu Met Gly Trp
            595                 600                 605

Asp Tyr Pro Lys Cys Asp Arg Ala Met Pro Asn Met Leu Arg Ile Met
            610                 615                 620

Ala Ser Leu Val Leu Ala Arg Lys His Asn Thr Cys Cys Asn Leu Ser
625                 630                 635                 640

His Arg Phe Tyr Arg Leu Ala Asn Glu Cys Ala Gln Val Leu Ser Glu
                645                 650                 655

Met Val Met Cys Gly Gly Ser Leu Tyr Val Lys Pro Gly Gly Thr Ser
            660                 665                 670
```

-continued

```
Ser Gly Asp Ala Thr Thr Ala Tyr Ala Asn Ser Val Phe Asn Ile Cys
    675                 680                 685

Gln Ala Val Thr Ala Asn Val Asn Ala Leu Leu Ser Thr Asp Gly Asn
690                 695                 700

Lys Ile Ala Asp Lys Tyr Val Arg Asn Leu Gln His Arg Leu Tyr Glu
705                 710                 715                 720

Cys Leu Tyr Arg Asn Arg Asp Val Asp His Glu Phe Val Asp Glu Phe
                725                 730                 735

Tyr Ala Tyr Leu Arg Lys His Phe Ser Met Met Ile Leu Ser Asp Asp
            740                 745                 750

Ala Val Val Cys Tyr Asn Ser Asn Tyr Ala Ala Gln Gly Leu Val Ala
        755                 760                 765

Ser Ile Lys Asn Phe Lys Ala Val Leu Tyr Tyr Gln Asn Asn Val Phe
770                 775                 780

Met Ser Glu Ala Lys Cys Trp Thr Glu Thr Asp Leu Thr Lys Gly Pro
785                 790                 795                 800

His Glu Phe Cys Ser Gln His Thr Met Leu Val Lys Gln Gly Asp Asp
                805                 810                 815

Tyr Val Tyr Leu Pro Tyr Pro Asp Pro Ser Arg Ile Leu Gly Ala Gly
            820                 825                 830

Cys Phe Val Asp Asp Ile Val Lys Thr Asp Gly Thr Leu Met Ile Glu
        835                 840                 845

Arg Phe Val Ser Leu Ala Ile Asp Ala Tyr Pro Leu Thr Lys His Pro
    850                 855                 860

Asn Gln Glu Tyr Ala Asp Val Phe His Leu Tyr Leu Gln Tyr Ile Arg
865                 870                 875                 880

Lys Leu His Asp Glu Leu Thr Gly His Met Leu Asp Met Tyr Ser Val
                885                 890                 895

Met Leu Thr Asn Asp Asn Thr Ser Arg Tyr Trp Glu Pro Glu Phe Tyr
            900                 905                 910

Glu Ala Met Tyr Thr Pro His Thr Val Leu Gln Ala Val Gly Ala Cys
        915                 920                 925

Val Leu Cys Asn Ser Gln Thr Ser Leu Arg Cys Gly Ala Cys Ile Arg
    930                 935                 940

Arg Pro Phe Leu Cys Cys Lys Cys Cys Tyr Asp His Val Ile Ser Thr
945                 950                 955                 960

Ser His Lys Leu Val Leu Ser Val Asn Pro Tyr Val Cys Asn Ala Pro
                965                 970                 975

Gly Cys Asp Val Thr Asp Val Thr Gln Leu Tyr Leu Gly Gly Met Ser
            980                 985                 990

Tyr Tyr Cys Lys Ser His Lys Pro Pro Ile Ser Phe Pro Leu Cys Ala
        995                 1000                1005

Asn Gly Gln Val Phe Gly Leu Tyr Lys Asn Thr Cys Val Gly Ser
    1010                1015                1020

Asp Asn Val Thr Asp Phe Asn Ala Ile Ala Thr Cys Asp Trp Thr
    1025                1030                1035

Asn Ala Gly Asp Tyr Ile Leu Ala Asn Thr Cys Thr Glu Arg Leu
    1040                1045                1050

Lys Leu Phe Ala Ala Glu Thr Leu Lys Ala Thr Glu Glu Thr Phe
    1055                1060                1065

Lys Leu Ser Tyr Gly Ile Ala Thr Val Arg Glu Val Leu Ser Asp
    1070                1075                1080

Arg Glu Leu His Leu Ser Trp Glu Val Gly Lys Pro Arg Pro Pro
```

```
           1085                1090                1095

Leu Asn Arg Asn Tyr Val Phe Thr Gly Tyr Arg Val Thr Lys Asn
    1100                1105                1110

Ser Lys Val Gln Ile Gly Glu Tyr Thr Phe Glu Lys Gly Asp Tyr
    1115                1120                1125

Gly Asp Ala Val Val Tyr Arg Gly Thr Thr Tyr Lys Leu Asn
    1130                1135                1140

Val Gly Asp Tyr Phe Val Leu Thr Ser His Thr Val Met Pro Leu
    1145                1150                1155

Ser Ala Pro Thr Leu Val Pro Gln Glu His Tyr Val Arg Ile Thr
    1160                1165                1170

Gly Leu Tyr Pro Thr Leu Asn Ile Ser Asp Glu Phe Ser Ser Asn
    1175                1180                1185

Val Ala Asn Tyr Gln Lys Val Gly Met Gln Lys Tyr Ser Thr Leu
    1190                1195                1200

Gln Gly Pro Pro Gly Thr Gly Lys Ser His Phe Ala Ile Gly Leu
    1205                1210                1215

Ala Leu Tyr Tyr Pro Ser Ala Arg Ile Val Tyr Thr Ala Cys Ser
    1220                1225                1230

His Ala Ala Val Asp Ala Leu Cys Glu Lys Ala Leu Lys Tyr Leu
    1235                1240                1245

Pro Ile Asp Lys Cys Ser Arg Ile Ile Pro Ala Arg Ala Arg Val
    1250                1255                1260

Glu Cys Phe Asp Lys Phe Lys Val Asn Ser Thr Leu Glu Gln Tyr
    1265                1270                1275

Val Phe Cys Thr Val Asn Ala Leu Pro Glu Thr Thr Ala Asp Ile
    1280                1285                1290

Val Val Phe Asp Glu Ile Ser Met Ala Thr Asn Tyr Asp Leu Ser
    1295                1300                1305

Val Val Asn Ala Arg Leu Arg Ala Lys His Tyr Val Tyr Ile Gly
    1310                1315                1320

Asp Pro Ala Gln Leu Pro Ala Pro Arg Thr Leu Leu Thr Lys Gly
    1325                1330                1335

Thr Leu Glu Pro Glu Tyr Phe Asn Ser Val Cys Arg Leu Met Lys
    1340                1345                1350

Thr Ile Gly Pro Asp Met Phe Leu Gly Thr Cys Arg Arg Cys Pro
    1355                1360                1365

Ala Glu Ile Val Asp Thr Val Ser Ala Leu Val Tyr Asp Asn Lys
    1370                1375                1380

Leu Lys Ala His Lys Asp Lys Ser Ala Gln Cys Phe Lys Met Phe
    1385                1390                1395

Tyr Lys Gly Val Ile Thr His Asp Val Ser Ser Ala Ile Asn Arg
    1400                1405                1410

Pro Gln Ile Gly Val Val Arg Glu Phe Leu Thr Arg Asn Pro Ala
    1415                1420                1425

Trp Arg Lys Ala Val Phe Ile Ser Pro Tyr Asn Ser Gln Asn Ala
    1430                1435                1440

Val Ala Ser Lys Ile Leu Gly Leu Pro Thr Gln Thr Val Asp Ser
    1445                1450                1455

Ser Gln Gly Ser Glu Tyr Asp Tyr Val Ile Phe Thr Gln Thr Thr
    1460                1465                1470

Glu Thr Ala His Ser Cys Asn Val Asn Arg Phe Asn Val Ala Ile
    1475                1480                1485
```

```
Thr Arg Ala Lys Ile Gly Ile Leu Cys Ile Met Ser Asp Arg Asp
    1490            1495                1500

Leu Tyr Asp Lys Leu Gln Phe Thr Ser Leu Glu Ile Pro Arg Arg
    1505            1510                1515

Asn Val Ala Thr Leu Gln Ala Glu Asn Val Thr Gly Leu Phe Lys
    1520            1525                1530

Asp Cys Ser Lys Ile Ile Thr Gly Leu His Pro Thr Gln Ala Pro
    1535            1540                1545

Thr His Leu Ser Val Asp Ile Lys Phe Lys Thr Glu Gly Leu Cys
    1550            1555                1560

Val Asp Ile Pro Gly Ile Pro Lys Asp Met Thr Tyr Arg Arg Leu
    1565            1570                1575

Ile Ser Met Met Gly Phe Lys Met Asn Tyr Gln Val Asn Gly Tyr
    1580            1585                1590

Pro Asn Met Phe Ile Thr Arg Glu Glu Ala Ile Arg His Val Arg
    1595            1600                1605

Ala Trp Ile Gly Phe Asp Val Glu Gly Cys His Ala Thr Arg Asp
    1610            1615                1620

Ala Val Gly Thr Asn Leu Pro Leu Gln Leu Gly Phe Ser Thr Gly
    1625            1630                1635

Val Asn Leu Val Ala Val Pro Thr Gly Tyr Val Asp Thr Glu Asn
    1640            1645                1650

Asn Thr Glu Phe Thr Arg Val Asn Ala Lys Pro Pro Pro Gly Asp
    1655            1660                1665

Gln Phe Lys His Leu Ile Pro Leu Met Tyr Lys Gly Leu Pro Trp
    1670            1675                1680

Asn Val Val Arg Ile Lys Ile Val Gln Met Leu Ser Asp Thr Leu
    1685            1690                1695

Lys Gly Leu Ser Asp Arg Val Val Phe Val Leu Trp Ala His Gly
    1700            1705                1710

Phe Glu Leu Thr Ser Met Lys Tyr Phe Val Lys Ile Gly Pro Glu
    1715            1720                1725

Arg Thr Cys Cys Leu Cys Asp Lys Arg Ala Thr Cys Phe Ser Thr
    1730            1735                1740

Ser Ser Asp Thr Tyr Ala Cys Trp Asn His Ser Val Gly Phe Asp
    1745            1750                1755

Tyr Val Tyr Asn Pro Phe Met Ile Asp Val Gln Gln Trp Gly Phe
    1760            1765                1770

Thr Gly Asn Leu Gln Ser Asn His Asp Gln His Cys Gln Val His
    1775            1780                1785

Gly Asn Ala His Val Ala Ser Cys Asp Ala Ile Met Thr Arg Cys
    1790            1795                1800

Leu Ala Val His Glu Cys Phe Val Lys Arg Val Asp Trp Ser Val
    1805            1810                1815

Glu Tyr Pro Ile Ile Gly Asp Glu Leu Arg Val Asn Ser Ala Cys
    1820            1825                1830

Arg Lys Val Gln His Met Val Val Lys Ser Ala Leu Leu Ala Asp
    1835            1840                1845

Lys Phe Pro Val Leu His Asp Ile Gly Asn Pro Lys Ala Ile Lys
    1850            1855                1860

Cys Val Pro Gln Ala Glu Val Glu Trp Lys Phe Tyr Asp Ala Gln
    1865            1870                1875
```

-continued

| | | | | | | | | | | | | |
|---|---|---|---|---|---|---|---|---|---|---|---|---|
| Pro | Cys | Ser | Asp | Lys | Ala | Tyr | Lys | Ile | Glu | Glu | Leu | Phe | Tyr | Ser |
| | 1880 | | | | 1885 | | | | 1890 | | | | | |
| Tyr | Ala | Thr | His | His | Asp | Lys | Phe | Thr | Asp | Gly | Val | Cys | Leu | Phe |
| | 1895 | | | | 1900 | | | | 1905 | | | | | |
| Trp | Asn | Cys | Asn | Val | Asp | Arg | Tyr | Pro | Ala | Asn | Ala | Ile | Val | Cys |
| | 1910 | | | | 1915 | | | | 1920 | | | | | |
| Arg | Phe | Asp | Thr | Arg | Val | Leu | Ser | Asn | Leu | Asn | Leu | Pro | Gly | Cys |
| | 1925 | | | | 1930 | | | | 1935 | | | | | |
| Asp | Gly | Gly | Ser | Leu | Tyr | Val | Asn | Lys | His | Ala | Phe | His | Thr | Pro |
| | 1940 | | | | 1945 | | | | 1950 | | | | | |
| Ala | Phe | Asp | Lys | Ser | Ala | Phe | Thr | Asn | Leu | Lys | Gln | Leu | Pro | Phe |
| | 1955 | | | | 1960 | | | | 1965 | | | | | |
| Phe | Tyr | Tyr | Ser | Asp | Ser | Pro | Cys | Glu | Ser | His | Gly | Lys | Gln | Val |
| | 1970 | | | | 1975 | | | | 1980 | | | | | |
| Val | Ser | Asp | Ile | Asp | Tyr | Val | Pro | Leu | Lys | Ser | Ala | Thr | Cys | Ile |
| | 1985 | | | | 1990 | | | | 1995 | | | | | |
| Thr | Arg | Cys | Asn | Leu | Gly | Gly | Ala | Val | Cys | Arg | His | His | Ala | Asn |
| | 2000 | | | | 2005 | | | | 2010 | | | | | |
| Glu | Tyr | Arg | Gln | Tyr | Leu | Asp | Ala | Tyr | Asn | Met | Met | Ile | Ser | Ala |
| | 2015 | | | | 2020 | | | | 2025 | | | | | |
| Gly | Phe | Ser | Leu | Trp | Ile | Tyr | Lys | Gln | Phe | Asp | Thr | Tyr | Asn | Leu |
| | 2030 | | | | 2035 | | | | 2040 | | | | | |
| Trp | Asn | Thr | Phe | Thr | Arg | Leu | Gln | Ser | Leu | Glu | Asn | Val | Ala | Tyr |
| | 2045 | | | | 2050 | | | | 2055 | | | | | |
| Asn | Val | Val | Asn | Lys | Gly | His | Phe | Asp | Gly | His | Ala | Gly | Glu | Ala |
| | 2060 | | | | 2065 | | | | 2070 | | | | | |
| Pro | Val | Ser | Ile | Ile | Asn | Asn | Ala | Val | Tyr | Thr | Lys | Val | Asp | Gly |
| | 2075 | | | | 2080 | | | | 2085 | | | | | |
| Ile | Asp | Val | Glu | Ile | Phe | Glu | Asn | Lys | Thr | Thr | Leu | Pro | Val | Asn |
| | 2090 | | | | 2095 | | | | 2100 | | | | | |
| Val | Ala | Phe | Glu | Leu | Trp | Ala | Lys | Arg | Asn | Ile | Lys | Pro | Val | Pro |
| | 2105 | | | | 2110 | | | | 2115 | | | | | |
| Glu | Ile | Lys | Ile | Leu | Asn | Asn | Leu | Gly | Val | Asp | Ile | Ala | Ala | Asn |
| | 2120 | | | | 2125 | | | | 2130 | | | | | |
| Thr | Val | Ile | Trp | Asp | Tyr | Lys | Arg | Glu | Ala | Pro | Ala | His | Val | Ser |
| | 2135 | | | | 2140 | | | | 2145 | | | | | |
| Thr | Ile | Gly | Val | Cys | Thr | Met | Thr | Asp | Ile | Ala | Lys | Lys | Pro | Thr |
| | 2150 | | | | 2155 | | | | 2160 | | | | | |
| Glu | Ser | Ala | Cys | Ser | Ser | Leu | Thr | Val | Leu | Phe | Asp | Gly | Arg | Val |
| | 2165 | | | | 2170 | | | | 2175 | | | | | |
| Glu | Gly | Gln | Val | Asp | Leu | Phe | Arg | Asn | Ala | Arg | Asn | Gly | Val | Leu |
| | 2180 | | | | 2185 | | | | 2190 | | | | | |
| Ile | Thr | Glu | Gly | Ser | Val | Lys | Gly | Leu | Thr | Pro | Ser | Lys | Gly | Pro |
| | 2195 | | | | 2200 | | | | 2205 | | | | | |
| Ala | Gln | Ala | Ser | Val | Asn | Gly | Val | Thr | Leu | Ile | Gly | Glu | Ser | Val |
| | 2210 | | | | 2215 | | | | 2220 | | | | | |
| Lys | Thr | Gln | Phe | Asn | Tyr | Phe | Lys | Lys | Val | Asp | Gly | Ile | Ile | Gln |
| | 2225 | | | | 2230 | | | | 2235 | | | | | |
| Gln | Leu | Pro | Glu | Thr | Tyr | Phe | Thr | Gln | Ser | Arg | Asp | Leu | Glu | Asp |
| | 2240 | | | | 2245 | | | | 2250 | | | | | |
| Phe | Lys | Pro | Arg | Ser | Gln | Met | Glu | Thr | Asp | Phe | Leu | Glu | Leu | Ala |
| | 2255 | | | | 2260 | | | | 2265 | | | | | |
| Met | Asp | Glu | Phe | Ile | Gln | Arg | Tyr | Lys | Leu | Glu | Gly | Tyr | Ala | Phe |

-continued

```
            2270                2275                2280

Glu His Ile Val Tyr Gly Asp Phe Ser His Gly Gln Leu Gly Gly
    2285                2290                2295

Leu His Leu Met Ile Gly Leu Ala Lys Arg Ser Gln Asp Ser Pro
    2300                2305                2310

Leu Lys Leu Glu Asp Phe Ile Pro Met Asp Ser Thr Val Lys Asn
    2315                2320                2325

Tyr Phe Ile Thr Asp Ala Gln Thr Gly Ser Ser Lys Cys Val Cys
    2330                2335                2340

Ser Val Ile Asp Leu Leu Asp Asp Phe Val Glu Ile Ile Lys
    2345                2350                2355

Ser Gln Asp Leu Ser Val Ile Ser Lys Val Val Lys Val Thr Ile
    2360                2365                2370

Asp Tyr Ala Glu Ile Ser Phe Met Leu Trp Cys Lys Asp Gly His
    2375                2380                2385

Val Glu Thr Phe Tyr Pro Lys Leu Gln Ala Ser Gln Ala Trp Gln
    2390                2395                2400

Pro Gly Val Ala Met Pro Asn Leu Tyr Lys Met Gln Arg Met Leu
    2405                2410                2415

Leu Glu Lys Cys Asp Leu Gln Asn Tyr Gly Glu Asn Ala Val Ile
    2420                2425                2430

Pro Lys Gly Ile Met Met Asn Val Ala Lys Tyr Thr Gln Leu Cys
    2435                2440                2445

Gln Tyr Leu Asn Thr Leu Thr Leu Ala Val Pro Tyr Asn Met Arg
    2450                2455                2460

Val Ile His Phe Gly Ala Gly Ser Asp Lys Gly Val Ala Pro Gly
    2465                2470                2475

Thr Ala Val Leu Arg Gln Trp Leu Pro Thr Gly Thr Leu Leu Val
    2480                2485                2490

Asp Ser Asp Leu Asn Asp Phe Val Ser Asp Ala Asp Ser Thr Leu
    2495                2500                2505

Ile Gly Asp Cys Ala Thr Val His Thr Ala Asn Lys Trp Asp Leu
    2510                2515                2520

Ile Ile Ser Asp Met Tyr Asp Pro Arg Thr Lys His Val Thr Lys
    2525                2530                2535

Glu Asn Asp Ser Lys Glu Gly Phe Phe Thr Tyr Leu Cys Gly Phe
    2540                2545                2550

Ile Lys Gln Lys Leu Ala Leu Gly Gly Ser Ile Ala Val Lys Ile
    2555                2560                2565

Thr Glu His Ser Trp Asn Ala Asp Leu Tyr Lys Leu Met Gly His
    2570                2575                2580

Phe Ser Trp Trp Thr Ala Phe Val Thr Asn Val Asn Ala Ser Ser
    2585                2590                2595

Ser Glu Ala Phe Leu Ile Gly Ala Asn Tyr Leu Gly Lys Pro Lys
    2600                2605                2610

Glu Gln Ile Asp Gly Tyr Thr Met His Ala Asn Tyr Ile Phe Trp
    2615                2620                2625

Arg Asn Thr Asn Pro Ile Gln Leu Ser Ser Tyr Ser Leu Phe Asp
    2630                2635                2640

Met Ser Lys Phe Pro Leu Lys Leu Arg Gly Thr Ala Val Met Ser
    2645                2650                2655

Leu Lys Glu Asn Gln Ile Asn Asp Met Ile Tyr Ser Leu Leu Glu
    2660                2665                2670
```

```
Lys Gly Arg Leu Ile Ile Arg Glu Asn Asn Arg Val Val Val Ser
    2675                2680                2685

Ser Asp Ile Leu Val Asn Asn
    2690            2695

<210> SEQ ID NO 4
<211> LENGTH: 1255
<212> TYPE: PRT
<213> ORGANISM: Coronavirus

<400> SEQUENCE: 4

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
```

-continued

```
                340                 345                 350
Ser Val Leu Tyr Asn Ser Thr Phe Phe Ser Thr Phe Lys Cys Tyr Gly
            355                 360                 365
Val Ser Ala Thr Lys Leu Asn Asp Leu Cys Phe Ser Asn Val Tyr Ala
        370                 375                 380
Asp Ser Phe Val Val Lys Gly Asp Val Arg Gln Ile Ala Pro Gly
385                 390                 395                 400
Gln Thr Gly Val Ile Ala Asp Tyr Asn Tyr Lys Leu Pro Asp Asp Phe
                405                 410                 415
Met Gly Cys Val Leu Ala Trp Asn Thr Arg Asn Ile Asp Ala Thr Ser
            420                 425                 430
Thr Gly Asn Tyr Asn Tyr Lys Tyr Arg Tyr Leu Arg His Gly Lys Leu
        435                 440                 445
Arg Pro Phe Glu Arg Asp Ile Ser Asn Val Pro Phe Ser Pro Asp Gly
    450                 455                 460
Lys Pro Cys Thr Pro Pro Ala Leu Asn Cys Tyr Trp Pro Leu Asn Asp
465                 470                 475                 480
Tyr Gly Phe Tyr Thr Thr Thr Gly Ile Gly Tyr Gln Pro Tyr Arg Val
                485                 490                 495
Val Val Leu Ser Phe Glu Leu Leu Asn Ala Pro Ala Thr Val Cys Gly
            500                 505                 510
Pro Lys Leu Ser Thr Asp Leu Ile Lys Asn Gln Cys Val Asn Phe Asn
        515                 520                 525
Phe Asn Gly Leu Thr Gly Thr Gly Val Leu Thr Pro Ser Ser Lys Arg
    530                 535                 540
Phe Gln Pro Phe Gln Gln Phe Gly Arg Asp Val Ser Asp Phe Thr Asp
545                 550                 555                 560
Ser Val Arg Asp Pro Lys Thr Ser Glu Ile Leu Asp Ile Ser Pro Cys
                565                 570                 575
Ser Phe Gly Gly Val Ser Val Ile Thr Pro Gly Thr Asn Ala Ser Ser
            580                 585                 590
Glu Val Ala Val Leu Tyr Gln Asp Val Asn Cys Thr Asp Val Ser Thr
        595                 600                 605
Ala Ile His Ala Asp Gln Leu Thr Pro Ala Trp Arg Ile Tyr Ser Thr
    610                 615                 620
Gly Asn Asn Val Phe Gln Thr Gln Ala Gly Cys Leu Ile Gly Ala Glu
625                 630                 635                 640
His Val Asp Thr Ser Tyr Glu Cys Asp Ile Pro Ile Gly Ala Gly Ile
                645                 650                 655
Cys Ala Ser Tyr His Thr Val Ser Leu Leu Arg Ser Thr Ser Gln Lys
            660                 665                 670
Ser Ile Val Ala Tyr Thr Met Ser Leu Gly Ala Asp Ser Ser Ile Ala
        675                 680                 685
Tyr Ser Asn Asn Thr Ile Ala Ile Pro Thr Asn Phe Ser Ile Ser Ile
    690                 695                 700
Thr Thr Glu Val Met Pro Val Ser Met Ala Lys Thr Ser Val Asp Cys
705                 710                 715                 720
Asn Met Tyr Ile Cys Gly Asp Ser Thr Glu Cys Ala Asn Leu Leu Leu
                725                 730                 735
Gln Tyr Gly Ser Phe Cys Thr Gln Leu Asn Arg Ala Leu Ser Gly Ile
            740                 745                 750
Ala Ala Glu Gln Asp Arg Asn Thr Arg Glu Val Phe Ala Gln Val Lys
        755                 760                 765
```

-continued

```
Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                    805                 810                 815

Lys Gln Tyr Gly Glu Cys Leu Gly Asp Ile Asn Ala Arg Asp Leu Ile
                820                 825                 830

Cys Ala Gln Lys Phe Asn Gly Leu Thr Val Leu Pro Pro Leu Leu Thr
                835                 840                 845

Asp Asp Met Ile Ala Ala Tyr Thr Ala Ala Leu Val Ser Gly Thr Ala
850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
                900                 905                 910

Ile Ser Gln Ile Gln Glu Ser Leu Thr Thr Thr Ser Thr Ala Leu Gly
                915                 920                 925

Lys Leu Gln Asp Val Val Asn Gln Asn Ala Gln Ala Leu Asn Thr Leu
930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
                980                 985                 990

Gln Leu Ile Arg Ala Ala Glu Ile Arg Ala Ser Ala Asn Leu Ala Ala
                995                1000                1005

Thr Lys Met Ser Glu Cys Val Leu Gly Gln Ser Lys Arg Val Asp
   1010                1015                1020

Phe Cys Gly Lys Gly Tyr His Leu Met Ser Phe Pro Gln Ala Ala
   1025                1030                1035

Pro His Gly Val Val Phe Leu His Val Thr Tyr Val Pro Ser Gln
   1040                1045                1050

Glu Arg Asn Phe Thr Thr Ala Pro Ala Ile Cys His Glu Gly Lys
   1055                1060                1065

Ala Tyr Phe Pro Arg Glu Gly Val Phe Val Phe Asn Gly Thr Ser
   1070                1075                1080

Trp Phe Ile Thr Gln Arg Asn Phe Phe Ser Pro Gln Ile Ile Thr
   1085                1090                1095

Thr Asp Asn Thr Phe Val Ser Gly Asn Cys Asp Val Val Ile Gly
   1100                1105                1110

Ile Ile Asn Asn Thr Val Tyr Asp Pro Leu Gln Pro Glu Leu Asp
   1115                1120                1125

Ser Phe Lys Glu Glu Leu Asp Lys Tyr Phe Lys Asn His Thr Ser
   1130                1135                1140

Pro Asp Val Asp Leu Gly Asp Ile Ser Gly Ile Asn Ala Ser Val
   1145                1150                1155

Val Asn Ile Gln Lys Glu Ile Asp Arg Leu Asn Glu Val Ala Lys
   1160                1165                1170
```

-continued

Asn Leu Asn Glu Ser Leu Ile Asp Leu Gln Glu Leu Gly Lys Tyr
    1175                1180                1185

Glu Gln Tyr Ile Lys Trp Pro Trp Tyr Val Trp Leu Gly Phe Ile
    1190                1195                1200

Ala Gly Leu Ile Ala Ile Val Met Val Thr Ile Leu Leu Cys Cys
    1205                1210                1215

Met Thr Ser Cys Cys Ser Cys Leu Lys Gly Ala Cys Ser Cys Gly
    1220                1225                1230

Ser Cys Cys Lys Phe Asp Glu Asp Asp Ser Glu Pro Val Leu Lys
    1235                1240                1245

Gly Val Lys Leu His Tyr Thr
    1250                1255

<210> SEQ ID NO 5
<211> LENGTH: 274
<212> TYPE: PRT
<213> ORGANISM: Coronavirus

<400> SEQUENCE: 5

Met Asp Leu Phe Met Arg Phe Phe Thr Leu Gly Ser Ile Thr Ala Gln
1               5                   10                  15

Pro Val Lys Ile Asp Asn Ala Ser Pro Ala Ser Thr Val His Ala Thr
            20                  25                  30

Ala Thr Ile Pro Leu Gln Ala Ser Leu Pro Phe Gly Trp Leu Val Ile
        35                  40                  45

Gly Val Ala Phe Leu Ala Val Phe Gln Ser Ala Thr Lys Ile Ile Ala
    50                  55                  60

Leu Asn Lys Arg Trp Gln Leu Ala Leu Tyr Lys Gly Phe Gln Phe Ile
65                  70                  75                  80

Cys Asn Leu Leu Leu Leu Phe Val Thr Ile Tyr Ser His Leu Leu Leu
                85                  90                  95

Val Ala Ala Gly Met Glu Ala Gln Phe Leu Tyr Leu Tyr Ala Leu Ile
            100                 105                 110

Tyr Phe Leu Gln Cys Ile Asn Ala Cys Arg Ile Ile Met Arg Cys Trp
        115                 120                 125

Leu Cys Trp Lys Cys Lys Ser Lys Asn Pro Leu Leu Tyr Asp Ala Asn
    130                 135                 140

Tyr Phe Val Cys Trp His Thr His Asn Tyr Asp Tyr Cys Ile Pro Tyr
145                 150                 155                 160

Asn Ser Val Thr Asp Thr Ile Val Val Thr Glu Gly Asp Gly Ile Ser
                165                 170                 175

Thr Pro Lys Leu Lys Glu Asp Tyr Gln Ile Gly Gly Tyr Ser Glu Asp
            180                 185                 190

Arg His Ser Gly Val Lys Asp Tyr Val Val Val His Gly Tyr Phe Thr
        195                 200                 205

Glu Val Tyr Tyr Gln Leu Glu Ser Thr Gln Ile Thr Thr Asp Thr Gly
    210                 215                 220

Ile Glu Asn Ala Thr Phe Phe Ile Phe Asn Lys Leu Val Lys Asp Pro
225                 230                 235                 240

Pro Asn Val Gln Ile His Thr Ile Asp Gly Ser Ser Gly Val Ala Asn
                245                 250                 255

Pro Ala Met Asp Pro Ile Tyr Asp Glu Pro Thr Thr Thr Thr Ser Val
            260                 265                 270

Pro Leu

<210> SEQ ID NO 6
<211> LENGTH: 154
<212> TYPE: PRT
<213> ORGANISM: Coronavirus

<400> SEQUENCE: 6

Met Met Pro Thr Thr Leu Phe Ala Gly Thr His Ile Thr Met Thr Thr
1               5                   10                  15

Val Tyr His Ile Thr Val Ser Gln Ile Gln Leu Ser Leu Leu Lys Val
            20                  25                  30

Thr Ala Phe Gln His Gln Asn Ser Lys Lys Thr Thr Lys Leu Val Val
        35                  40                  45

Ile Leu Arg Ile Gly Thr Gln Val Leu Lys Thr Met Ser Leu Tyr Met
    50                  55                  60

Ala Ile Ser Pro Lys Phe Thr Thr Ser Leu Ser Leu His Lys Leu Leu
65                  70                  75                  80

Gln Thr Leu Val Leu Lys Met Leu His Ser Ser Leu Thr Ser Leu
                85                  90                  95

Leu Lys Thr His Arg Met Cys Lys Tyr Thr Gln Ser Thr Ala Leu Gln
            100                 105                 110

Glu Leu Leu Ile Gln Gln Trp Ile Gln Phe Met Met Ser Arg Arg Arg
        115                 120                 125

Leu Leu Ala Cys Leu Cys Lys His Lys Lys Val Ser Thr Asn Leu Cys
    130                 135                 140

Thr His Ser Phe Arg Lys Lys Gln Val Arg
145                 150

<210> SEQ ID NO 7
<211> LENGTH: 76
<212> TYPE: PRT
<213> ORGANISM: Coronavirus

<400> SEQUENCE: 7

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Thr Val Tyr Val Tyr Ser Arg Val Lys Asn
    50                  55                  60

Leu Asn Ser Ser Glu Gly Val Pro Asp Leu Leu Val
65                  70                  75

<210> SEQ ID NO 8
<211> LENGTH: 221
<212> TYPE: PRT
<213> ORGANISM: Coronavirus

<400> SEQUENCE: 8

Met Ala Asp Asn Gly Thr Ile Thr Val Glu Glu Leu Lys Gln Leu Leu
1               5                   10                  15

Glu Gln Trp Asn Leu Val Ile Gly Phe Leu Phe Leu Ala Trp Ile Met
            20                  25                  30

Leu Leu Gln Phe Ala Tyr Ser Asn Arg Asn Arg Phe Leu Tyr Ile Ile
        35                  40                  45

Lys Leu Val Phe Leu Trp Leu Leu Trp Pro Val Thr Leu Ala Cys Phe

-continued

```
                 50                  55                  60
Val Leu Ala Ala Val Tyr Arg Ile Asn Trp Val Thr Gly Gly Ile Ala
 65                  70                  75                  80

Ile Ala Met Ala Cys Ile Val Gly Leu Met Trp Leu Ser Tyr Phe Val
                 85                  90                  95

Ala Ser Phe Arg Leu Phe Ala Arg Thr Arg Ser Met Trp Ser Phe Asn
                100                 105                 110

Pro Glu Thr Asn Ile Leu Leu Asn Val Pro Leu Arg Gly Thr Ile Val
                115                 120                 125

Thr Arg Pro Leu Met Glu Ser Glu Leu Val Ile Gly Ala Val Ile Ile
            130                 135                 140

Arg Gly His Leu Arg Met Ala Gly His Pro Leu Gly Arg Cys Asp Ile
145                 150                 155                 160

Lys Asp Leu Pro Lys Glu Ile Thr Val Ala Thr Ser Arg Thr Leu Ser
                165                 170                 175

Tyr Tyr Lys Leu Gly Ala Ser Gln Arg Val Gly Thr Asp Ser Gly Phe
                180                 185                 190

Ala Ala Tyr Asn Arg Tyr Arg Ile Gly Asn Tyr Lys Leu Asn Thr Asp
            195                 200                 205

His Ala Gly Ser Asn Asp Asn Ile Ala Leu Leu Val Gln
    210                 215                 220

<210> SEQ ID NO 9
<211> LENGTH: 63
<212> TYPE: PRT
<213> ORGANISM: Coronavirus

<400> SEQUENCE: 9

Met Phe His Leu Val Asp Phe Gln Val Thr Ile Ala Glu Ile Leu Ile
  1               5                  10                  15

Ile Ile Met Arg Thr Phe Arg Ile Ala Ile Trp Asn Leu Asp Val Ile
                 20                  25                  30

Ile Ser Ser Ile Val Arg Gln Leu Phe Lys Pro Leu Thr Lys Lys Asn
             35                  40                  45

Tyr Ser Glu Leu Asp Asp Glu Glu Pro Met Glu Leu Asp Tyr Pro
         50                  55                  60

<210> SEQ ID NO 10
<211> LENGTH: 122
<212> TYPE: PRT
<213> ORGANISM: Coronavirus

<400> SEQUENCE: 10

Met Lys Ile Ile Leu Phe Leu Thr Leu Ile Val Phe Thr Ser Cys Glu
  1               5                  10                  15

Leu Tyr His Tyr Gln Glu Cys Val Arg Gly Thr Thr Val Leu Leu Lys
                 20                  25                  30

Glu Pro Cys Pro Ser Gly Thr Tyr Glu Gly Asn Ser Pro Phe His Pro
             35                  40                  45

Leu Ala Asp Asn Lys Phe Ala Leu Thr Cys Thr Ser Thr His Phe Ala
         50                  55                  60

Phe Ala Cys Ala Asp Gly Thr Arg His Thr Tyr Gln Leu Arg Ala Arg
 65                  70                  75                  80

Ser Val Ser Pro Lys Leu Phe Ile Arg Gln Glu Glu Val Gln Gln Glu
                 85                  90                  95

Leu Tyr Ser Pro Leu Phe Leu Ile Val Ala Ala Leu Val Phe Leu Ile
```

```
                    100                 105                 110

Leu Cys Phe Thr Ile Lys Arg Lys Thr Glu
        115                 120

<210> SEQ ID NO 11
<211> LENGTH: 84
<212> TYPE: PRT
<213> ORGANISM: Coronavirus

<400> SEQUENCE: 11

Met Cys Leu Lys Ile Leu Val Arg Tyr Asn Thr Arg Gly Asn Thr Tyr
1               5                   10                  15

Ser Thr Ala Trp Leu Cys Ala Leu Gly Lys Val Leu Pro Phe His Arg
            20                  25                  30

Trp His Thr Met Val Gln Thr Cys Thr Pro Asn Val Thr Ile Asn Cys
        35                  40                  45

Gln Asp Pro Ala Gly Gly Ala Leu Ile Ala Arg Cys Trp Tyr Leu His
    50                  55                  60

Glu Gly His Gln Thr Ala Ala Phe Arg Asp Val Leu Val Val Leu Asn
65                  70                  75                  80

Lys Arg Thr Asn

<210> SEQ ID NO 12
<211> LENGTH: 422
<212> TYPE: PRT
<213> ORGANISM: Coronavirus

<400> SEQUENCE: 12

Met Ser Asp Asn Gly Pro Gln Ser Asn Gln Arg Ser Ala Pro Arg Ile
1               5                   10                  15

Thr Phe Gly Gly Pro Thr Asp Ser Thr Asp Asn Asn Gln Asn Gly Gly
            20                  25                  30

Arg Asn Gly Ala Arg Pro Lys Gln Arg Arg Pro Gln Gly Leu Pro Asn
        35                  40                  45

Asn Thr Ala Ser Trp Phe Thr Ala Leu Thr Gln His Gly Lys Glu Glu
    50                  55                  60

Leu Arg Phe Pro Arg Gly Gln Gly Val Pro Ile Asn Thr Asn Ser Gly
65                  70                  75                  80

Pro Asp Asp Gln Ile Gly Tyr Tyr Arg Arg Ala Thr Arg Arg Val Arg
                85                  90                  95

Gly Gly Asp Gly Lys Met Lys Glu Leu Ser Pro Arg Trp Tyr Phe Tyr
            100                 105                 110

Tyr Leu Gly Thr Gly Pro Glu Ala Ser Leu Pro Tyr Gly Ala Asn Lys
        115                 120                 125

Glu Gly Ile Val Trp Val Ala Thr Glu Gly Ala Leu Asn Thr Pro Lys
    130                 135                 140

Asp His Ile Gly Thr Arg Asn Pro Asn Asn Asn Ala Ala Thr Val Leu
145                 150                 155                 160

Gln Leu Pro Gln Gly Thr Thr Leu Pro Lys Gly Phe Tyr Ala Glu Gly
                165                 170                 175

Ser Arg Gly Gly Ser Gln Ala Ser Ser Arg Ser Ser Ser Arg Ser Arg
            180                 185                 190

Gly Asn Ser Arg Asn Ser Thr Pro Gly Ser Ser Arg Gly Asn Ser Pro
        195                 200                 205

Ala Arg Met Ala Ser Gly Gly Gly Glu Thr Ala Leu Ala Leu Leu Leu
    210                 215                 220
```

-continued

```
Leu Asp Arg Leu Asn Gln Leu Glu Ser Lys Val Ser Gly Lys Gly Gln
225                 230                 235                 240

Gln Gln Gln Gly Gln Thr Val Thr Lys Lys Ser Ala Ala Glu Ala Ser
            245                 250                 255

Lys Lys Pro Arg Gln Lys Arg Thr Ala Thr Lys Gln Tyr Asn Val Thr
        260                 265                 270

Gln Ala Phe Gly Arg Arg Gly Pro Glu Gln Thr Gln Gly Asn Phe Gly
    275                 280                 285

Asp Gln Asp Leu Ile Arg Gln Gly Thr Asp Tyr Lys His Trp Pro Gln
290                 295                 300

Ile Ala Gln Phe Ala Pro Ser Ala Ser Ala Phe Phe Gly Met Ser Arg
305                 310                 315                 320

Ile Gly Met Glu Val Thr Pro Ser Gly Thr Trp Leu Thr Tyr His Gly
                325                 330                 335

Ala Ile Lys Leu Asp Asp Lys Asp Pro Gln Phe Lys Asp Asn Val Ile
            340                 345                 350

Leu Leu Asn Lys His Ile Asp Ala Tyr Lys Thr Phe Pro Pro Thr Glu
        355                 360                 365

Pro Lys Lys Asp Lys Lys Lys Thr Asp Glu Ala Gln Pro Leu Pro
    370                 375                 380

Gln Arg Gln Lys Lys Gln Pro Thr Val Thr Leu Leu Pro Ala Ala Asp
385                 390                 395                 400

Met Asp Asp Phe Ser Arg Gln Leu Gln Asn Ser Met Ser Gly Ala Ser
                405                 410                 415

Ala Asp Ser Thr Gln Ala
            420

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide.

<400> SEQUENCE: 13
ctaacatgct taggataatg g                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide.

<400> SEQUENCE: 14
gcctctcttg ttcttgctcg c                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide.

<400> SEQUENCE: 15
caggtaagcg taaaactcat c                                              21

<210> SEQ ID NO 16
<211> LENGTH: 22
```

```
<212> TYPE: DNA
<213> ORGANISM: Artificial Sequence
<220> FEATURE:
<223> OTHER INFORMATION: Synthetic oligonucleotide.

<400> SEQUENCE: 16
catgtgtggc ggctcactat at                                              22

<210> SEQ ID NO 17
<211> LENGTH: 28
<212> TYPE: DNA
<213> ORGANISM: Artificial Sequence
<220> FEATURE:
<223> OTHER INFORMATION: Synthetic oligonucleotide.

<400> SEQUENCE: 17
gacactatta gcataagcag ttgtagca                                        28

<210> SEQ ID NO 18
<211> LENGTH: 27
<212> TYPE: DNA
<213> ORGANISM: Artificial Sequence
<220> FEATURE:
<223> OTHER INFORMATION: Synthetic oligonucleotide.

<400> SEQUENCE: 18
ttaaaccagg tggaacatca tccggtg                                         27

<210> SEQ ID NO 19
<211> LENGTH: 22
<212> TYPE: DNA
<213> ORGANISM: Artificial Sequence
<220> FEATURE:
<223> OTHER INFORMATION: Synthetic oligonucleotide.

<400> SEQUENCE: 19
ggagccttga atacacccaa ag                                              22

<210> SEQ ID NO 20
<211> LENGTH: 17
<212> TYPE: DNA
<213> ORGANISM: Artificial Sequence
<220> FEATURE:
<223> OTHER INFORMATION: Synthetic oligonucleotide.

<400> SEQUENCE: 20
gcacggtggc agcattg                                                    17

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide.

<400> SEQUENCE: 21
ccacattggc acccgcaatc c                                               21

<210> SEQ ID NO 22
<211> LENGTH: 19
<212> TYPE: DNA
<213> ORGANISM: Artificial Sequence
<220> FEATURE:
<223> OTHER INFORMATION: Synthetic oligonucleotide.

<400> SEQUENCE: 22
```

```
caaacattgg ccgcaaatt                                              19

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide.

<400> SEQUENCE: 23
caatgcgtga cattccaaag a                                           21

<210> SEQ ID NO 24
<211> LENGTH: 26
<212> TYPE: DNA
<213> ORGANISM: Artificial Sequence
<220> FEATURE:
<223> OTHER INFORMATION: Synthetic oligonucleotide.

<400> SEQUENCE: 24
cacaatttgc tccaagtgcc tctgca                                      26

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide.

<400> SEQUENCE: 25
gaagtaccat ctggggctga g                                           21

<210> SEQ ID NO 26
<211> LENGTH: 18
<212> TYPE: DNA
<213> ORGANISM: Artificial Sequence
<220> FEATURE:
<223> OTHER INFORMATION: Synthetic oligonucleotide.

<400> SEQUENCE: 26
ccgaagagct acccgacg                                               18

<210> SEQ ID NO 27
<211> LENGTH: 26
<212> TYPE: DNA
<213> ORGANISM: Artificial Sequence
<220> FEATURE:
<223> OTHER INFORMATION: Synthetic oligonucleotide.

<400> SEQUENCE: 27
ctctttcatt ttgccgtcac caccac                                      26

<210> SEQ ID NO 28
<211> LENGTH: 24
<212> TYPE: DNA
<213> ORGANISM: Artificial Sequence
<220> FEATURE:
<223> OTHER INFORMATION: Synthetic oligonucleotide.

<400> SEQUENCE: 28
agctctccct agcattattc actg                                        24

<210> SEQ ID NO 29
<211> LENGTH: 20
<212> TYPE: DNA
<213> ORGANISM: Artificial Sequence
```

```
<220> FEATURE:
<223> OTHER INFORMATION: Synthetic oligonucleotide.

<400> SEQUENCE: 29
caccacattt tcatcgaggc                                               20

<210> SEQ ID NO 30
<211> LENGTH: 22
<212> TYPE: DNA
<213> ORGANISM: Artificial Sequence
<220> FEATURE:
<223> OTHER INFORMATION: Synthetic oligonucleotide.

<400> SEQUENCE: 30
taccctcgat cgtactccgc gt                                            22

<210> SEQ ID NO 31
<211> LENGTH: 23
<212> TYPE: DNA
<213> ORGANISM: Artificial Sequence
<220> FEATURE:
<223> OTHER INFORMATION: Synthetic oligonucleotide.

<400> SEQUENCE: 31
tgtaggcact gattcaggtt ttg                                           23

<210> SEQ ID NO 32
<211> LENGTH: 23
<212> TYPE: DNA
<213> ORGANISM: Artificial Sequence
<220> FEATURE:
<223> OTHER INFORMATION: Synthetic oligonucleotide.

<400> SEQUENCE: 32
cggcgtggtc tgtatttaat tta                                           23

<210> SEQ ID NO 33
<211> LENGTH: 27
<212> TYPE: DNA
<213> ORGANISM: Artificial Sequence
<220> FEATURE:
<223> OTHER INFORMATION: Synthetic oligonucleotide.

<400> SEQUENCE: 33
ctgcatacaa ccgctaccgt attggaa                                       27

<210> SEQ ID NO 34
<211> LENGTH: 24
<212> TYPE: DNA
<213> ORGANISM: Artificial Sequence
<220> FEATURE:
<223> OTHER INFORMATION: Synthetic oligonucleotide.

<400> SEQUENCE: 34
gggttgggac tatcctaagt gtga                                          24

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide.
<220> FEATURE:
<221> NAME/KEY: misc_feature
<222> LOCATION: (12)..(12)
<223> OTHER INFORMATION: "n" equals inosine.
```

-continued

```
<400> SEQUENCE: 35
taacacacaa cnccatcatc a                                              21

<210> SEQ ID NO 36
<211> LENGTH: 19
<212> TYPE: DNA
<213> ORGANISM: Artificial Sequence
<220> FEATURE:
<223> OTHER INFORMATION: Synthetic oligonucleotide.

<400> SEQUENCE: 36
agatttggac ctgcgagcg                                                 19

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide.

<400> SEQUENCE: 37
gagcggctgt ctccacaagt                                                20

<210> SEQ ID NO 38
<211> LENGTH: 23
<212> TYPE: DNA
<213> ORGANISM: Artificial Sequence
<220> FEATURE:
<223> OTHER INFORMATION: Synthetic oligonucleotide.

<400> SEQUENCE: 38
ttctgacctg aaggctctgc gcg                                            23
```